(12) United States Patent
Tsilosani et al.

(10) Patent No.: US 6,743,638 B1
(45) Date of Patent: Jun. 1, 2004

(54) DETECTION SYSTEM USING LIPOSOMES AND SIGNAL MODIFICATION

(75) Inventors: Marina Tsilosani, Manchester (GB); David J Clarke, Manchester (GB); Christopher J Lloyd, Manchester (GB); Stephen Nicklin, Farnborough (GB); Harmesh S Aojula, Oldham (GB); Michael T Wilson, Brightlingsea (GB)

(73) Assignee: The Secretary of State for Defence, Farnborough (GB)

( * ) Notice: Subject to any disclaimer, the term of this patent is extended or adjusted under 35 U.S.C. 154(b) by 0 days.

(21) Appl. No.: 09/600,118
(22) PCT Filed: Jan. 21, 1999
(86) PCT No.: PCT/GB99/00208
§ 371 (c)(1),
(2), (4) Date: Jul. 12, 2000
(87) PCT Pub. No.: WO99/38009
PCT Pub. Date: Jul. 29, 1999

(30) Foreign Application Priority Data

Jan. 21, 1998 (GB) .............................................. 9801120

(51) Int. Cl.⁷ ........................ G01N 33/53; G01N 33/543
(52) U.S. Cl. ........................ 436/518; 436/164; 436/172; 436/501; 436/512; 436/524; 436/528; 436/532; 436/533; 436/534; 436/823; 436/829; 435/4; 435/6; 435/7.1; 435/7.9; 435/7.92; 435/174; 435/176; 435/177; 435/182; 435/287.1; 435/287.2; 435/287.3; 435/287.6; 435/287.7; 435/808; 435/810; 435/975; 428/402; 428/402.2; 422/68.1

(58) Field of Search .................... 435/7.1, 177, 182, 435/810, 317.1, 4, 6, 7.9, 7.92, 175, 176, 287.1, 287.2, 287.3, 287.6, 287.7, 808, 975; 422/68.1; 436/501, 512, 532, 164, 172, 823, 829, 518, 524, 528, 533, 534; 428/402.2, 402

(56) References Cited

U.S. PATENT DOCUMENTS 4,342,826 A * 8/1982 Cole .......................... 435/177

(List continued on next page.)

FOREIGN PATENT DOCUMENTS

EP 0 255 089 A 2/1998

(List continued on next page.)

OTHER PUBLICATIONS

Paragas et al. The ELF–97 Alkaline Phosphatase Substrate Provides a Bright, Photostable, Fluorescent Signal Amplification Method for Fish. Journal of Histochemistry & Cytochemistry (1997) vol. 45. No. 3, pp. 345–357.*

(List continued on next page.)

*Primary Examiner*—Long V. Le
*Assistant Examiner*—Kartic Padmanabhan
(74) *Attorney, Agent, or Firm*—Nixon & Vanderhye P.C.

(57) ABSTRACT

A process for detecting an analyte which process comprises (a) contacting a sample suspected of containing said analyte with a containment means comprising a barrier which separates signal generating reagents from said sample, in the presence of an element which interacts specifically with said analyte, under conditions whereby interaction between the analyte and the said element results in activation of the signal generating reagents within the containment means on the side of the barrier opposite to the sample, and (b) detecting any signal generated and retained within the containment means from the sample side of the barrier. The process of the invention provides for sensitive detection of very small numbers of analyte materials using measurement techniques which include counting methods such as flow cytometry.

26 Claims, 43 Drawing Sheets

U.S. PATENT DOCUMENTS

| | | | | |
|---|---|---|---|---|
| 4,703,017 | A | * | 10/1987 | Campbell et al. .............. 422/55 |
| 4,806,466 | A | * | 2/1989 | Papahadjopoulos et al. . 264/4.1 |
| 4,913,902 | A | * | 4/1990 | Kilpatrick et al. ........... 424/450 |
| 4,916,080 | A | * | 4/1990 | Imai et al. ................... 436/518 |
| 5,210,040 | A | * | 5/1993 | Jou et al. ..................... 424/450 |
| 5,256,532 | A | * | 10/1993 | Melnicoff et al. .............. 435/5 |
| 5,369,036 | A | * | 11/1994 | Mercolino et al. ........... 435/973 |
| 5,443,955 | A | * | 8/1995 | Cornell et al. ............ 435/317.1 |
| 5,494,803 | A | * | 2/1996 | Carbonell et al. ............. 422/57 |
| 5,561,049 | A | * | 10/1996 | Vold et al. .................... 435/7.1 |
| 5,616,790 | A | * | 4/1997 | Arnold et al. ............ 422/82.08 |
| 5,656,500 | A | * | 8/1997 | Law et al. ................ 428/402.2 |
| 5,693,477 | A | * | 12/1997 | Cornell et al. ............ 435/317.1 |
| 5,710,049 | A | * | 1/1998 | Noppe et al. ................ 422/101 |
| 5,756,362 | A | * | 5/1998 | Durst et al. .................... 422/56 |
| 5,780,319 | A | * | 7/1998 | Maxfield Wilson et al. .. 422/57 |
| 6,248,596 | B1 | * | 6/2001 | Durst et al. ................. 436/518 |

FOREIGN PATENT DOCUMENTS

| | | | |
|---|---|---|---|
| WO | WO 89/01159 | A1 * | 2/1989 |
| WO | WO 96/24062 | A1 * | 8/1996 |
| WO | WO 96 25665 | A | 8/1996 |
| WO | WO 98 00714 | A | 1/1998 |

OTHER PUBLICATIONS

Chemical Abstracts, vol. 129, No. 20, Nov. 16, 1998, abstract No. 269708 & Tsukada et al, "Chemiluminescence from fluorescent organic compounds induced by cobalt (II) catalyzed decomposition of peroxomonosulfate", *Analytica Chimica Acta,* vol. 371, No. 2–3, Feb. 1, 1998, pp. 192–170.
Chemical Abstracts, vol. 125, No. 3, Jul. 15, 1996, abstract No. 32348 & Mizoguchi et al, "Effect of fatty acid saturation in membrane lipid bilayers on simple diffusion in the presence of ethanol at high concentrations", *Journal of Fermentation and Bioengineering,* vol. 81, No. 5, 1996, pp. 406–411.

* cited by examiner

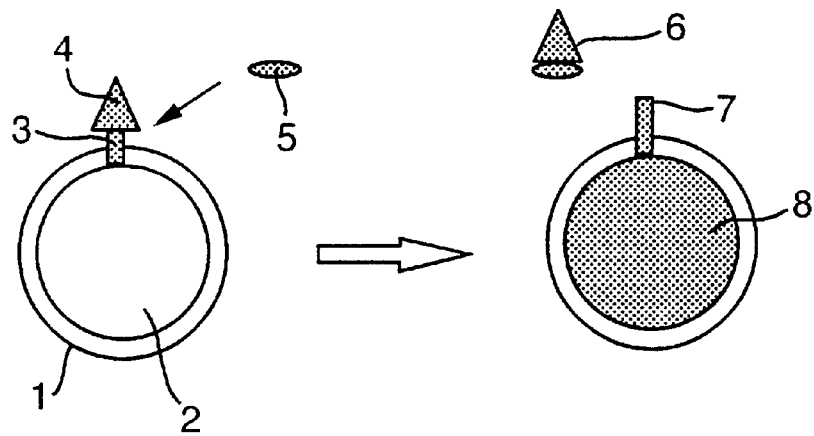
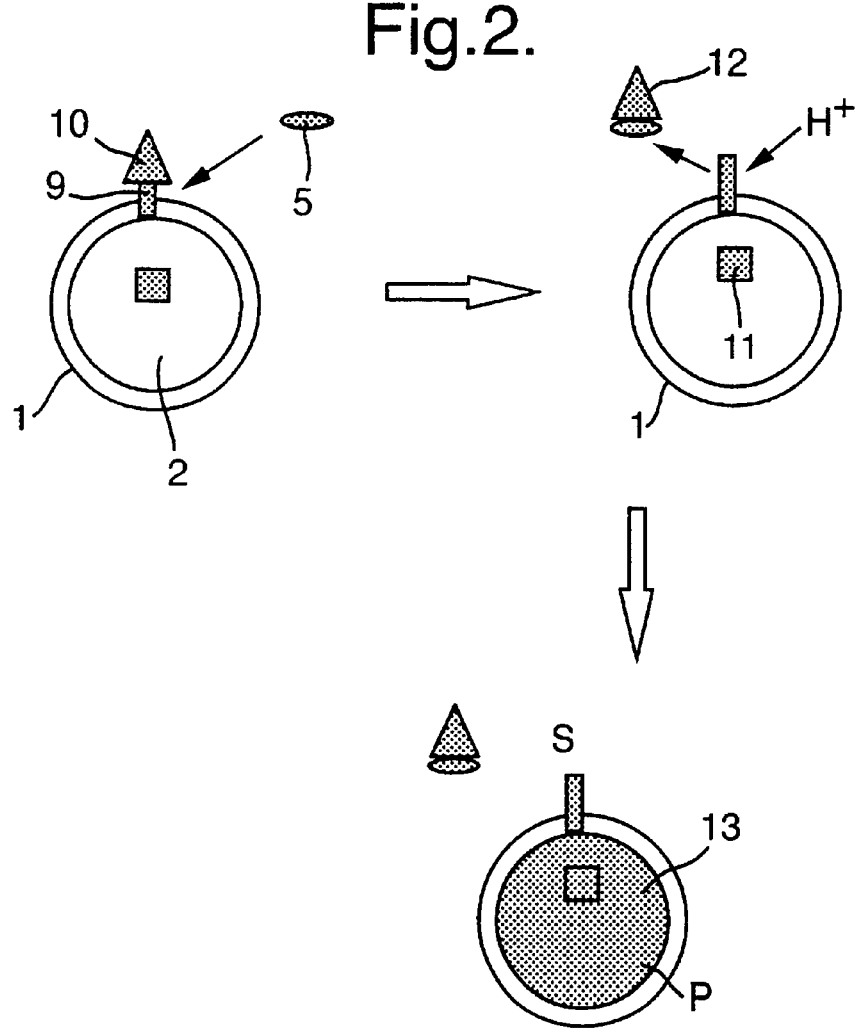

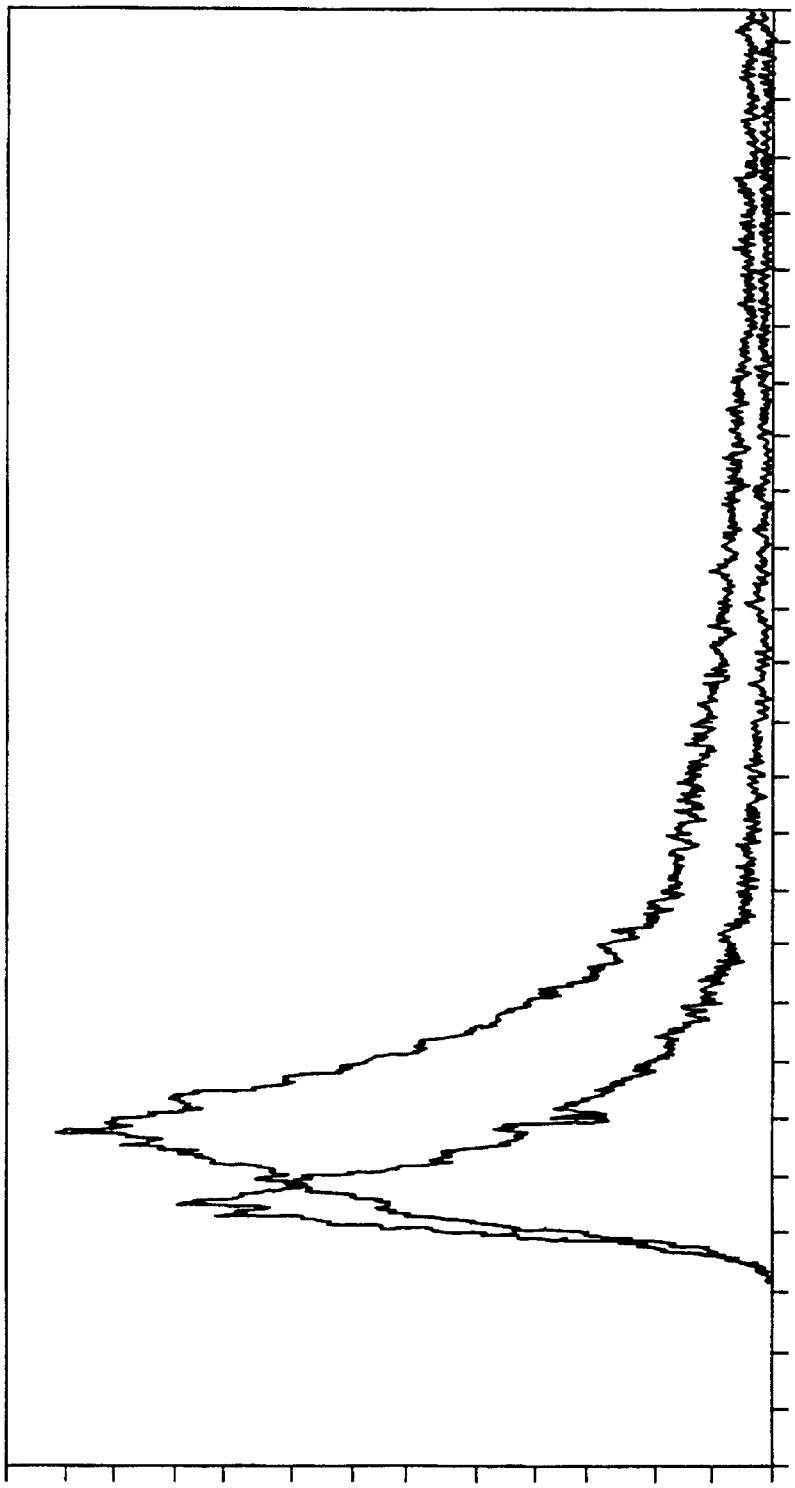

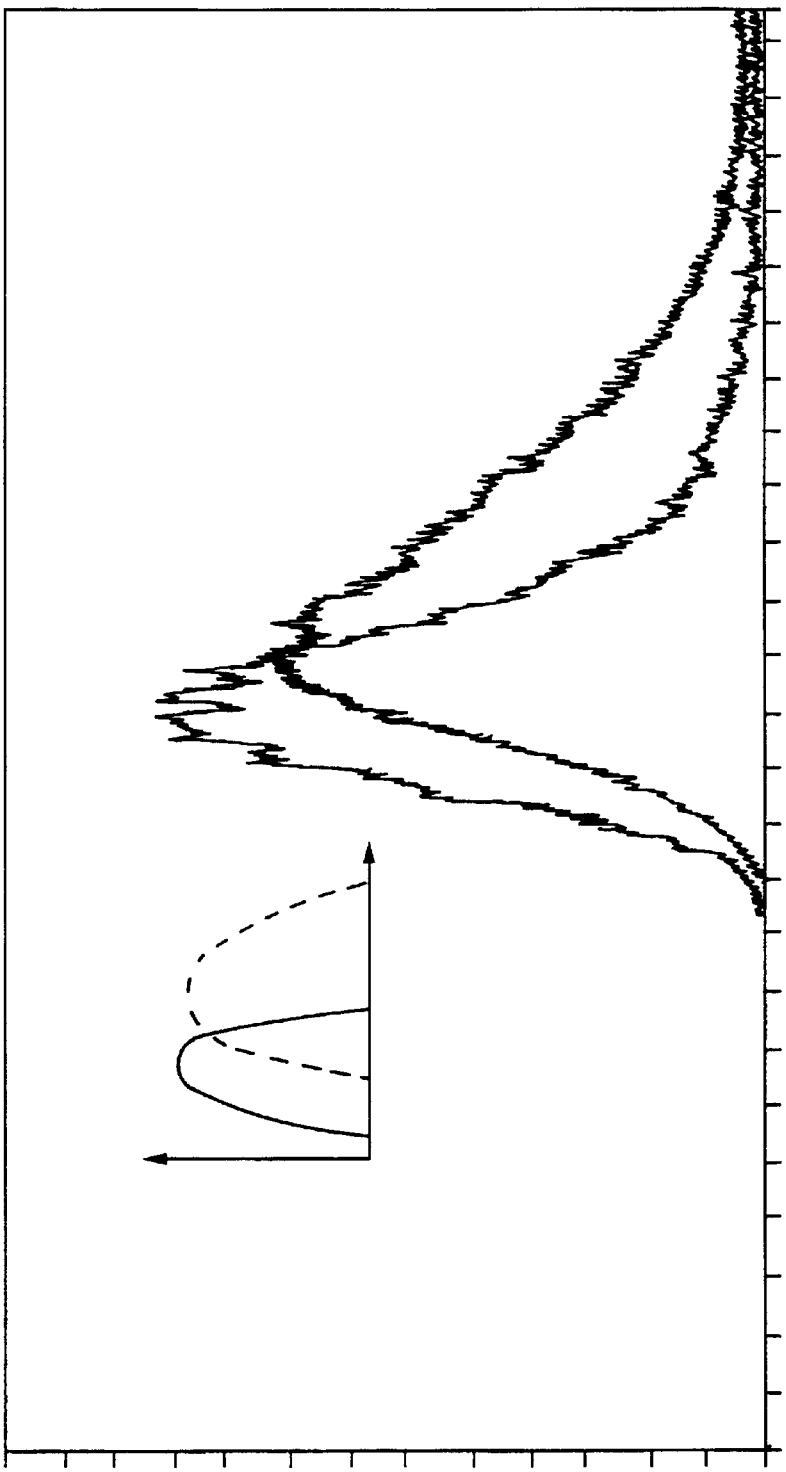

DETECTION SYSTEM USING LIPOSOMES AND SIGNAL MODIFICATION

The present application is a 371 of Application No. PCT/GB99/00208, filed Jan. 21, 1999, which claims the benefit of GB 9801120.8 filed Jan. 21, 1998.

The present invention relates to a method for the detection of analytes, particularly to analytes which are present in only small quantities, as well as to kits and reagents for use in the detection method.

Reactions are widely used in the assay, testing and measurement of chemical, biochemical and biological analytes (e.g. immunoassays). The reaction between an analyte and particular reagents is usually the basis of specificity of such assays. While chemical reagents are the basis for some assays, the higher affinity reaction between analytes and biological molecules (e.g. enzymes, antibodies, nucleic acids) introduces higher specificity and sensitivity into assay procedures. Those reactions providing the highest specificity and sensitivity assays often do not involve the covalent modification of the analyte (e.g. chemical or biochemical enzyme reaction), and instead rely on the binding of the analyte to the specific reagent (e.g. antibody). Many of these covalent and binding reactions are carried out in solution, so that the reaction product and the analyte are present in the same phase. Reactions are detected by various methods such as a change in the optical (e.g. a colour, fluorescent, luminescent, light scattering) or electrochemical (amperometric, potentiometric, conductimetric) properties of the assay or text mixture.

Recent improvements have included the immobilisation of assay reagents for example onto solid supports such as beads or other surfaces. This allows the signal generated to be localised in the same plane. It is therefore more concentrated at this position and so easier to detect. Furthermore, problems with background "noise" signals generated in the bulk of the analyte can be minimised. Examples of such surfaces include lipid films or membranes. Visible signals may be detected in these systems, for example as described in WO 98/00714 and WO 96/25665, or alternatively changes in conductance as a result of the use of ion gating may give rise to analyte detection, for example as described in WO 90/08783 or WO 89/01159.

Liposomes have been used in immunoassays, both as labels to carry a payload of signal molecules, and to release signal molecules in proportion to the level of analyte in the assay medium. In one such method, (W. J. Litchfield et al., Clin. Chem. (1984) 30(9), 1441–1445) liposomes have been lysed to release a signalling means such as a fluorescent dye or enzyme, into an assay reaction mixture in order to generate a signal. The signal however, is diluted throughout the reaction mixture.

The applicants have found an improved process for detecting analytes.

Furthermore, it is known that their are a plurality of methods of varying the output signal parameters of a marker by means of alteration of the energy state of the marker by means of application of a force or field to it. In many instances the force/field may be applied by the locality of a second, or more, entities. An example known in the art is the self quenching of the calcein fluorophore at high concentrations. A second example is the quenching of calcein, and similar fluorescent dyes, by the addition of ions. It is known in the art that cobalt ions quench many fluorophore species. However, the inventors have discovered new effects associated with the use of cobalt ions and other chemicals, which assist in signal generation both in the method of the invention and more generally.

The present invention provides a process for detecting an analyte which process comprises (a) contacting a sample suspected of containing said analyte with a containment means comprising a barrier which separates signal generating reagents from said sample, in the presence of an element which interacts specifically with said analyte, under conditions whereby interaction between the analyte and the said element results in activation of the signal generating reagents within the containment means on the side of the barrier opposite to the sample, and (b) detecting any signal generated and retained within the containment means from the sample side of the barrier.

In this process, although the analyte is free to interact directly or indirectly with the containment means, the signal is generated and retained by the barrier within the containment means. This provides concentration of the signal which is therefore easier to detect.

There is the possibility of amplification of a signal within the containment means. Very small numbers of analyte molecules or even a single analyte molecule, can generate a detectable signal within the containment means, making the system very sensitive for the detection of analyte which is present in only very small quantities.

In one embodiment of the invention, the said element is present on the barrier surface of said containment means prior to interaction with said analyte. In general, interaction with the analyte will result in removal of this element, and this in turn allows transport through the surface of signal activation reagents.

Alternatively, the element may be added to the sample. In this case the element may be associated with a reagent which permeabilises or otherwise allows transport of signal activating reagents through the surface of the containment means such that it blocks or competes with the activity of that reagent. Interaction of the analyte with the element releases this reagent which is then free to react with the containment means so as to allow activation of the signal generating reagents.

In yet a further embodiment, activation of the signal generating reagents may be dependent upon the formation of a complex between the analyte and the element. The thus formed complex may activate the signal generating means for example by interacting with the barrier of the containment means so as to allow signal activation to occur.

The containment means suitably comprises a solid or semi-solid structure whereas the sample may comprise a solid, semi-solid, liquid or a gaseous reagent. Suitably the containment means is in a different physical phase to the sample.

The containment means is suitably of particulate form, in which no one dimension of the 3-dimensional shape of each particle is greater than 4 times any other dimension. In other words, the ratio of the x:y or y:z or x:z or vice versa is not greater than 1:4. Examples of such particles are broadly spherical, such as polymer beads like nanospheres, nanoparticles of microparticles or membrane structures such as vesicles and liposomes. In this case the signal generating agents are contained inside the particle. They are suitably introduced during processes for the production of the particulate containment means.

Particulate containment means can be produced using conventional methods. For example, polymer particles can be produced using a range of processes including the use of phase separation in mixed phase emulsion systems, aggregation and agglutination reactions, extrusion as polymerising or setting beads, and from aerosols. Liposomes and vesicles can be produced by various encapsulation technologies which are known in the art, such as sonication, extrusion and detergent dialysis.

A suitable liposome composition comprises for example a phosphatidylcholine, cholesterol and dihexadecyl phosphate as illustrated hereinafter although other liposome compositions will be apparent to the skilled person. It may be preferable for stability purposes, for the liposomes to be biotinylated in the sense that they incorporate a biotin reagent such as biotinoyl dipalmitoyl phosphatidylethanolamine (biotin-DPPE).

Alternatively, the containment means may comprise a discontinuity, such as a pore structure in a solid or colloid surface, which may be closed to form a complete barrier to sample. Suitable solids include ceramic materials such as glass, metal oxides or silicon. Discontinuities can be introduced into such materials by phase separation or etching processes, or by adding a pattern lithographically or by anodisation. The signal generating agents are suitably introduced into the thus formed discontinuity. The opening to the discontinuity is then closed by the application of a reactive closure means, such as a lipid membrane or layer, which acts as a barrier to prevent ingress of test sample. The reactive closure means can however interact directly or indirectly with any analyte present in a sample applied to it. As a result, signal is generated within the confines of the discontinuity and reactive closure means, which can be detected by observation of reactive closure means from the sample side.

In general, the smaller the size of the containment means, the fewer the number of analyte molecules which are required to interact with the surface of the containment means in order to generate a signal there within. Therefore, where high levels of sensitivity is required, the containment means is made as small as possible. However, the smaller the volume of the containment means, the less signal generation agents can be contained within them and so the detection of the signal or of the containment means itself can be more difficult.

Suitably the containment means of the invention is between 1 nm and 100 $\mu$m across, for example of from 1 nm to 100 $\mu$m diameter where the containment means is generally circular in cross section. For example, the containment means may be of from 10 to 500 nm in size. A particle of dimensions of about 100 nm in diameter provides in practice, a good compromise between transducing a few molecular detection events into a signal which is readily detectable by single particle detection technology. The volume within a 100 nm particle or discontinuity may be of the order of $10^{-18}$L. Volumes of this size may contain a plurality of protein molecules, for example up to 20 protein molecules, or a larger number, for example up to $10^5$ small molecules such as fluorescent dyes.

In a preferred embodiment, the containment means comprises a lipid membrane through which transport of a signal activating means or reagent is inhibited for example as a result of the presence of specific binding elements such as antibodies or binding fragments thereof. Where the containment means comprises a liposome, the entire surface may comprise lipid membrane. Alternatively, the lipid membrane may encapsulate or bind another particle such as a nanosphere, nanoparticle or microparticle, or can be introduced across a discontinuity in a solid surface such as a pore in a ceramic material as outlined above, using conventional methods.

Lipid membranes can prevent significant transport of all molecules other than water or specific molecules which are known to disrupt the membrane structure. Therefore, when used in accordance with the method of the invention, the membranes achieve the selective or specific transport of molecules such as ions, analytes or enzyme substrates into the containment means in order to activate the signal generating reagents, but prevent the signalling agents leaving the containment means.

The precise molecules which can be used to achieve this effect will depend upon various factors such as the nature of the containment means and the size of the signal generating reagents employed. For instance, where the signal generating reagents comprise large enzymes, it is necessary to ensure that, on interaction with an analyte, the membrane is disrupted or permeabilized only to the extent necessary to allow an activating agent such as an enzyme substrate to pass through.

Thus in a preferred embodiment, the interaction between the analyte and the element results in the appearance of a transport mechanism through the surface of the containment means, typically by a perturbation or change in permeability of the surface such as the opening of a channel, so as to allow ingress or egress of moieties which cause activation of the signal generating reagents, but not egress of the signal from the containment means.

Suitably the said element is an antibody or a binding fragment thereof which specifically binds the analyte. Alternatively, it may comprise other ligand binding proteins such as receptors, lectins, avidin or streptavidin.

The nature of the moieties required in order to activate the signal generating means will depend upon the nature of the signal generating means themselves. However, they may be simply comprise ions as illustrated hereinafter.

Suitable surface active and detergent like molecules will be readily apparent to the skilled person. Examples include switched ion carriers, enzyme substrate channels or inserted catalysts or cofactors as illustrated hereinafter.

A range of carrier molecules, such as Crown ether or peptide structures are able either to carry ions across lipid membranes (e.g. valinomycin, monensin) or produce channels in membranes (e.g. alamethicin, gramicidin). However, when attached to a large typically hydrophilic molecule such as a protein or nucleic acid, the transport ability of the molecules is inhibited.

Use can be made of these properties. For example the analyte interaction may be linked to a binding reaction with the large molecule so that it competes with the carrier molecule for binding to the hydrophilic molecule, or displaces the hydrophilic molecule from the carrier molecule. The change in transport of ions across the membrane can be detected by measuring for example the effect of the ion on the transmembrane electrochemical gradient (membrane potential, pH gradient using reagents such as dyes which accumulate and/or change their optical properties, such as fluorescent membrane probes), the interaction of the ion with a chromophore contained in the signal generating reagents, or by the activation of an enzyme by the transported ion.

Another range of molecules, typically peptides, allow the selective permeabilization of membranes to small molecules such as enzyme substrates. A typical peptide of this type is the peptide "mini-GALA" of structure LAEALAEALEALAA (SEQ ID NO:1), "GALA" (SEQ ID NO:2) of structure WEAALAEALAEALAEHLAEALAEALEALAA (SEQ ID NO:3), "KALA" (SEQ ID NO:4) of structure WEAKLAKALAKALAKHLAKALAKALKACEA (SEQ ID NO:5) and myristryl-mini-GALA. Other examples include melittin peptides and derivatives and variants thereof which have membrane permeabilising properties, such as those illustrated hereinafter. These peptides permeabilise the membrane to small molecules while preventing passage of larger molecules such as enzyme signal generating reagents and the signal agents produced thereby. The activity of the peptides may be blocked in the presence of a sensing reagent such as an antibody. However, if the antibody is specific for a particular analyte, it may be removed by said analyte, thereby allowing the peptide to exert its permeabilising effect so as to allow passage of the signal activation agents for example the enzyme substrates to pass into the containment means. The complex of the peptide and the sensing agent may be present in the lipid layer so that removal of the sensing agent has a direct effect on the surface of the layer. Alternatively, the peptide-sensing agent complex may be present in the surrounding solution with the sensing agent blocking the efficacy of the peptide. Removal of the sensing agent by interaction of the analyte will therefore free the peptide and allow it to exert its permeabilising effect on a liposome into which it then comes in contact.

In a modification of this approach, use may be made of signalling peptides, such as (FITC)-MLSLRQSIRFFKPATRTLCSSRYLL (SEQ ID NO:6) (P25) and (FITC)-MLSLRQSIRFFKPSTRTLCSSRYLLQQKPVVKTA (SEQ ID NO:7)-amide (P34), which insert themselves into a membrane and appear at the contained side. This can be demonstrated using fluorescent probe methods. Such peptides can be used to transport signal activation agents such as enzyme co-factors, metal ion complexes with catalytic activity (e.g. porphyrins) or even large hydrophilic structures such as soluble enzymes across the membrane, once a sensing or blocking reagent has been removed by reaction with the analyte. The said blocking agent may be displaced by reaction with the analyte or the analyte may compete for binding with the blocking agent. In either case, the amount of transport across the surface of the particle is related, typically proportionally, to the analyte.

Chemically modified forms of the signal peptides (e.g., P25) can insert into liposome-contained protease (e.g., trypsin) to produce a contained reaction. Specific fluorogenic substrates for proteases are well known (e.g., umbelliferone fluorescence on cleavage of the peptide) or can be simply detected by co-containment of pH sensitive fluorophores. Such forms may be used in the present invention.

For example, the leader sequence P-25 can be synthesised with a new N terminal amino acid linked to the remaining peptide by an ester linkage. Insertion of this N terminal group, guided for example by a reagent such as cardiolipin, results in the hydrolysis of the ester and a change in the fluorescence of the particular liposmes with which the peptide interacts. Selection of the nature of the amino acid allows a variety of proteases specific for that amino acid to be used.

Suitable signal generating means include those which are well known to those in the art and may comprise any of the signal or label generating reagents known for example in the field of immunoassays. For example, signal may be produced as a result of an enzyme reaction, which may be catalysed by a cofactor.

Signal generating agents may comprise agents or reagents which are capable of generating a light signal such as fluorescent dyes or luminescent enzyme systems like the luciferin/luciferase system. Alternatively, any of the other enzymatic detection systems such as the alkaline phosphatase reaction can be used. An example of an non-enzyme catalysed signal reaction would be the detection of lipid peroxidation from organic peroxides, which is catalysed by porphryins.

Rather than containing active enzyme, nanospheres of inactive enzyme can be produced, whose reactivation can be triggered by peptides. Inactive enzyme can be produced by co-containment of inhibitors and enzyme. Most competitive and many non-competitive inhibition of enzymes can be reversed by removal or dilution of the inhibitor. It will be understood that the means described for triggering entry of substrate can also be used to allow inhibitors to escape the nanosphere. Many enzymes, including but not restricted to oxidoreductases, require co-factors in order to operate. Such co-factors may be introduced by peptides forming channels or pores (allowing ingress or egress of other similar molecules) or via their specific insertion when attached to the above peptides (not allowing transport of other similar molecules) Some co-factors are normally tightly associated with the enzyme. The removal of such co-factors produces apoenzyme. Liposome-contained apoenzyme co-factors required by enzymes can be coupled to such peptides so that they are reconstituted with the enzyme. A typical example is the removal of the flavine adenine dinucleotide (FAD) co-factor from glucose oxidase to produce apo-glucose oxidase (Methods in Enzymology Vol. 92 Part E pages 413–417). FAD cofactor can be coupled to such peptides (e.g. by carbodiimide coupling to $N^6$ (2-aminoethyl)-FAD. Glucose oxidase can be incorporated into liposomes by the procedures described herein for alkaline phosphatase Alternatively, catalytic activity may be transported into the containment means. For example, the biological function of signal peptides is to transport polypeptides and proteins through membranes. Indeed, the P25/34 signal peptide structure described above are responsible for inserting cytochrome oxidase through membranes. Such peptides can also be used to insert other non-enzymic catalytic activities through membranes. Inorganic or organic catalytic structures can be attached to peptides to introduce and contain the activity in nanospheres and liposomes. The reaction catalysed may require energy, which can be provided in the form of light absorbed by the catalytic centre (photo-catalysis) or in the form of heat, which may also be provided local to the contained reaction by absorption of light, other electromagnetic or ultrasonic radiation. The use of externally applied energy provides additional means of triggering the contained reaction. Other catalytic centres do not require energy. Radical reactions catalysed by haem are a typical example. For example, haem catalysed peroxidation of lipids can be achieved.

Haem groups catalyse a radical mediated chain reaction which leads to lipid peroxidation. Because of the chain reactions involved, very small concentrations of haem cause significant peroxidation. The lipid peroxidation has been conveniently demonstrated by monitoring the change in permeability of the lipid membrane using fluorescent dyes (as before), but the radicals could also be captured in other reactions.

The applicants have found a new signalling system which is particularly useful in the context of the present invention. While many dyes form coloured complexes with metal ions, few such complexes are fluorescent. Such dyes may not be retained following triggering of the reaction and their fluorescence may be self-quenched at useful concentrations. Further, metal ions are a well known means of quenching fluorescence.

It was found however, that interaction of certain dyes, such as ELF-97 (Molecular Probes Inc. USA—see "Handbook of Fluorescent Probes and Research Chemicals" by Richard Haugland, $6^{th}$ Ed. 1996) with cobalt ions induced fluorescence and shifted the fluorescence of the dye to the red end of the spectrum. This can be useful in the context of the present invention where interaction may be allowed as a result of the interaction of the analyte.

Furthermore, it was found that alkaline phosphatase may at certain pH values, act as a catalyst for certain dye substrate reactions, in particular the ELF-97 substrate reaction. Since this pH is of the same order as that at which the GALA peptide is active, this can form a preferred system for use in the invention.

Because, in accordance with the invention, signal generation takes place within an enclosed containment means, non-specific signal from the sample may be minimised by adding signal quencher reagents to the sample. Suitable quenching reagents will depend upon the nature of any signal generating means present in the sample. However, in a finding of the present inventors, para-nitrophenyl phosphate (PNP) a substrate used in a calorimetric assay, was found to quench signal from the fluorescent dye ELF-97.

In a preferred embodiment, activation of the signal generation means is triggered by a sequence of more than one event. In particular, the interaction between the analyte and the element (sensing element) suitably depends upon a separate "arming" event or reaction before the interaction can take place. For example, where the interaction involves a carrier or permeabilisation peptide such as alamethicin or GALA (SEQ ID NO:2), the "arming" event or reaction may comprise the adjustment of the pH of the assay medium in order to ensure that the peptide is active. The GALA (SEQ ID NO:2) peptide (WEAALAEALAEALAEHLAEALAEALEALAA (SEQ ID NO:3)) demonstrates insignificant triggering at neutral/alkaline pHs and triggering at lower pHs. The alternative KALA (SEQ ID NO:4) peptide (WEAKLAKALAKALAKHLAKALAKALKACEA (SEQ ID NO:5)) shows the reverse of no triggering at acidic pHs and triggering at neutral/alkaline pHs. This activity is retained even when a hapten is attached to the N terminus of the peptide.

Alternative methods of arming may be achieved by photoactivation of the peptides by conventional methods. For instance, a photoinduced conformational change can be introduced into the peptide structure (e.g. cis to trans conformation of stilbenes) to render the peptides active, or the photocleavage of a masking group.

The use of a separate arming event or reaction ensures that the level of non-specific reactions is minimised and therefore the level of background signal, from reactions not involving the analyte is reduced. This allows increased levels of sensitivity of the assay since although, in general, a signal as a result of an analyte would be expected to increase at a greater rate than that of the background signal, the level of the background signal can be the limiting factor in determining the lower limits of sensitivity of an assay.

In one embodiment, triggering of catalytic activity inside the nanospheres (FIG. 3) can be achieved according to this invention. The use of peptides specifically to reactivate inactive enzyme, to insert substrate or catalytic activity into a containment means has been investigated and is reported hereinafter.

Suitably the containment means are concentrated or separated from the assay medium before the signal is detected. For example, containment means may be concentrated by techniques such as sedimentation or aggregation using a suitable aggregating protein such as avidin. Centrifugation may also be employed where the containment means are of a suitable size.

Signals generated in accordance with the method of the invention may be detected using a variety of techniques. These include physical means such as optical detection methods (e.g. methods which detect absorption, fluorescence, fluorescence polarisation, time resolved fluorescence, chemiluminescence, bioluminescence, refractive index, evanescent waves, surface plasmon resonance, resonant mirror, Raman, light scattering, photoacoustic or photothermal spectroscopies), electrochemical detections methods (e.g. amperometric, potentiometric, conductimetric or dielectric detection methods) or electromechanical methods (e.g. gravimetric, surface acoustic wave, Love plate, or acoustic wave propagation methods). Of these, surface plasmon resonance detection may be particularly suitable.

Other techniques which may be used are those which detect individual particles by single particle detection methods,(e.g. Coulter Counting, flow cytometry) or by scanning microscopies (e.g. confocal scanning microscopy, scanning near field optical microscopy, scanning tunnelling microscopy, atomic force microscopy, scanning electrochemical and acoustic microscopies). Of these, flow cytometry may be particularly useful in the context of the present invention.

The fact that the signal is generated within a containment means is conducive to the use of single particle detection methods and in particular microscopic detection methods such as Coulter counters, flow cytometers, scanning microscopes or other sensors of similar dimensions. At present, the detection of many conventional fluorophores (e.g. Calcein, Fluorescein and Rhodamine) using these single particle detectors has proved difficult because the fluroescence of these dyes self-quench at desirable concentrations for detections. Using the method of the invention, these problems may be overcome. The accumulation of highly fluorescent deposits of the ELF-97 product in particular but also other excimer and exiplex fluorescent dyes in the containment means of the invention means that detection is now possible.

It is possible to detect and/or count single entities (i.e. a containment means in which the signal generating reagents have been activated). Accurate measurements of from $10^2$ to $10^4$ such entities can be readily achieved, although measurement of from 1 to $10^2$ entities can be effected. As can be seen, this can equate to the presence of only a very few analyte molecules for example from 1 to $10^2$ where the entity requires only a interaction with a single analyte to activate the signal generating means.

Single particle detection has been carried out as illustrated hereinafter using a modified Coulter Epics 5 cell sorter operating as a flow cytometer. This instrument was designed for operation on cells of size 1–100 microns. An instrument produced for operation in the 50–250 nm range is preferred in that it will allow lower noise and higher sensitivity allowing better discriminations between the water, background and test sample distributions as detailed in examples 24–26 below.

The Epics system is based on analogue detection using photon multiplier tubes (PMTs) with variable gain voltage and followed by post detection amplification. PMT's operate with optimum signal to noise at a single gain voltage. In the Epics system the discriminator followed the amplifiers. The Epics system operated using analogue signals, but higher signal to noise may be achieved using photon counting detectors. It is also preferred that where the PMT's are photon counting and the gain voltage is fixed, the comparater is placed immediately following the PMT's and has a set value.

The Epics system uses a jet of fluid through air. This may cause significant background noise through scatter but the effect may be reduced by the use of a square walled flow cell. The analogue to digital converters (A/D) of the Epics system operated from a voltage of zero, where a very high gain is used to increase the distribution spacing the initial channels of the A/D are unused and the sensitivity of the instrument is decreased. A higher signal to noise may be achieved if the zero channel of the A/D may be set to equal the signal generated by a specific sample thus allowing a large increase in the number of A/D channels between size distributions.

More recent circuits than those of the Epics system may also operate with a higher signal to noise, higher bandwidth and reduced frequency response thus the instrument could be produced giving a higher signal to noise and increased distribution spacing.

As used herein, all measurements were taken using distilled double 0.22 micron filtered water, it is known in the art that higher grade filtering is available. All liposome suspensions were produced in standard buffers, it is known in the art that any of these contain significant background fluorescence and specialised buffers may be produced with a lower fluorescence background. Buffers and sheaf fluid may be degassed, or gassed with a specific gas, so to reduce background fluorescence. Buffers and sheaf fluid may or may not contain any of the additives which are known in the art to reduce background fluorescence.

Although the standard Epics system collects only a small percentage of the emitted light, the use of different lens combinations, mirrors and specialised flow cells may allow more light to be collected from the sample increasing the signal to noise ratio. Where the instrument uses a single laser line and that line pumps fluorescence, the scatter signal will be minimal as absorption of the light has occurred. The maximum fluorescence signal from a sample is fixed whereas the scatter signal may be increased, by increase of optical power.

An instrument may be produced using two or more excitation wavelengths. The first excitation wavelength designed to pump the fluorescent product, the second excitation wavelength to be outside the window of both the fluorescence and excitation and emission and used to produce a scatter signal. Preferably the scatter excitation will be a wavelength that is shorter than the excitation window thus increasing scattering.

Suitably the intensity of the fluorescence excitation beam will be of a magnitude just below that which would cause maximum fluorescence excitation such that scatter from impurities is reduced. Preferably the scatter excitation beam will be variable such that the excitation may be increased to clearly see the sample distributions whilst not being as high as to increase noise due to impurity scattering.

Very high laser powers may be used and these may be achieved using pulsed laser operation including, but not exclusive too Q-switching, modelocking and cavity dumping. Repetition rates of 100s of Mhz may be achieved and that laser pulses may be of the order of 100 femto seconds.

Time correlated single photon counting techniques can be used to further increase signal to noise of fluorescent measurement. Preferably the photon count from the both the fluorescence and scatter detectors will each be discriminated against two discrimination levels such that signals that are either two small or two large, to have been produced by the active species/particle, are ignored. Preferably the detectors will work as a logical AND combination reducing noise further. Preferably the fluorophore is chosen such that Raman scattering of the excitation beam by from the sample does not generate a signal in the emission area of the fluorophore.

Furthermore, such methods of the invention may be used in order to detect several analytes simultaneously. By providing a mixture of containment means such as liposomes which contain different signal generating agents and which are triggered by the presence of different analytes, the presence of more than one analyte may be detected.

It is an important advantage of some embodiments of the invention that a reaction of only one or a very few analyte molecules can give rise to a visible signal which may be counted indvidually using the techniques outlined above. The reason for this is that the signal generating agents are concentrated within a small particle, and not diffused throughout a sample volume. Furthermore, a definate signal, (the particles are either triggered or not) may result from the presence of one or very few analyte molecules.

This means that the levels of detection achievable with the method of the present invention is lower than with previously available methods. In order to achieve such high levels of sensitivity, the analysis of a large number of containment means (e.g. $10^6$ or more) can be undertaken to ensure that those few which have been activated are detected.

Such highly sensitive detection methods can be used for example in detecting trace amounts of substances such as chemical or biological agents in samples or even in the air. Examples of chemicals which may be detected in this way include explosives, microorganisms and their products such as toxins, chemical warfare agents, pesticides, hormones or drugs.

Some embodiments of the invention may be considered to be more tolerant of variable levels of background signal, particuarly where the level of specific signal above background is only used to discriminate between counting of reacted versus non-reacted entities. In practice, it is possible, using the method of the invention, to combine counting of reacted entities and analysis of the quantity of signal in each reacted particle as an assay means. The quantity of signal in the reacted entities may be used to discriminate between specific reaction and non-specific reactions. Non-specific reacted entities may be distinguished by their different characteristics (e.g. optical) and/or simply the quantity of the signal detected in each entity. Non-specifically reacted entities may thereby be discarded from the counted signal. Accordingly, the counted signal will be that above a predetermined threshold or within a specific characteristic (e.g. optical) in each reacted entity analysed.

A containment means for use in a method as described above form a further aspect of the invention.

Yet a further aspect of the invention comprises a kit for detecting the presence of an analyte, said kit comprising a containment means enclosing signal generating reagents and an element which interacts specifically with said analyte so as to allow the activation of the signal generating reagents within the containment means.

As has been mentioned above, and is exemplified below, the applicants have found that the fluorescent output of a product is increased, and the output wavelength varied, by incubation of the substrate with a range of materials including cobalt ions as would not be foreseen in the art. In addition the relative quantities of conventional and incubated product that is used can affect the rate of the product reaction, which in itself, provides a signalling mechanism, particularly in the context of the process described above.

Also the incubation effect has been shown to increase the rate of product formation and modify the substrate in such a manner as to remain a substrate to an enzyme at pH ranges where the enzyme would not normally be active with the substrate.

That a fluorescent material may have its energy level increased by the addition of cobalt ions is quite unexpected in the art. Furthermore, it is surprising that a fluorescent material may have its energy levels shifted, thus causing an increase in the emitted intensity, by the addition of cobalt ions.

It was not foreseen that the fluorescent output intensity and/or wavelength of a product would be increased by means of incubation of materials such as metal ions with the substrate prior to product formation. It is surprising that the variation as described above is not reversible in that the variation only occurs substantially if the materials are added to the substrate and incubated. The shift does not occur if the same materials are added to the formed product that has been given sufficient time to stabilise.

The ELF reaction was found not to be stable immediately it reached its maximum fluorescent intensity but required up to ten hours to become irreversible in terms of the "incubation reaction". The incubation effect may increase the rate of product formation. Furthermore, it may be employed in order to allow enzymes to operate outside the pH range that is possible with un-incubated substrate.

Where the signal (including but not exclusive to fluorescence) has a characteristic lifetime, the incubation effect will probably affect the lifetime of the signal.

All of these features give rise to potential assay applications.

Thus in a further aspect, the invention provides a method for modifying the signal from a signal generating reagent which generates said signal on reaction with a chemical activator, said method comprising incubating said signal reagent prior to exposure to a chemical activator, either with an ion, a surfactant and/or in a buffer at a p.H. which results in modification of a property of said signal.

Examples of such properties which may be modified include the wavelength of a signal emitted or the speed of the product formation, although other properties such as density, refractive index, and impedance may also be affected and these variations may also be measurable, for example using bulk sample analysis or single particle detection.

The signal generating reagent is suitably a dye, in particular a fluorescent dye such as ELF, an ELF substrate or a derivative or modified form thereof.

As well as cobalt ions, suitable modifying chemicals may be surfactants, in particular detergents such as Triton-X which may form a component of a buffer which are provided at an appropriate pH value.

The incubation effect can be utilised in the detection of modifying chemicals. Thus, a further aspect of the invention provides a method for detecting the presence of a chemical which modifies the signal from a signal generating reagent said method comprising contacting said signal generating reagent with a sample suspected of containing said chemical and subsequently with a chemical activator, and detecting the signal therefrom.

The incubation effects noted suggest that there may be binding of the modifying chemical to the substrate which produces a reduction in self-quenching. Such variation may cause a change in other measurable parameters such as density, refractive index and impedance and these variations may be measured by other suitable means that are known in the art in both bulk measurement and single particle detection Many of the assay reactions show a significant time dependence over periods of hours (i.e. the reaction rate varies with time) and this is generally dependent on the level of analyte. Thus the measurement of the assay value or rate is preferably carried out at a predetermined time from the start of the reaction. A background signal measurement sample is suitably also measured simultaneously.

The effect of incubation time of the substrate and the irreversible nature of the reaction allows the dependence to be used as intrinsic measure of the rate of the reaction. This allows measurements to be made at any time during the reaction, and the results may be calibrated appropriately.

The amount of wavelength shift being an intrinsic measure of the reaction rates. It is further claimed that since this effectively integrates the rate over the entire experiment that it is possible to obtain a higher sensitivity at this point.

The invention is ideally suited to assays but may be used simply to produce novel markers. The term "incubation" is herein used to describe the process of contacting a substrate and a treatment additive for an appropriate period of time. This time period may vary between no preincubation as such and incubation over several days depending upon the precise nature of the reagents involved and the modifying effect required.

BRIEF DESCRIPTION OF THE DRAWINGS

The invention will now be particularly described by way of example with reference to the accompanying diagrammatic drawings in which:

FIG. 1 is a diagrammatic drawing illustrating a reaction which forms an embodiment of the invention;

FIG. 2 is a diagrammatic drawing illustrating a reaction which forms a different embodiment of the invention;

Figure 3:
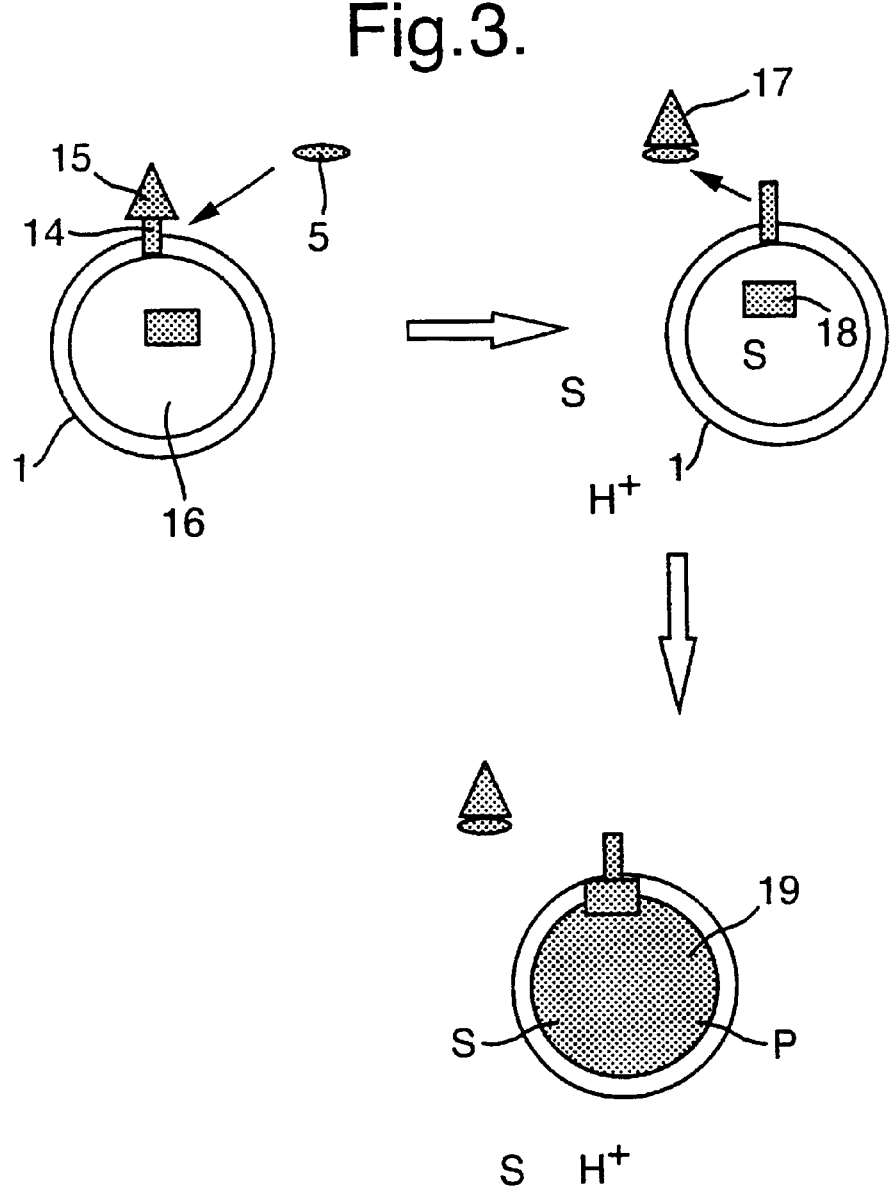
FIG. 3 is a diagrammatic drawing illustrating a reaction which forms yet a further embodiment of the invention.

In the embodiment of FIG. 1, a particulate containment means such as a liposome (1) contains signal generating agents (2) which generate signal in response to the presence of an ion such as $H^+$. Suitable agents (2) are therefore pyranine. All channels (3) for the ion (3) in the surface of the liposome (1) are blocked by means of an antibody (4). The antibody is also specific for an analyte (5).

When the antibody (4) comes into contact with an analyte molecule (5), it preferentially binds to it, forming a complex (6) which may or may not separate from the surface. The ion channel is thereby opened (7) allowing ingress of ion into the liposome (1). On contact with the ion, the signal generating agents are activated and a signal (8) can be recorded.

Many specific examples of this type of ion-triggered and contained fluorescence can be envisaged. Two such examples are given below as Examples 1 and 2 respectively. Example 1 illustrates the use of fluorescent monitoring methods for ion gradients here by collapsing a pH gradient. A range of other such ion gradients could be collapsed. The second demonstrates a novel discovery of a fluorescent metal ion complex suited to the implementation of this invention.

In the embodiment of FIG. 2, activation of the signal generating agents (2) requires a sequence of two reactions in order to produce the signal. In this case, the containment means or membrane (1) includes channel forming peptides (9) to which haptens to the analyte are bound. Transport activity of the peptide (9) is blocked by the binding of an antibody (10).

The antibody (10) is however specific for analyte (5) on protonation forming a complex (12) which separates from the containment means (1) so opening the channel. In this case therefore, the switching mechanism requires both antibody and protonation reactions in order to be activated. This provides higher fidelity and ensures lower background permeability of substrate.

Opening of the channel peptide (9) allows ingress of an enzyme substrate (S) which acts on enzyme (11) within the signal generating means in order to allow the signal to develop.

In addition to the above approaches of forming channels, pores or changing the permeability of the membrane of the liposome-contained reagents to develop signal within the nanosphere, by bringing free substrate in the sample into contact with contained enzyme or by collapsing ion gradients, the approach of triggering catalytic activity inside the nanospheres can be achieved according to this invention. Approaches have been investigated using peptides specifically to reactivate inactive enzyme, to insert substrate or catalytic activity.

In yet a further embodiment (FIG. 3), activation requires a combination of antibody, protonation and apoenzyme reactions. In this case, hapten and co-factor are attached to the signal peptide (14) such that antibody (15) binding prevents entry of the co-factor into the containment means (1) and binding of the apoenzyme (18).

The binding of analyte to blocking or competiting antibody allows the signal peptide-hapten-cofactor conjugate to enter the liposome. Reconstitution of the cofactor and apoenzyme activates the enzyme giving rise to the signal.

The following examples illustrate the invention. The examples given below demonstrate liposome-contained reactions which can be triggered by peptides and coupled to established biodetection reactions in the sample and/or associated with the surface of the liposome or nanosphere.

The contained reaction of the ELF 97 has been found to be particularly useful, because the highly fluorescent product is easily contained, even when the liposome membrane is rendered permeable to the substrate. Sedimentation investigations (e.g. using protoamine or avidin to agglutinate the particles) indicated that the reaction was particle localised.

EXAMPLE 1

Liposome Contained Pyranine Fluorescence Following Ion Transport Mediated by 41mer Peptide and Ionophores Liposomes contained 1 mM pyranine in 1 mM Bis-Tris and 50 mM $K_2SO_4$ pH 7.5 were added with approx. 25 fold dilution (e.g., 100 µL into 2.4 mL) to buffer comprising 1 mM Bis-Tris and 50 mM $K_2SO_4$ pH 7.0 to form a pH gradient. Liposomes were prepared by smearing 120 µL of soyabean lecithin (Sigma Type IV-S) at a concentration of 100 mg/mL in chlorform around a round-bottomed flask and drying under a stream of argon gas (5–10 min). The above pyranine solution (1.87 ml) was added to the dried lecithin under argon gas, shaken for 2 to 3 hours, subjected to five rapid freeze-thaw cycles (freezing under liquid nitrogen followed by thawing under a stream of hot tap water) and then extruded through a sandwich of two 100 nm pore size Nucleopore membrane filters. Non-contained pyranine was removed by gel filtration through a PD-10 column eluted with 1 mM Bis-Tris and 50 mM $K_2SO_4$ pH 7.5. A liposome-permeabilising 41mer peptide, a proton ionophore (CCCP) and a potassium ion ionophore (valinomycin) were added at concentrations of 2.2 µM, 1.6 µM and 1.6 µM (respectively). The 41mer peptide was of sequence SEAGGSSSFASNNIY-GIGAVLKVLTTGLPALISWIKRKRQQ (SEQ ID NO:8)-AMIDE.

Figure 4:
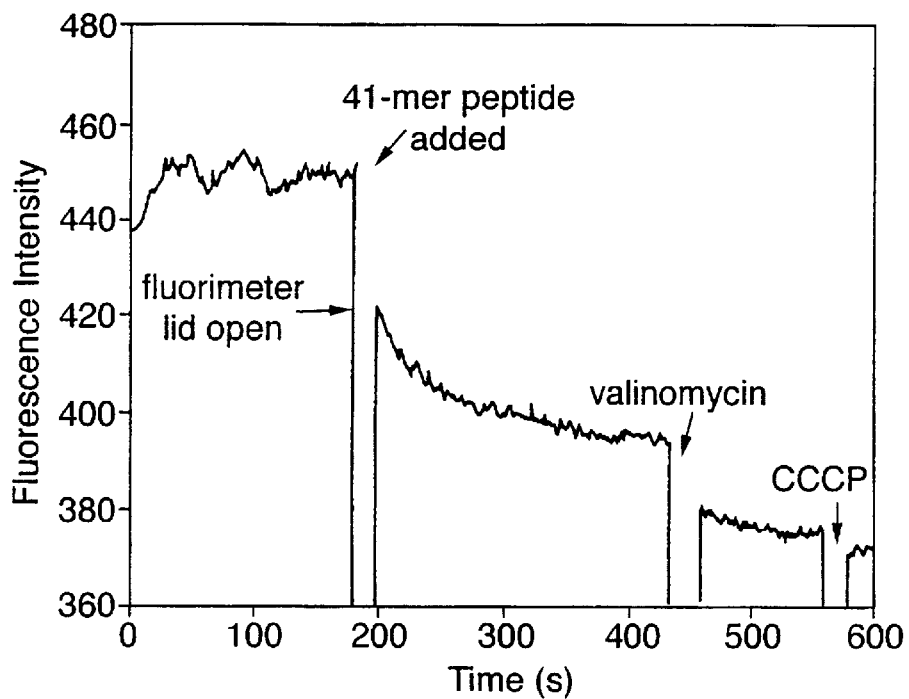
FIG. 4 shows the change in fluorescence noted when liposomes containing pyanine are subjected to a collapse in pH gradient.

Fluroscence was monitored using a spectrofluorimeter. A detectable change in fluorescence was noted when the 41mer peptide associates with the liposome membrane and that further treatment with ionophores (valinomycin+CCCP) to collapse the residual pH gradient produced a small further change (FIG. 4).

Figure 5:
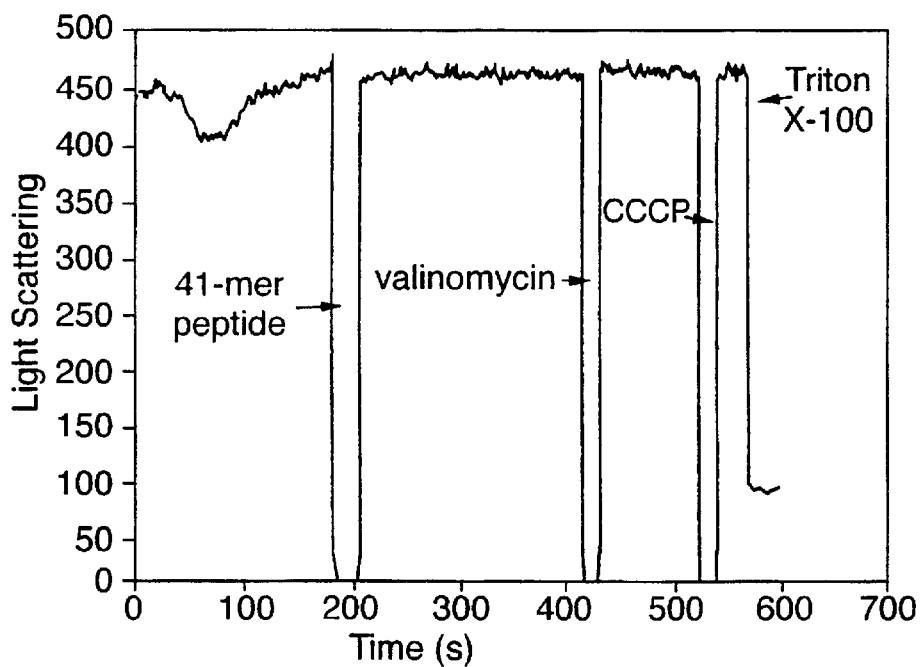
FIG. 5 shows the results of light scattering monitoring during the collapse of the pH gradient, indicative of the integrity of the liposomes throughout this process.

However, at the same time, an insignificant change in light scattering on addition of the 41mer peptide and ionophores was demonstrated (FIG. 5), indicating that the liposomes remained substantially intact and the pyranine remained contained, until treated with a detergent (Triton X-100), which control resulted in a substantial decrease in light scattering as the liposomes were dissolved.

The change in fluorescence may be monitored by a spectrofluorimeter (as above) but the difference between reacted and non-reacted liposome particles was sufficient to allow them to be discriminated by fluorescent single particle detection apparatus (in a similar fashion to later examples)

EXAMPLE 2

Cobalt Ion Induced Fluorescence

The fluorescent dye (ELF-97, Molecular Probes Inc.) is water soluble and non-fluorescent (at longer wavelengths) in the unreacted form and insoluble and fluorescent (at longer wavelengths) in the reacted form.

The fluorescence of ELF (10 µM) was monitored following the addition of 20 µL of cobalt chloride solution (2 mM). The red-shifted fluorescent emission of ELF progressively increased when exposed to cobalt ions.

The fluorescent complex formed by reaction of cobalt ions with the ELF dye has an identical excitation spectrum to that of the normal ELF product (produced by alkaline phosphatase). However, while the emission spectrum is substantially red-shifted like the normal enzyme produced insoluble product, its peak emission is at a slightly shorter wavelength.

The emission spectra of the cobalt complex with ELF (FIG. 6 trace a) is increased in magnitude and red shifted relative to the emission of the normal precipitate (trace b) produced by the reaction of ELF catalysed by alkaline phosphatase (see later). However, the excitation spectra (FIG. 7) showed no significant shift in peak positions.

This system may therefore be of use in particular in accordance with the invention. Exposure to cobalt ions, for example as a result of either the direct or indirect permeabilisation of a lipsome in the presence of an analyte can be detected by monitoring the red-shift in ELF fluorescence.

EXAMPLE 2a

Further Investigations Into Cobalt-induced Fluorescence Were Carried out

Unless otherwise stated, 4 µl of 10 uM ELF-97, 1.5 ml tris 10 mM buffer 7.1 pH and 10 ul of alkaline phosphatse liposomes were used in the experiment. Cobalt ions were supplied by a 2 mM cobalt chloride solution. The term ELF is used to denote ELF97 as supplied by Molecular probes.

Figure 6:
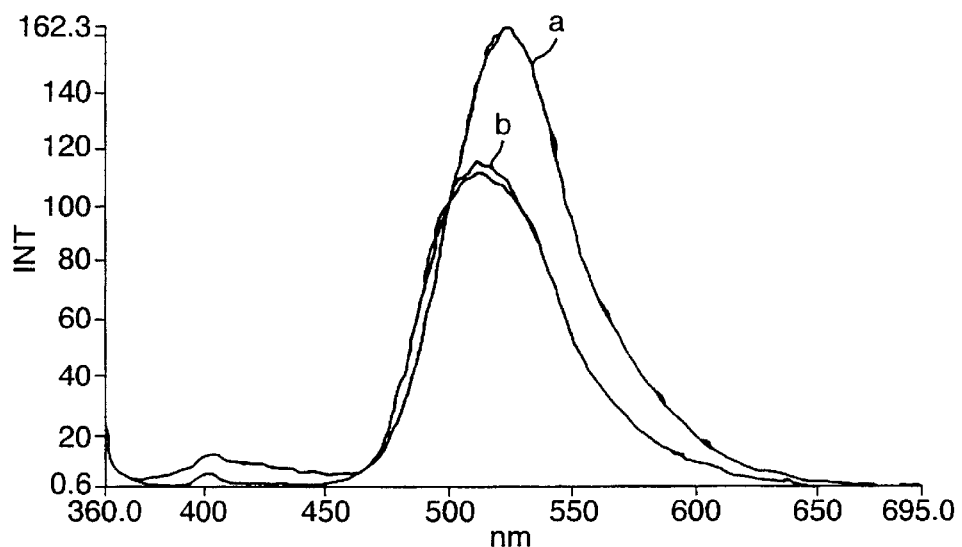
FIG. 6 shows the emission spectra of a fluorescent cobalt product.
Figure 7:
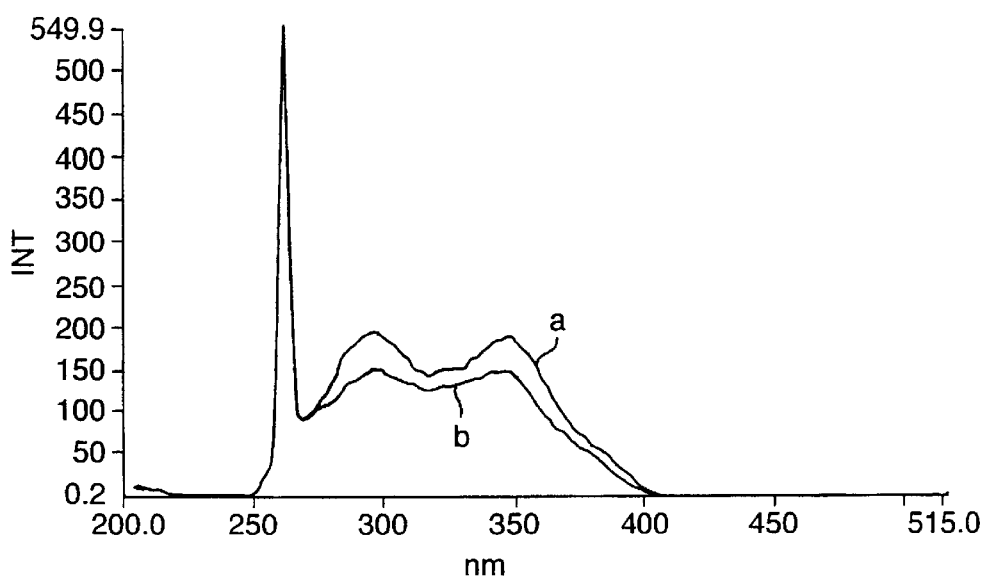
FIG. 7 shows the excitation spectra of the fluorescent cobalt complex.
Figure 8:
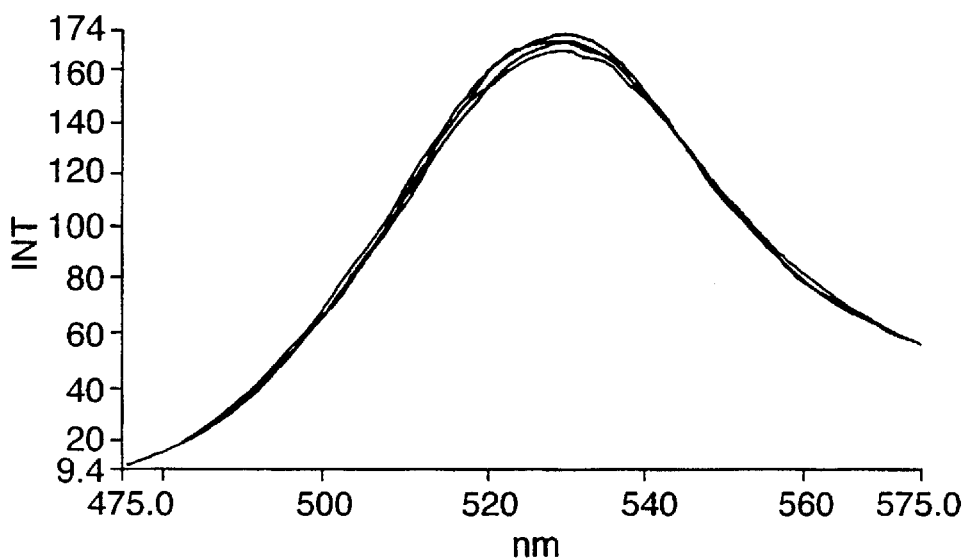
FIG. 8 shows the results of an experiment to demonstrate the stability of substrate-enzyme product in the presence of cobalt.

FIG. 6 shows the fluorescent output for elf precipitate and cobalt treated precipitate by the addition of 20 uL of cobalt solution which had been incubated for 1 hour. The trace of the sample incubated with cobalt is significantly higher and the excitation peak has moved of the order of 20 nm. The control trace (FIG. 7) shows there was no shift in the excitation peak although the cobalt sample may have been slightly more absorptive.

FIG. (8) shows that the normal product is stable in the presence of cobalt. 20 µl of cobalt was added to product that had been allowed to form over 15 hours, the sample was then measured 10,45,92 and 240 minutes after addition of cobalt and no change in the emission was noted. This indicates that the cobalt does not act on the product directly and that the conventional product reaction is irreversible in the presence of cobalt over periods of at least 4 hours. It has been shown that whilst the fluorescence magnitude of the normal product reaction may be stable within 1 hour the reaction is unfinished an that addition of cobalt at this time my cause cobalt-product to be generated

EXAMPLE 3

Enzyme Substrate Triggered Fluorescence

In this example, alkaline phosphatase was contained in liposomes and separated from its fluorogenic substrate (ELF-97) in the sample. On permeabilisation of the liposome membrane to the substrate, it was demonstrated that the fluorescent product produced was contained within the liposomes.

Calcein and alkaline phosphatase and blank liposomes were prepared by well established methods. Both biotinylated and normal (non-biotinylated) liposomes were made by normal extrusion methods. Typically, a phophatidylcholine (40 mg) cholesterol (11 mg) and dihexadecyl phosphate (2.8 mg) composition in 1:1 chloroform/methanol solution was prepared and, in the case of biotinylated liposomes, was also mixed with 302 µl volume of 0.5% (w/v) biotin-DPPE (biotinoyl dipalmitoyl phosphatidylethanolamine (Pierce) solution. The mixture was dried and typically hydrated with 3.75 ml of 10 mM Tris HCL pH 7.1 buffer containing 6.5 mg (10000 units) of alkaline phosphatase enzyme (Sigma) or 120 mM Calcein dye. The liposomes were made by extrusion through 400 nm followed by 200 nm polycarbonate filters. Purification of non-trapped enzyme was by gel filtration (Sepharose CL-6B, Pharmacia) column equilibrated with same buffer. Background enzyme activity was reduced further by treating the externally bound enzyme with immobilised trypsin. 100 mg of trypsin beads (Sigma) were added to 1 ml of the liposome prepartion and mixed on a mechanical roller for 11 hr, when the beads were removed by filtration.

EXAMPLE 3a

Centrifugation Studies

The following results illustrate the potential of a substrate channel approach by using liposomes as the containment means.

Figure 9:
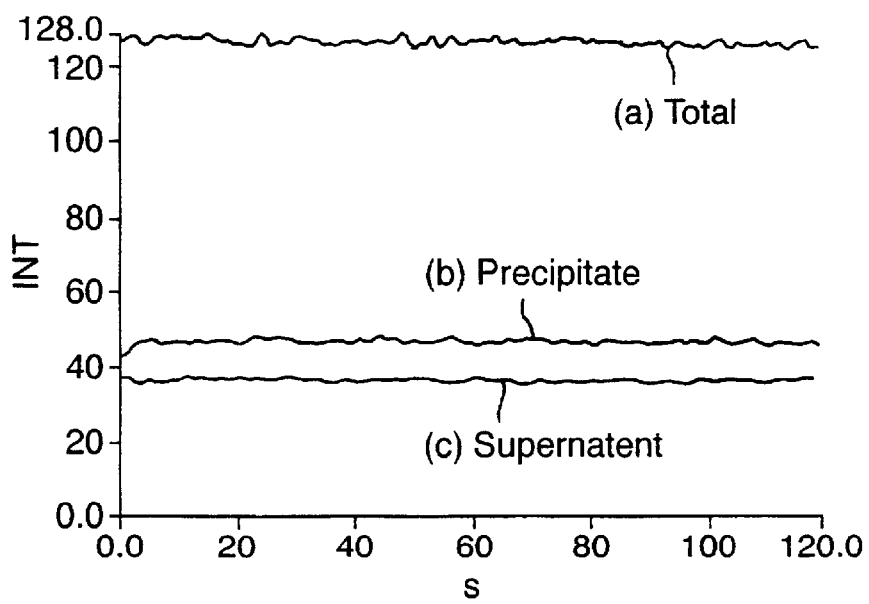
FIG. 9 illustrates the results of a centrifugation study to show formation of solid product.

As a control reaction, alkaline phosphatase present in 2 ml buffer of 10 mM Tris-HCl buffer pH 7 was incubated with 4 $\mu$l (5 mM) ELF substrate and the total signal was monitored (FIG. 9-trace a). The resulting product was centrifuged (at 13,000 g for 20 min) and the fluorescence recorded for the supernatant fraction containing colloidal and smaller complexes (trace c) and precipitate fraction following resuspension (trace b) in similar volumes. The excitation and emission wavelengths were 365 nm and 515 nm respectively.

These results indicate that the fluorescent ELF product was a fairly large complex, which would be too large to transport into liposomes. The fluorescent product formed by non-liposome contained alkaline phosphatase was water insoluble as compared to the substrate. Following reaction, the complexes formed produced excimer fluorescence (enhanced by close contact between the dye molecules facilitating the formation of excited dimers or excimers). The results shown in FIG. 9 indicate that some complexes aggregated to the size that they can be sedimented by low speed centrifugation, while other complexes were smaller.

Figure 10:
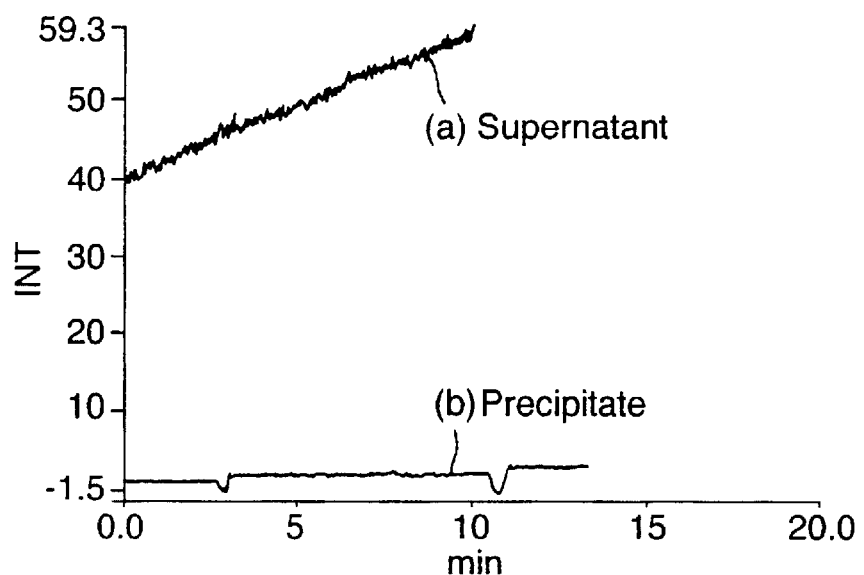
FIG. 10 illustrates the localisation of fluorescence with in liposomes.

Normal (non-biotinylated) alkaline phosphatase liposomes (10 $\mu$l) in 10 mM Tris-HCl buffer pH 7 and a 2 ml assay volume were triggered with 10 $\mu$g of the lipopeptide mini-myristylated-GALA (mini-m-GALA of structure: Myristic-LAEALAEALEALAA) to form the substrate channel. Following reaction of the ELF substrate similar low speed centrifugation (12,000 g for 20 min) studies were performed and the results are shown in FIG. 10.

This shows negligible fluorescence in the sedimented fraction on resuspension in a similar volume (trace b)) and virtually all the fluorescence now appears in the supernatant fraction (trace a), which continued to increase. This indicates that the fluorescent complexes were retained within the liposomes, which are too small to sediment on low speed centrifugation

EXAMPLE 4

Peptide Mediated Fluorescent Signal—Non-biotinylated Liposomes

The following experiment illustrates the potential for peptide mediated development of the fluorescent signal.

Figure 11:
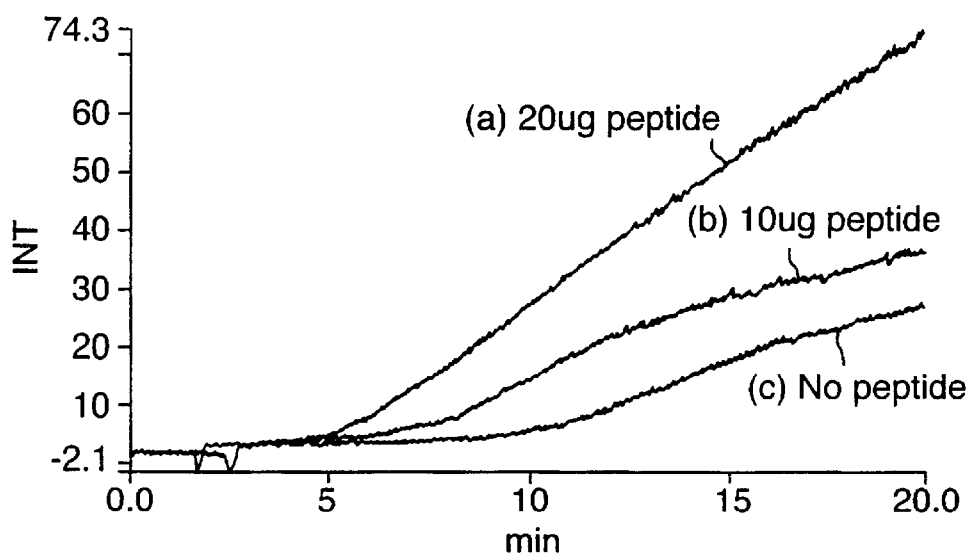
FIG. 11 is a graph illustrating the effect of channel forming peptides.

Conditions were as above (Example 3a): 10 $\mu$l of liposome containing alkaline phosphatase were added to 2.5 ml of buffer, and triggered with the quantities of the mini-m-GALA peptide in the presence of 4 $\mu$l of 5 mM ELF-97 substrate. The progress of the reaction was recorded for 20 minutes using a spectrofluorimeter (FIG. 11). On triggering with 10 $\mu$g of mini-m-GALA peptide, the product formation was enhanced (trace b), higher levels of peptide (20 $\mu$g) caused a more rapid signal development (trace a).

It is believed that this is partially due to release of alkaline phosphatase (by a 'lytic' effect in which the liposomes are broken open). The results shown in FIG. 11 show that at a level of 20 $\mu$g level, the peptide is appreciably 'lytic', while at the 10 $\mu$g level the peptide is not significantly 'lytic'. The non-specific signal noted in the control experiment (trace c) was believed to have arisen from a slight background (exterior) enzyme activity of the liposome preparation, and/or may involve slow entry of the ELF substrate, or its partition into the membrane.

EXAMPLE 5

Peptide Mediated Colorimetric Signal—Non-biotinylated Liposomes

Figure 12:
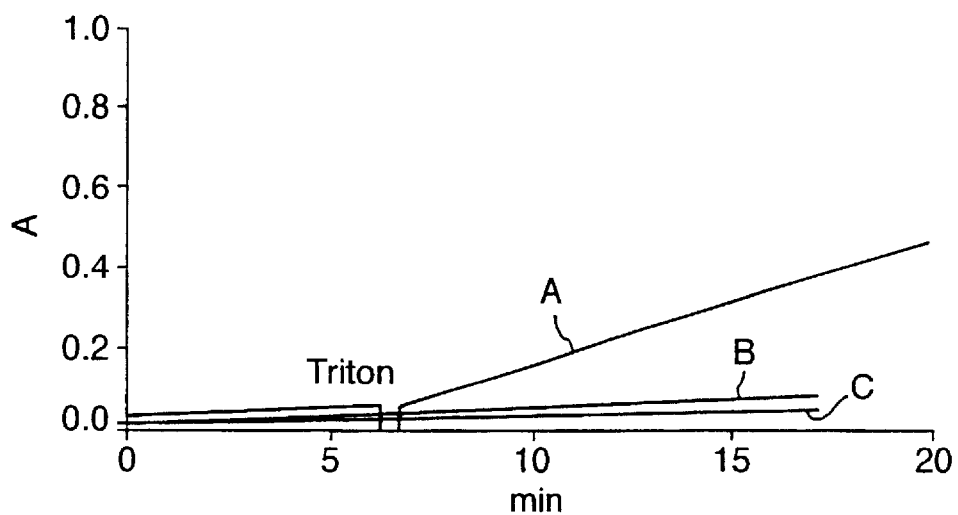
FIG. 12 shows the results of a colourimetric assay of alkaline phosphatase contained in liposomes.

In a parallel experiment using a colorimetric assay of the enzyme, an assay volume comprising 900 $\mu$L of 10 mM Tris-HCl buffer pH7, 10 $\mu$l liposomes and 100 $\mu$l of 1 mg/ml p-nitro phenyl phosphate substrate (PNP) was produced. The ELF substrate (4 $\mu$l of 5 mM) was added just prior to recording (FIG. 12) (trace c), while Triton was added to the control experiment as indicated (trace a). For the ELF product (trace b), the product was produced as in Example 3a and the PNP was added to 900 $\mu$l of the sample, which was then transferred to a spectrophotometer for assay. The absorbance was recorded continually at 405 nm wavelength.

Compared to the more sensitive ELF fluorimetric assay, the PNP colourimeteric assay showed low background activity in the presence of the ELF, which was higher in the presence of the ELF product than substrate.

EXAMPLE 6

Peptide Mediated Colorimetric Signal—Biotinylated Liposomes

Figure 13:
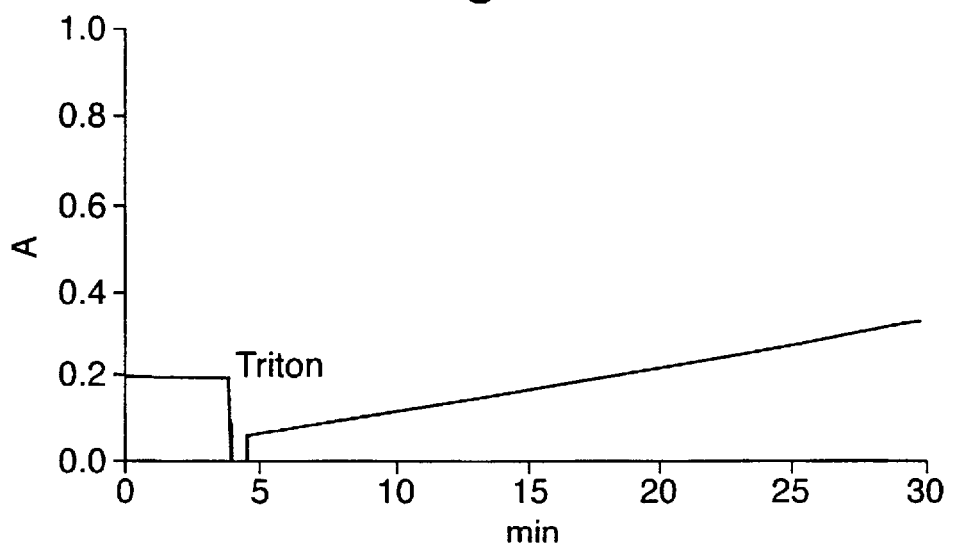
FIG. 13 shows the results of a colourimetric assay of biotinylated liposomes.

A colourimetric assay was performed in a manner similar to that of Example 5 using 900 $\mu$l of 10 mM Tris-HCl pH 7 buffer, 100 $\mu$l of 1 mg/ml p-nitrophenyl phosphate (PNP) substrate and 10 $\mu$l liposomes. The results are shown in FIG. 13. In the absence of Triton, there was no significant activity (left) while, on addition of Triton, activity appeared (right).

As there was almost no background enzyme activity, which could released on addition of Triton to lyse the liposomes, the biotinylated liposomes appeared to be more stable with no significant enzyme attachment to the exterior of the liposomes.

Biotinylated liposome contained alkaline phosphatase also demonstrated insignificant non-specific (untriggered) signal with the ELF-97 substrate.

Figure 14:
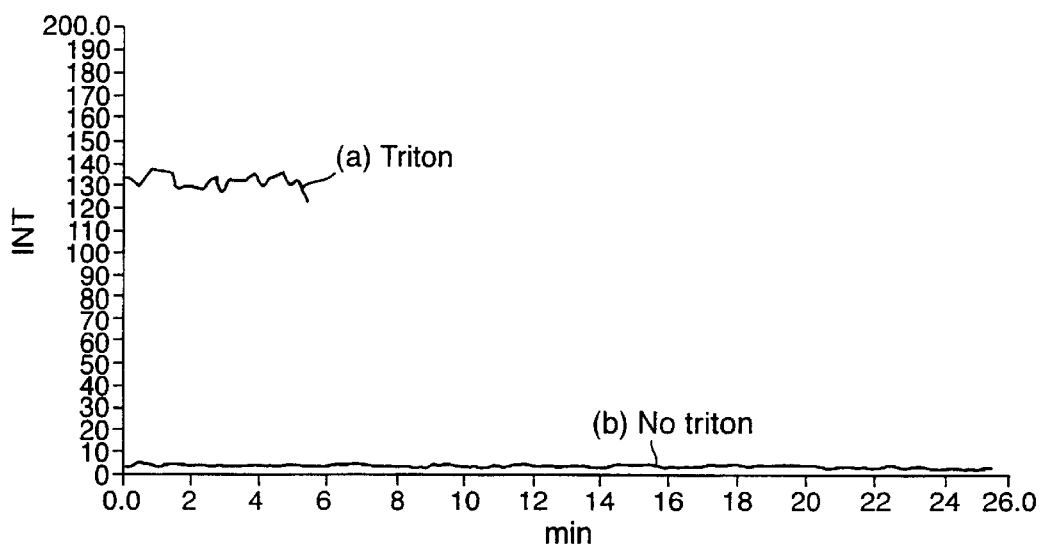
FIG. 14 shows a fluorimetric assay of biotinylated liposomes.

The assay conditions used were: 1 ml assay volume of 10 mM Tris-HCl buffer with 10 $\mu$l liposomes and 4 $\mu$l of 5 mM ELF-97 substrate. The signal generated was monitored and the results showed a virtually nil rate (FIG. 14 trace b). Triton was then added producing a large signal (trace a).

EXAMPLE 7

Figure 15:
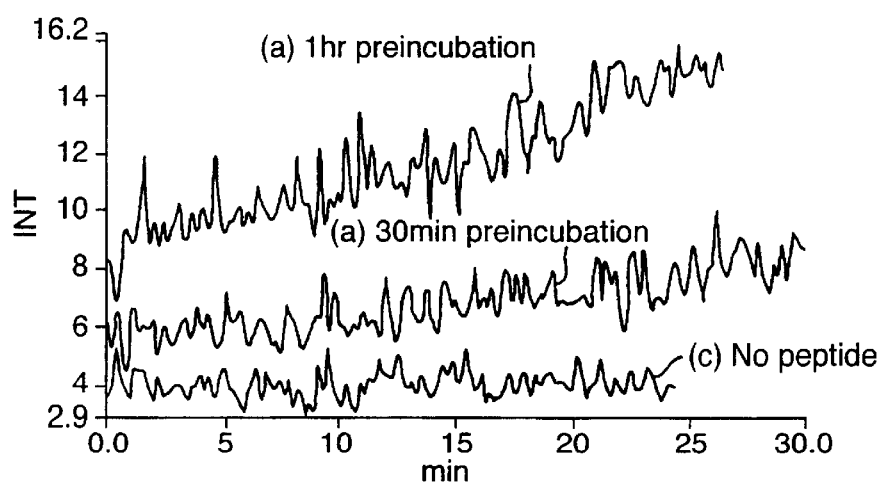
FIG. 15 illustrates the substrate channel formation with certain GALA peptides in biotinylated liposomes.

Substrate Channel Formation With Mini-myristic GALA Peptide and Biotinylated Liposomes Experimental conditions were the same as those used in Example 4 above for non-biotinylated liposomes. Biotinylated liposomes were triggered by peptide (10 $\mu$g) and the rate followed, shown in FIG. 15 for 30 minutes of treatment (trace b) and 60 minute of treatment (trace a), which can be compared to the control with no peptide, showing no significant activity (trace c).

In the case of biotinylated liposomes, while the non-specific signal development had now been removed, the rate of specific signal development was considerably slower than with non-biotinylated liposomes. This appeared to be consistent with the slower diffusion expected for the substrate via the peptide channel alone (i.e. previous data was for the peptide channel plus non-specific background).

EXAMPLE 8

Figure 16:
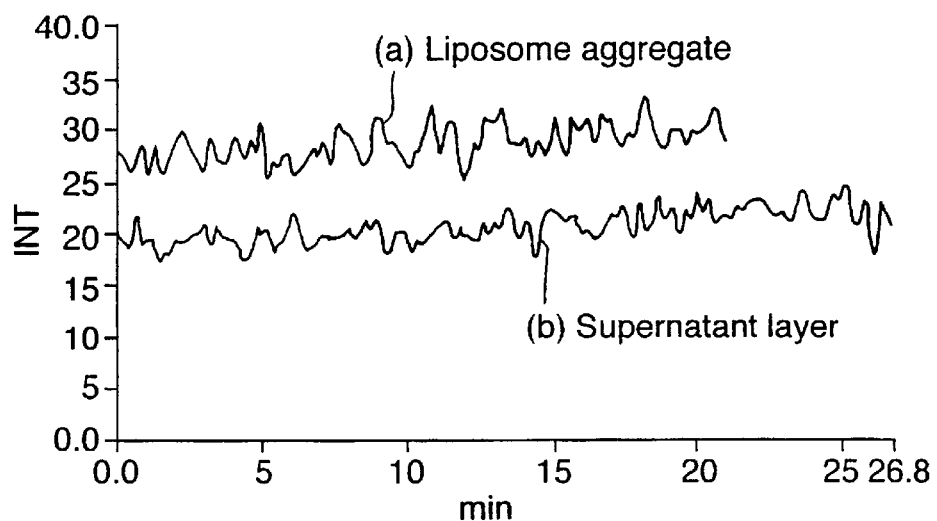
FIG. 16 illustrates signal localisation as a result of liposome aggregation.

Localisation of Signal by Liposome Aggregation 10 mM Tris-HCl buffer pH 7 (2 ml) containing 10 μl liposomes was treated with 4 μl of 5 mM ELF-97 substrate. The sample was incubated for 90 minutes, when avidin (4 μg) was added to cause aggregation of liposomes. The aggregated liposomes were sedimented (without centrifugation) and the upper clarified layer was removed to record fluorescence. Similarly the aggregated liposomes were resuspended and the signal recorded. The results are shown in FIG. 16.

As is clear, the signal was largely associated with liposomal fraction (trace a). The signal left behind in the supernatant layer (trace b) may be explained by incomplete aggregation as well as sedimentation, as centrifugation was not used here, lest this also sedimented any non-liposomal ELF product.

Clearly, biotinylated liposomal enzyme can be sedimented following aggregation of the liposomes by avidin.

EXAMPLE 9

Quenching of Non-specific Signal

It was noted during the performance of the examples given above, that p-nitro phenyl phosphate (PNP) substrate for the colourimetric assay was able to quench the fluorescence of ELF-97 product.

Figure 17:
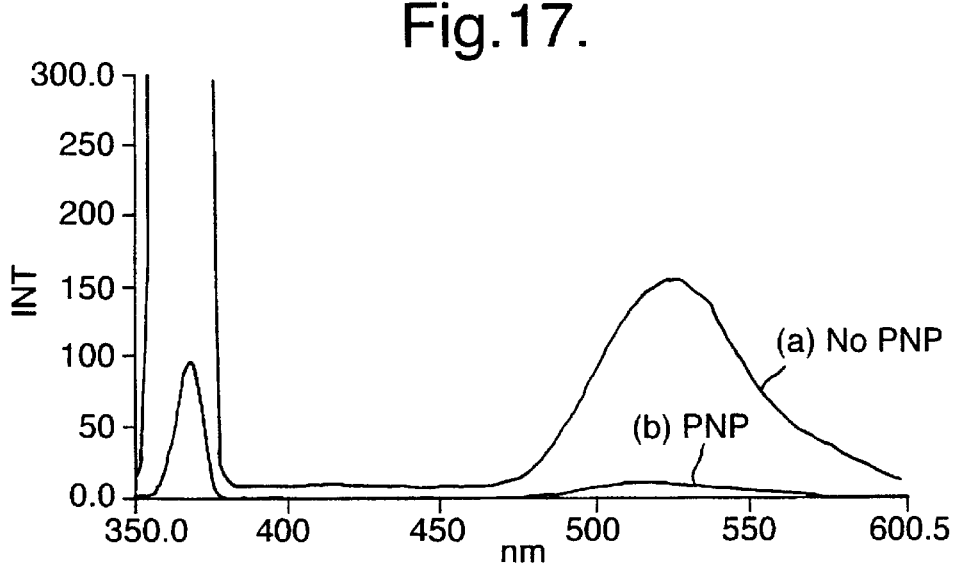
FIG. 17 illustrates the quenching effect of para-nitrophenyl phosphate on the fluorescence of ELF-97.

FIG. 17 shows (trace a) the emission spectrum of non-quenched product (0.9 ml Tris buffer pH 7, 4 μl of ELF-97 substrate, 10 μl liposomal alkaline phosphatase and 10 μl Triton). PNP (100 μg) was added to produce the quenched trace b) after recording the first spectrum (trace a). The emission spectrum shows true quenching (as opposed to any wavelength shifted quenching).

This observation was useful to maintain any significant non-contained and thereby non-specific fluorescence of ELF in the sample.

EXAMPLE 10

PH Switched Activity of TNP-GALA

In order to demonstrate the pH switching potential of the GALA peptides, fluorescent calcein liposomes were assayed at different pH values in the presence of the GALA peptide alone and having a hapten, trinitophenol (TNP) which is an analogue of the explosive TNT ), attached at its N-terminus. The calcein assay was conducted in 2 ml of 10 mM buffer containing 140 mM NaCl. For acidic buffer sodium acetate was used at pH 5.4 While Tris-HCL was used for pH 7.4. In the assay 3 ul of calcein Liposomes were added to 2 ml assay buffer and fluorescence recorded. Peptide was added after steady baseline (usually more than 100 secs) was obtained and lysis followed.

Figure 18:
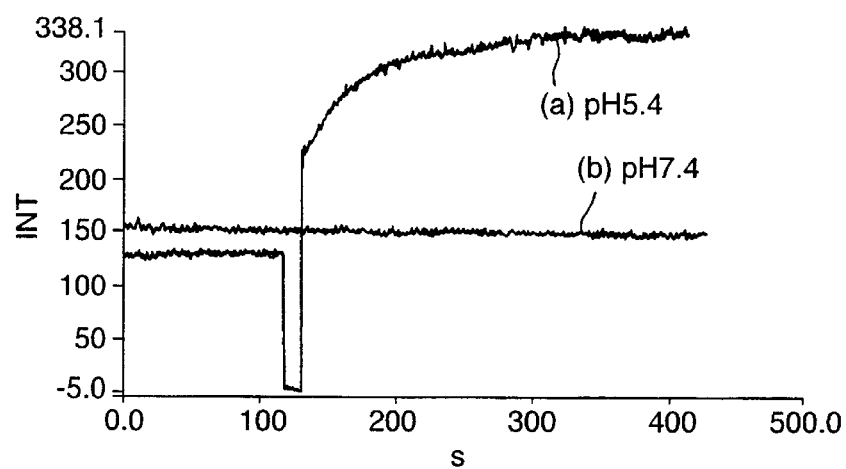
FIG. 18 shows pH switched activity of TNP-GALA.

The peptide was sensitive to pH with activity being switched on at lower pH values in this assay. The pH sensitivity is believed to be the result of helix formation induced by protonation of the aspartic acid residues. It is believed that pores form as the peptide enters into the liposome vesicles in its helical form at lower pH, and the pores cease to exist as the conformation is reversed at higher pH. The modification of GALA by TNP had little effect on the overall activity (see FIG. 18) although it shifted the acid response a little more towards the alkaline region. The retention of activity is expected since the modification was regiospecifically made on the N-terminus, which is not involved in helix stabilisation.

The effect of TNP-GALA on standard liposome contained alkaline phosphatase nanospheres using the colourimetric assay showed that the peptide did not release the enzyme, while it could release Calcein, indicating the desired size selectivity of the peptide channel. The pores formed appeared well suited to allow only small molecules such as substrate to transport into the nanosphere and not large molecules, such as the enzyme, or the fluorescent complex.

EXAMPLE 11

Fluorescent Product Produced by Alkaline Phosphatase at Acidic PH

The addition of ELF substrate to various buffers was investigated to see what effect these may have on the production of fluorescent product. A product was formed as described in Example 2 above but using a variety of buffers without the addition of the cobalt ion solution.

Excitation was at 355 nm and emission was at 525 nm. The results of the monitoring of the fluorescence are shown in FIG. 19.

In a typical experiment 2 ml of 10 mM sodium acetate buffer at pH 5.7 containing 4 μl of 5 mM ELF-97 was used and 10 μl of Liposomes added.

Figure 19:
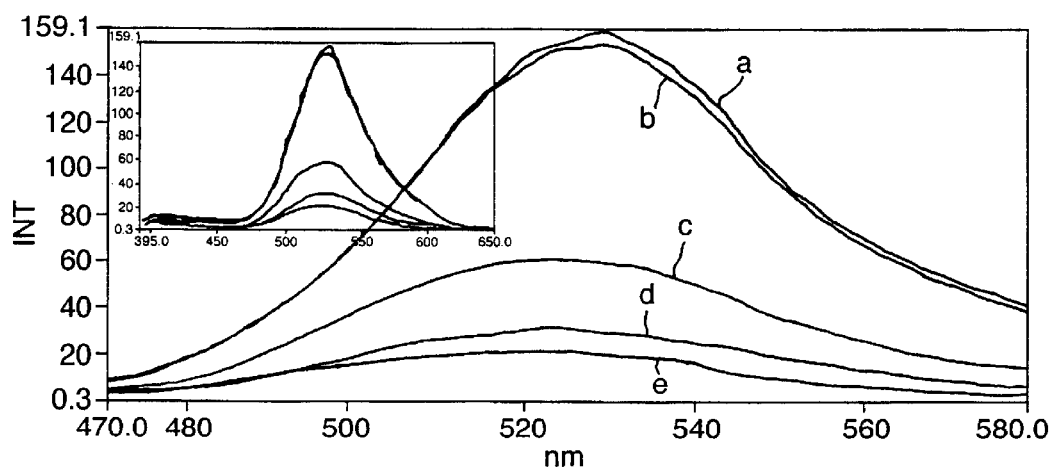
FIG. 19 is an emission spectra showing the effect of buffer type an pH on enzyme -substrate reaction.

FIG. 19 shows the intensities samples made up in a series of buffers measured immediately after samples had been produced. The immediate signal suggested that the Tris buffers were the most suitable and surprisingly that the enzyme was still active at pH 4. In FIG. 19 the traces are numbered with the highest first and correspond to the following buffers:

(a) 10 mM Tris-HCL pH 8.8 (peak intensity 155.76)

(b) 10 mM Tris-HCL pH 7.1 (peak intensity 155.76)

(c) sodium citrate pH 6.25 (peak intensity 155.76)

(d) sodium acetate pH 4 (peak intensity 155.76)

(e) sodium phosphate pH 7.6 (peak intensity 155.76)

Figure 19A:
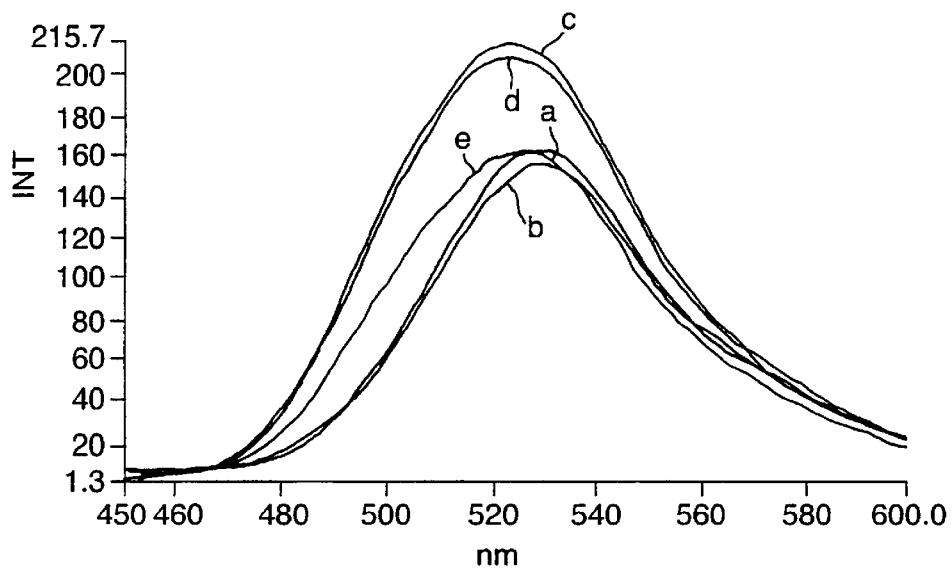
FIG. 19a shows the emission spectra after 1 hour and FIG. 19b shows the emission spectra after 26 storage.

After 1 hour the results reversed as shown in FIG. 19a. The acidic samples showed a higher intensity, even at pH 4. In addition all the traces except for the Tris buffer appeared to show a blue shift. The control showed no difference in peak position of excitation only of relative absorption.

Figure 19B:
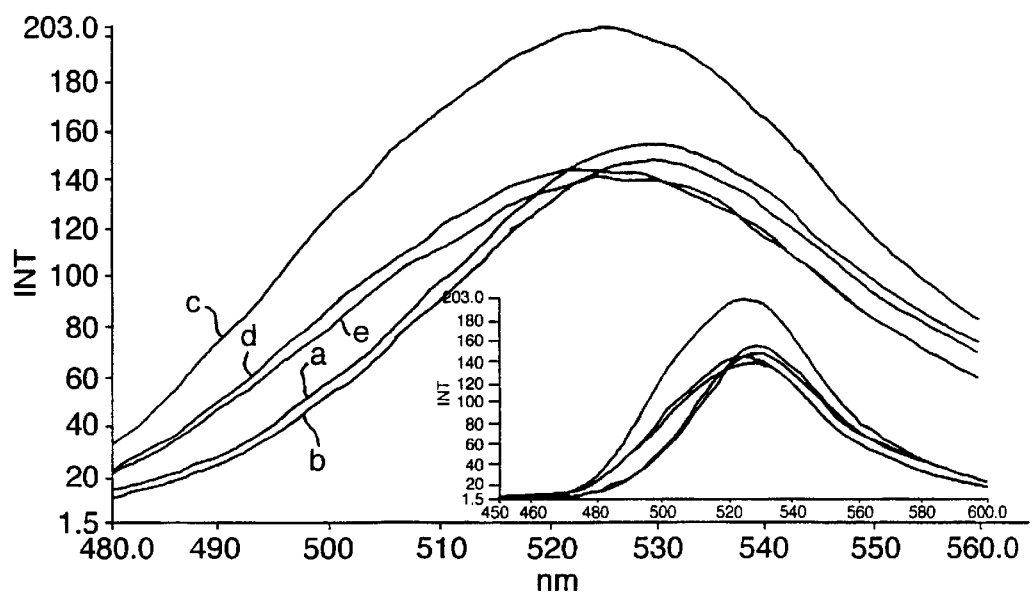

After 26 hours, FIG. 19b, all the samples except for the Tris buffers (a, b) where shown to have a blue shift. The frequency shift remained the same but the pH 4 sample was reduced to a similar intensity to that of the Tris buffers. It is noted that that the blue shift does not appear to simply scale with pH but appears to be dependant on buffer type. The emission spectra peaks did not move position throughout.

It appears surprisingly that the reaction by which ELF generates a fluorescent product could be catalysed by alkaline phosphatase at acidic pHs. Normally, alkaline phosphatase has undetectable activity at such pHs. Alkaline phosphatase catalysed generation of fluorescent product could be demonstrated at pH 4, where prior treatment of the ELF substrate with such buffers resulted in an unexpectedly rapid reaction on addition of enzyme.

This is useful in the context of the present invention as the TNP-GALA peptide is active at the lower pH range as shown above. Thus the catalytic effect of alkaline phophatase can be utilised in similar reaction conditions.

EXAMPLE 12

Figure 20:
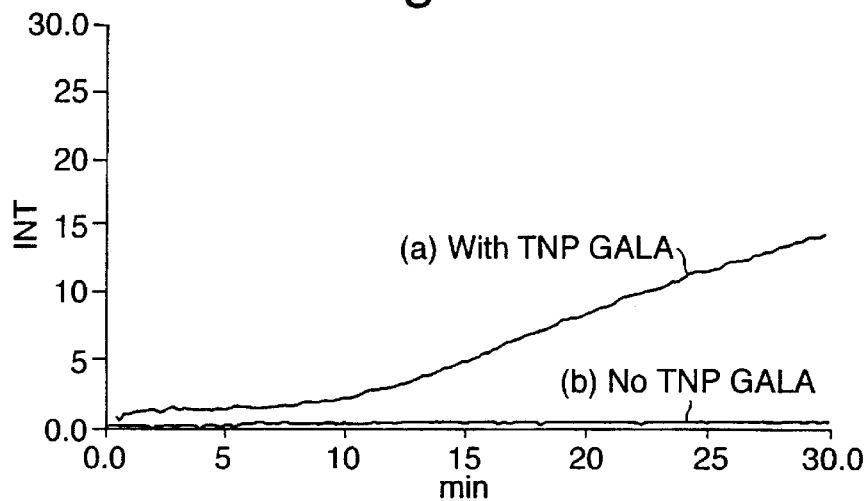
FIG. 20 illustrates TNP-GALA triggering of liposome contained alkaline phosphatase nanospheres to react with ELF-97 substrate.

TNP-GALA Triggering of Liposome Contained Alkaline Phosphatase Nanospheres to React With ELF-97 Substrate In a series of experiments, nanospheres containing signal generating alkaline phophatase enzymes were treated with TNP-GALA peptide at pH 5.7 in the presence of ELF-97 substrate, and the progress of the reaction was continuously measured by development of fluorescence. In a control experiment, no peptide was added. The results are shown in FIG. 20.

Increase in fluorescence signal was observed in the presence of peptide. Based on the above observations, it was concluded that the peptide forms channels which allowed the diffusion of substrate into the nanosphere particles. Once inside, the enzyme catalysis converts this to product, which is physically trapped due to the formation of a complex or solid too large to penetrate or diffuse through the small pores formed by peptide, which are under 1 nm in size.

Figure 21:
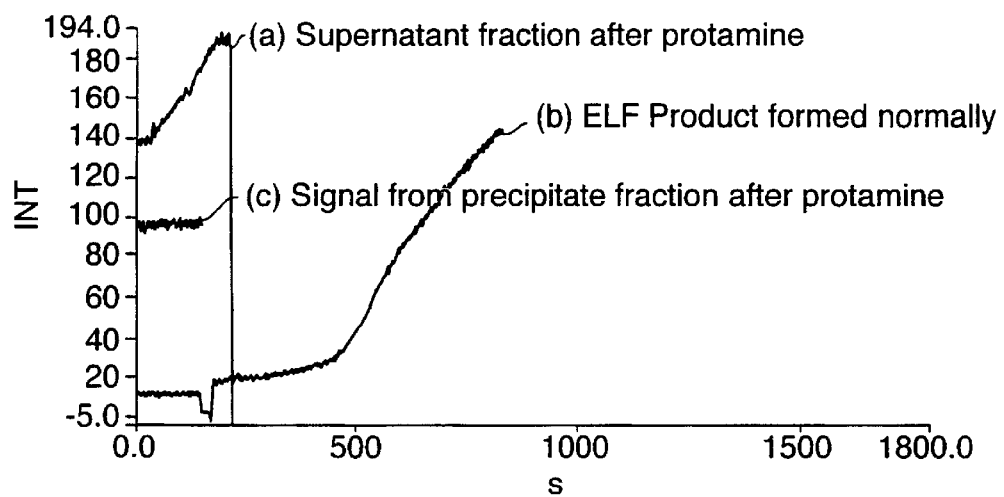
FIG. 21 shows the relative fluorescence levels in supernatant and sedimenting fraction after treatment of liposomal ELF with protamine.

Agglutination of liposomes in the presence of protamine was used to confirm that the signal developed was associated with the liposome fraction. The results are shown in FIG. 21.

Liposome-contained alkaline phosphatase production of the ELF product was triggered by TNP-GALA as before (trace b). The preparation was treated with protamine (1 mM). More than 50% of the fluorescent product was sedimented (trace c) by low speed centrifugation (2000 g for 10 min), leaving little in the supernatant fraction (trace a) indicating that the fluorescent product was mainly contained in the liposome-contained alkaline phosphatase nanosphere system.

EXAMPLE 13

PH-switched TNP-GALA Triggered Formation of ELF Product in Nanospheres of Liposome-contained Alkaline Phosphatase Similar methodology was used to investigate the effects of pH switching and antibody blocking on the activity of the TNP-GALA peptide on nanospheres of liposome-contained alkaline phosphatase.

Figure 22:
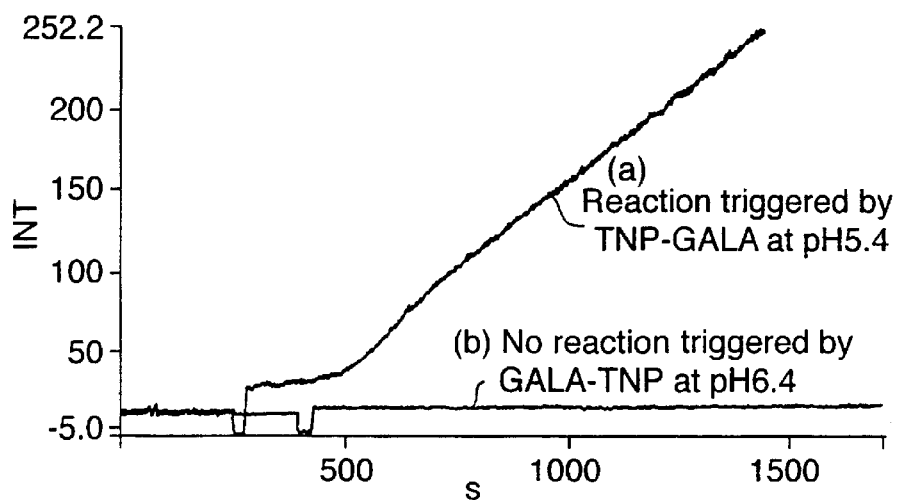
FIG. 22 shows pH-switched TNP-GALA triggered formation of ELF product in nanospheres of liposome-contained alkaline phosphatase.

It was found (FIG. 22) that the substrate reaction was triggered by TNP-GALA at pH of 5.4 but not at a pH of 6.4.

Figure 23:
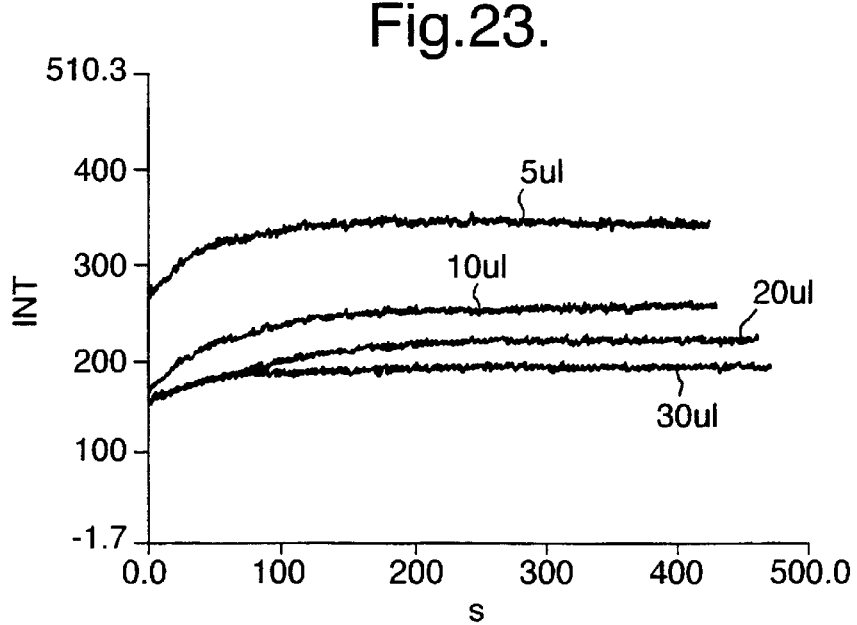
FIG. 23 illustrates the blocking of TNP-GALA activity by antibody titration.

On addition of monoclonal antibody against TNT in the given volumes (FIG. 23) to the TNP-GALA triggered liposome system, the activity of the TNP-GALA peptide was blocked quantitatively as shown by conventional release assay using calcein liposomes at various amounts of anti TNT antibody as indicated by the traces.

Figure 24:
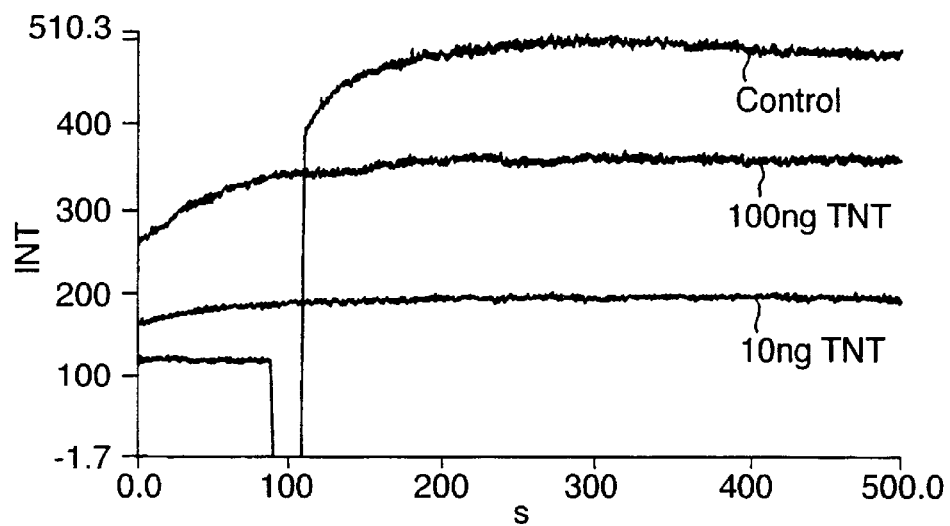
FIG. 24 shows competition of antibody blocking by TNT.

The reaction was repeated in the presence of 30 µl of antibody to block the activity of TNP-GALA but in this instance, TNT in various amounts was also added to the reaction. The results are shown in FIG. 24. TNT quantitatively competed with antibody blocking of TNP-GALA and the signal developed.

Thus it has been shown that the production of contained the FLF fluorescent product in the liposome-contained alkaline phosphatase nanospheres could be triggered by the TNP-GALA peptide, whose activity was switched in response to analyte. The activity of TNP-GALA peptide was modified both by pH and by antibody binding to the TNP hapten.

EXAMPLE 14

Peptide Insertion Through Membrane

Rather than (or, in some cases, in addition to) forming channels, peptides can be used to insert through membranes. A range of peptides may insert into and through membranes without provoking significant wider permeability changes through disruption of the permeability barrier provided by the lipid bilayer. Typical of such behaviour are signal peptides, such as the ones listed below, with and without FITC.

P25: (FITC)-MLSLRQSIRFFKPATRTLCSSRYLL (SEQ ID NO:12)-amide

P34: (FITC)-MLSLRQSIRFFKPATRTLCSSRYLLQQKPVVKTA (SEQ ID NO: 13)-amide (see Molecular and Membrane Biology, (1995) 2, 183–192).

In order to demonstrate binding, insertion and penetration, initially, either the above peptides were labelled with a fluorescent probe (the fluorescein isothiocyanate analogue, FITC) or the phospholipids were labelled with fluorescein (fluorescein phosphatidyl ethanolamine, FPE). The resulting changes in fluorescence may be used as a specifically triggered means of signal development, or the insertion and penetration of peptides may be used to trigger catalytic activity. It will be understood from the above, that the insertion and penetration activity of such peptides can also be blocked quantitatively using antibodies.

The liposome bilayer membrane has outer and inner phospholipid leaflets. Liposomes were prepared with FPE in both leaflets (by incorporating FPE into liposome preparation), and only on the outer leaflet (by modifying PE with fluorescein after preparation of the liposomes) (Biochem. (1996) 35, 10931–10937). By rapid mixing and monitoring of the changes in fluorescence, the binding and insertion of the signal peptides (P25, P34) was measured on a fast (1 to 100 msec) timescale and slower (1–50 sec insertion)timescale process.

Figure 25:
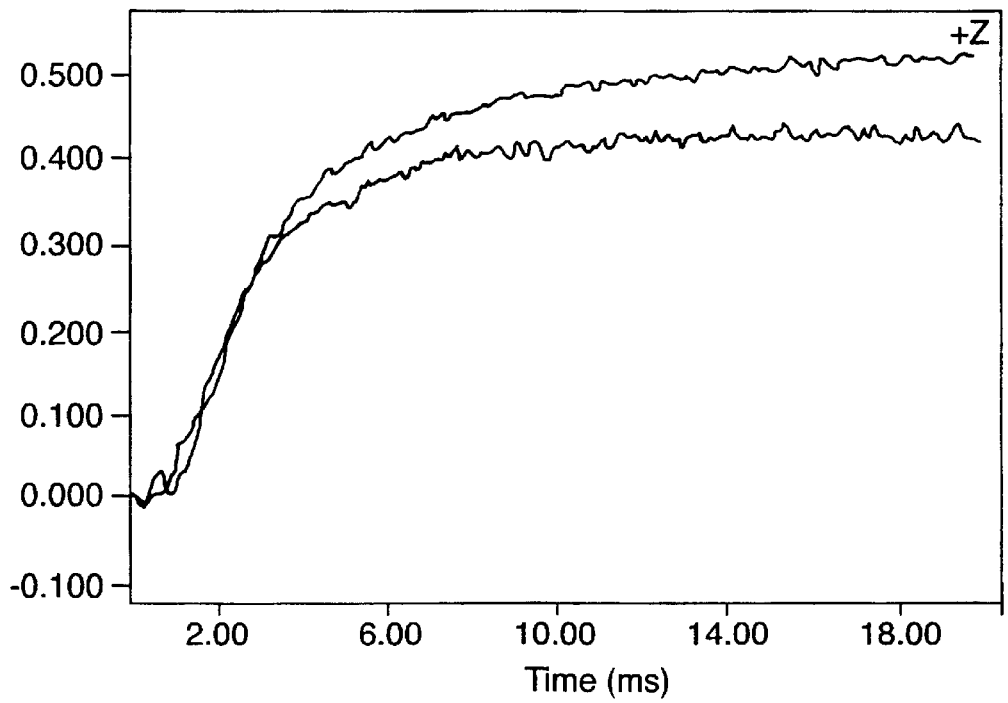
FIG. 25 shows the signals obtained by the binding of p-25 to FPE labelled liposomes.

The results at the 1 to 100 msec timescale are shown in FIG. 25. These show two signals showing the binding of p-25 to FPE labelled liposomes. One signal is produced when the FPE is present only on the outer leaflet and one when both the leaflets are labelled. A rapid increase in fluorescence as the peptides bind the to the phospholipid of the liposome is shown, which was of similar magnitude and kinetics, whether monitored for liposomes with FPE in the outer only or both (outer and inner) leaflets.

Figure 26:
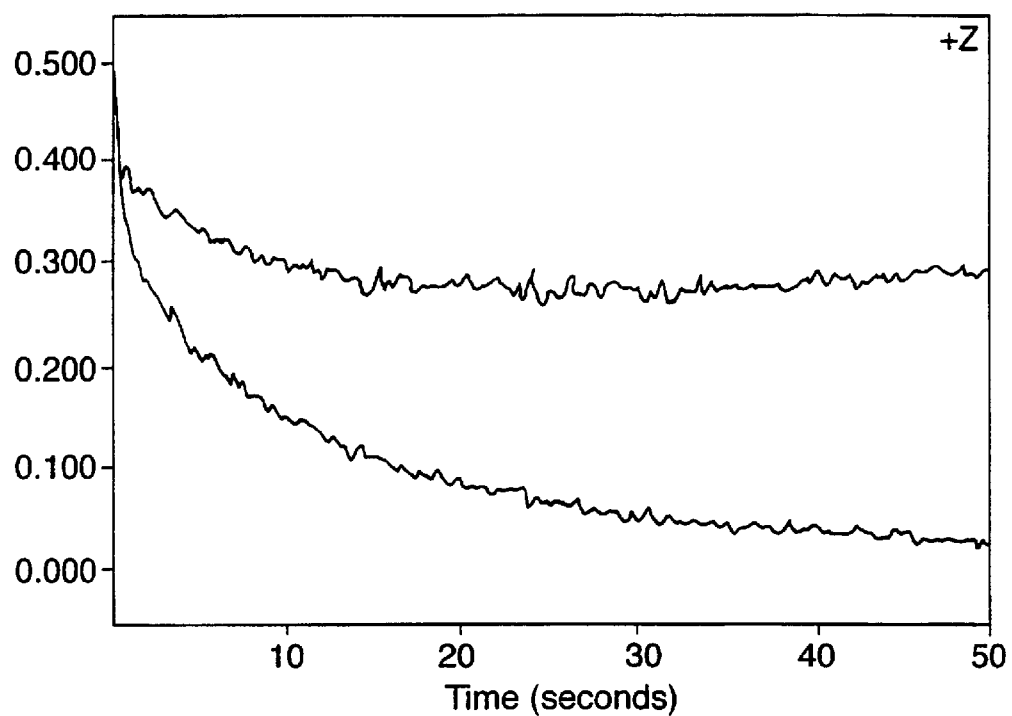
FIG. 26 shows the insertion traces of FIG. 24.
Figure 27:
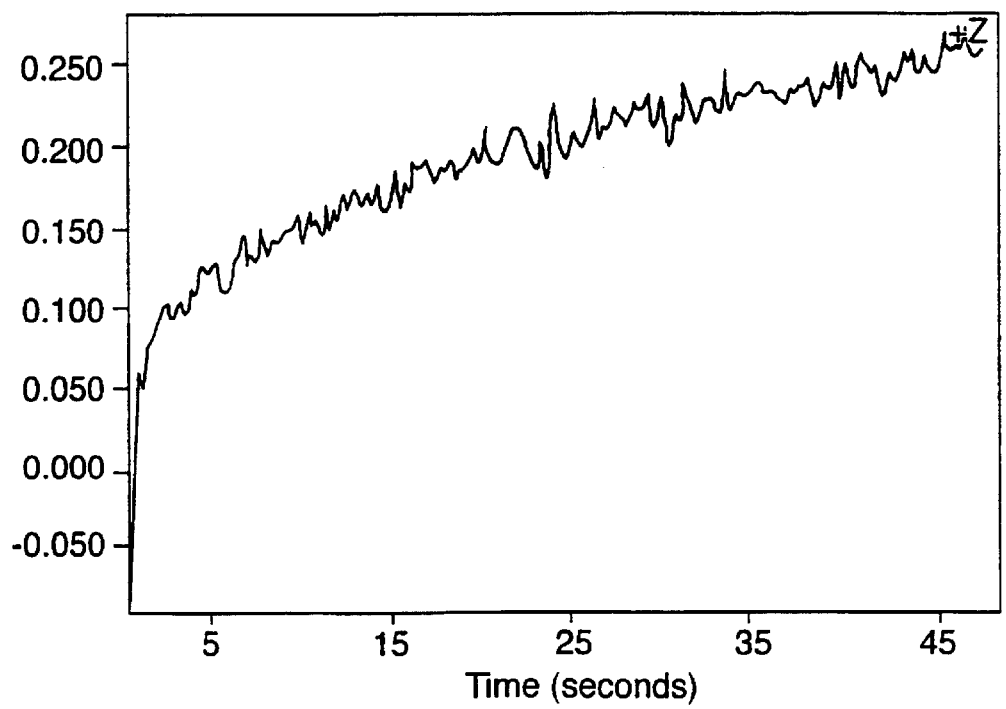
FIG. 27 shows the results of subtracting the signal obtained where FPE was on the outer leaflet from the signal when FPE was on both leaflets.

Results obtained at a 1 to 50 sec timescale are shown in FIG. 26. This shows a slower subsequent decrease in fluorescence as the peptide inserted, which was greater when the FPE was present only on the outer leaflet, indicating the process of insertion. Subtraction of the two traces, gives the signal obtained as the inner leaflet responds to the signal peptide and this is shown in FIG. 27.

These results illustrate the rapid (msec) binding and the slower (sec) insertion and penetration of the signal peptides through the membrane to the inner leaflet of the membrane bilayer of the non-modified signal peptide.

EXAMPLE 15

Use of Signal Peptide Insertion to Attach a Moiety Such That it Becomes Exposed at the Water/phospholipid Interface Insertion peptides were labelled at their N terminus with fluorescein, such that binding of anti-fluorescein antibody quenches fluorescence. It is known that antibody per se cannot penetrate significantly into the membrane.

Figure 28:
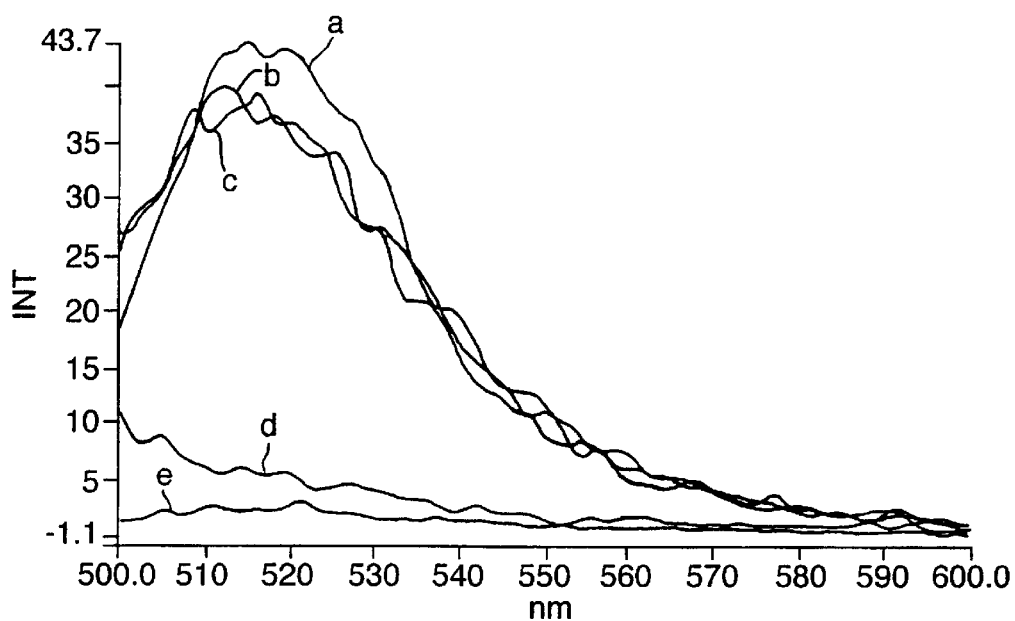
FIGS. 28 and 29 illustrate the effect of antibody on fluorescence of FITC-P25 and FITC-P34 liposomes respectively.

Fluorescent FITC-P25 (10μ of 50 μg/ml) was added to 2 ml of 10 mM Tris buffer pH7.1 and the fluorescence emission was scanned (FIG. 28 —trace a). The peptide was also added to liposomes (50 μl) in the same buffer and the emission scanned immediately (trace b) and after 1 minute (trace c). On addition of antifluorescein antibody (10 μl of 0.1 mg/ml, Sigma), the fluorescence emission was markedly quenched (trace d). The antibody showed no significant fluorescence (trace e).

Figure 29:
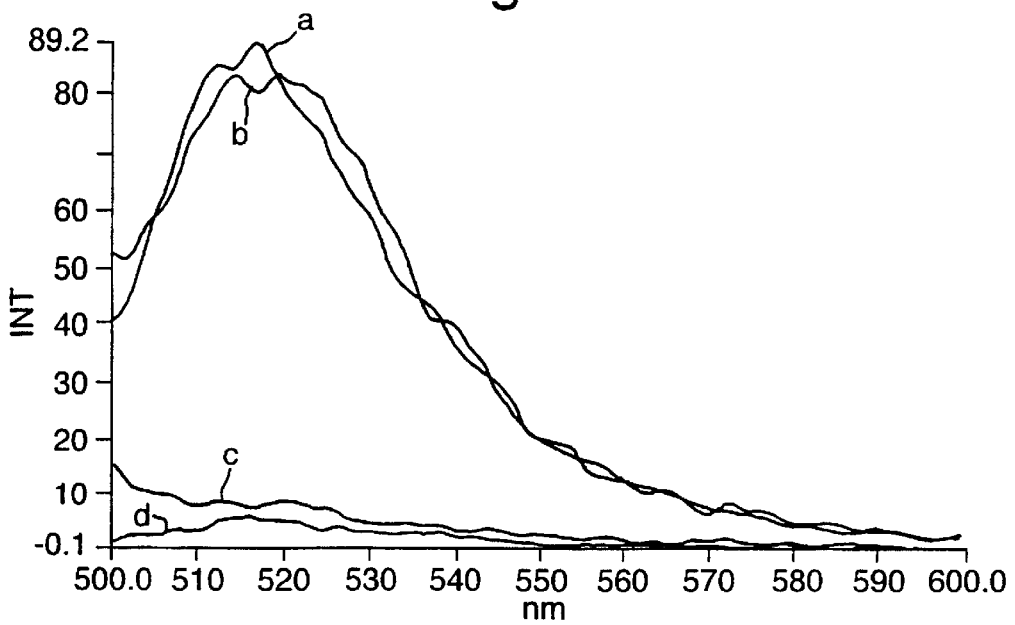

The same experiments were performed with the longer signal peptide P34. Fluorescent FITC-P34 (10 μl of 50 μg/ml) was added to 2 ml of 10 mM Tris buffer pH7.1 and the fluorescence emission was scanned (FIG. 29—trace a). The peptide was also added to liposomes (50 μl) in the same buffer and the emission after 1 minute (trace b). On addition of anti-fluorescein antibody (10 μl of 0.1 mg/ml), the fluorescence emission was markedly quenched (trace c). The antibody showed no significant fluorescence (trace d).

In this case, a similar small decrease in fluorescence was noted on binding of the peptide to the liposomes, but virtually all the fluorescence was quenched on addition of the antibody. This was expected as the peptide is longer and better able to span the membrane, and provides demonstration of improved presentation of the moiety attached to the peptide.

EXAMPLE 16

Insertion of Haem Catalytic Activity

Figure 30:
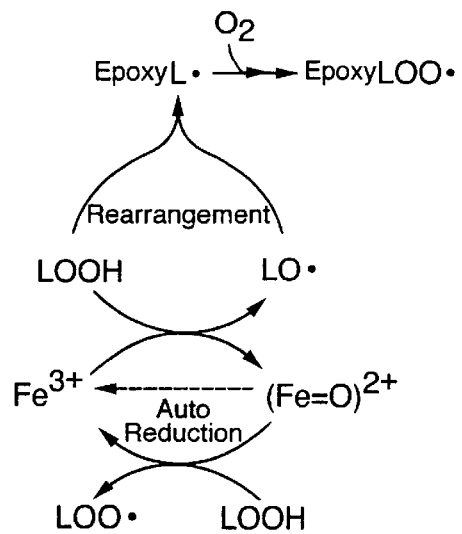
FIG. 30 illustrates the heam catalysed radical mediated chain reaction.

The initial demonstration relies on the "seeding" of the membrane with 13(S)-hydroperoxy-9, 11 (cis, trans)-octadecadienoic acid (13-HPODE), a lipid peroxide which reacts with haem forming a ferryl species which subsequently reacts with bulk lipid forming further peroxide, according to the reaction scheme shown in FIG. 30.

Figure 31:
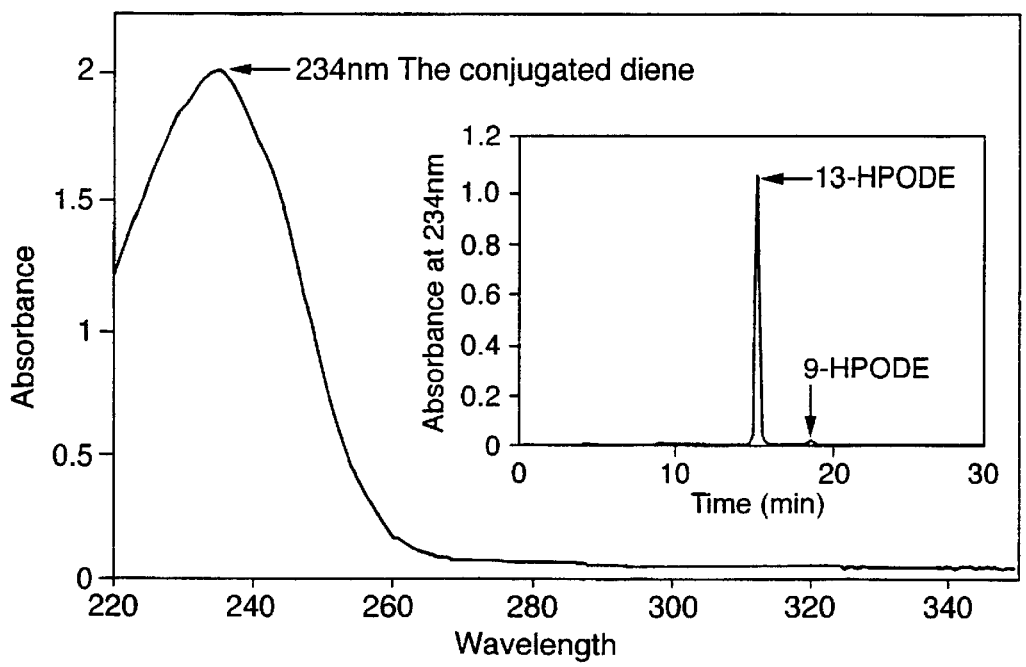
FIG. 31 shows the absorption spectrum and HPLC analysis of 13-HPODE.

13-HPODE, which is a lipid hydroperoxide was produced by the peroxidation of linoleic acid by soybean lipoxygenase-1, in 100 mM di-sodium tetraborate buffer at pH 9.4. After purification by HPLC, the absorption spectrum of 13-HPODE (80 μM) was obtained (FIG. 31). This shows a peak at 234 nm where the conjugated diene absorbs.

Figure 32:
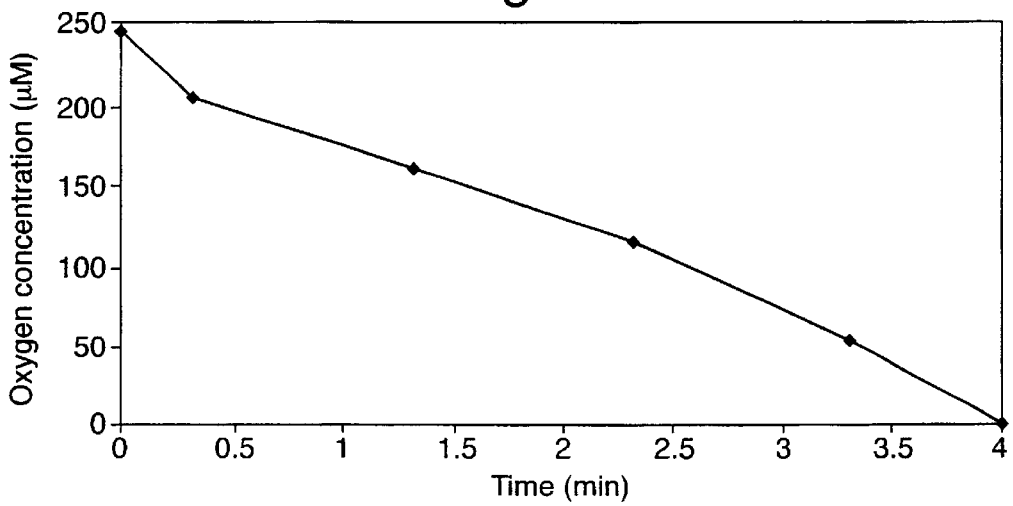
FIG. 32 illustrates oxygen consumption during the incubation of nanospheres with heamin and 13-HPODE.

Addition of haemin to 13-HPODE treated nanospheres led to full peroxidation of the lipid as seen by oxygen uptake (FIG. 32). Asolectin was used in order to prepare liposomes by sonication in 100 mM Hepes buffer pH 7.5. The liposomes (1 mg/ml) were incubated with haemin (10 μM), and 13-HPODE (49 μM), in the presence of the ion chelator EDTA (100 μM).

Figure 33:
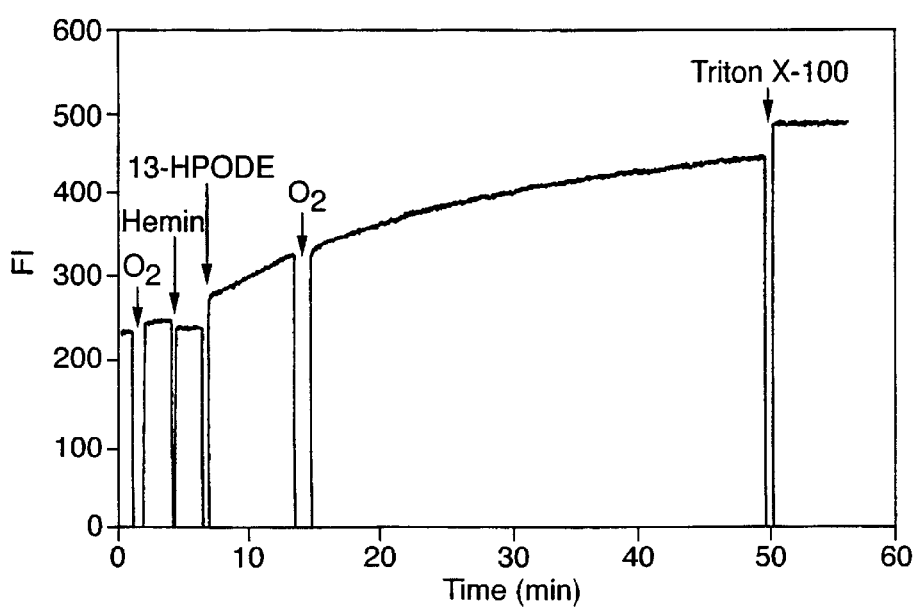
FIG. 33 shows how lipid peroxidation due to haemin and 13-HPODE, allows carboxyfluorescein to travel across a lipid layer.

Comparable experiments conducted optically corroborated this result showing changes in the lipid conjugated diene content, expected for peroxidation, and in the haemin spectrum. Asolectin nanospheres, having encapsulated 150 mM carboxyfluorescein, were prepared by sonication in 100 mM Hepes/100 μM at pH 7.5. The reaction was monitored using a Perkin Elmer fluorimeter; excitation wavelength 485 nm and emission wavelength 520 nm. Haemin (5 μM) and 13-HPODE (45 μM) were added to the labelled nanospheres. Oxygen was bubbled through the buffer twice. The results are shown in FIG. 33. An increase in the fluorescence intensity was noted. This increase indicates that carboxyfluorescein was released, therefore becoming more fluorescent. Triton X-100 was added in order to see the end point of the reaction.

Thus, addition of haemin to nanospheres containing encapsulated carboxyfluorescein led to enhanced fluorescence as a consequence of peroxidation. Control experiments (not shown) illustrated that it was only the combination of lipid+HPODE+haem which led to fluorescence enhancement.

EXAMPLE 17

Use of Alternative Heam Sources

An alternative source of haem is to use a haem protein which is also known to be peroxidative (i.e., myoglobin or haemoglobin).

Figure 34:
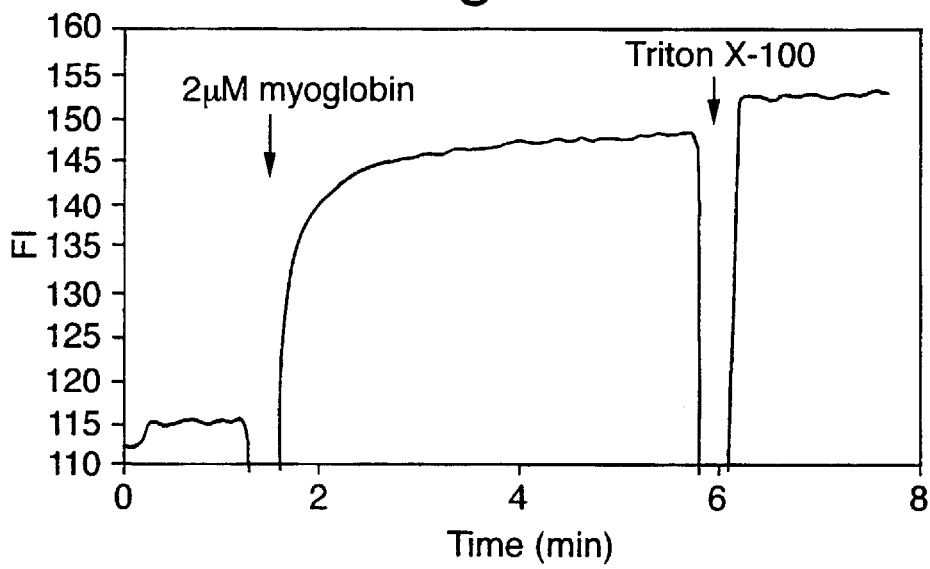
FIG. 34 shows how myoglobin allows carboxyfluorescein to travel across a lipid bilayer.

Nanospheres containing 150 mM carboxyfluorescein were prepared by sonication in 100 mM Hepes/100 μM DTPA at pH 7.5. Myoglobin (2 μM) was added to the nanospheres and the emission at 520 nm was followed as a function of time. The excitation wavelength was 485 nm. The results are shown in FIG. 34.

Figure 35:
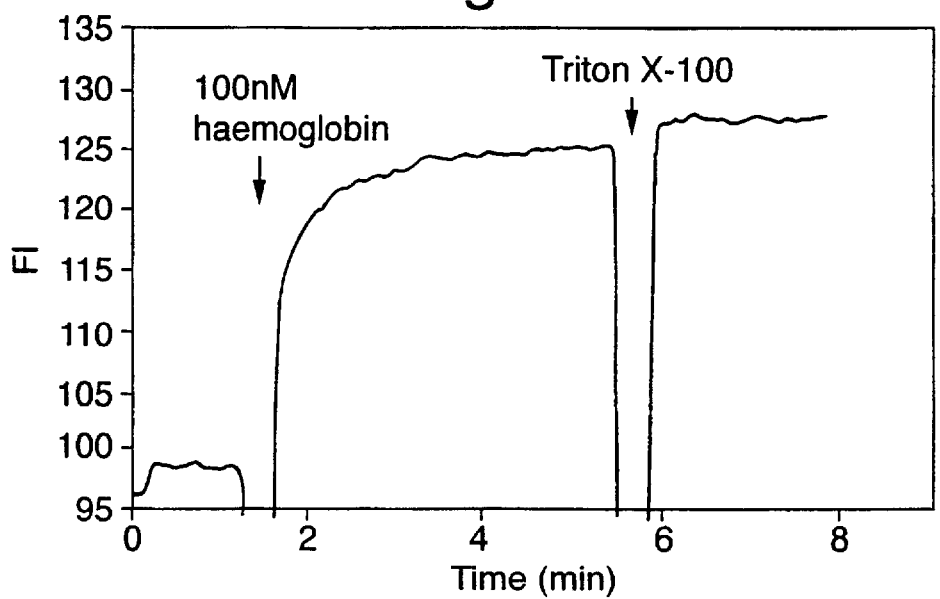
FIG. 35 illustrates the release of carboxyfluorescein from nanosphere interior as a result of the presence of haemoglobin.

Nanospheres containing carboxyfluorescein (150 mM) were prepared by sonication in 100 mM Hepes/100 μM DTPA at pH 7.5. As shown in FIG. 35, the fluorophore was slowly released when 100 nM (a low concentration) of haemoglobin were added to the nanospheres.

These results show that both myoglobin and haemoglobin are effective; haemoglobin being particularly efficient. Control experiments showed that haemoglobin had no direct effect on carboxyfluorescein.

EXAMPLE 18

Inserted Peptide as Catalytic Substrate

Figure 36:
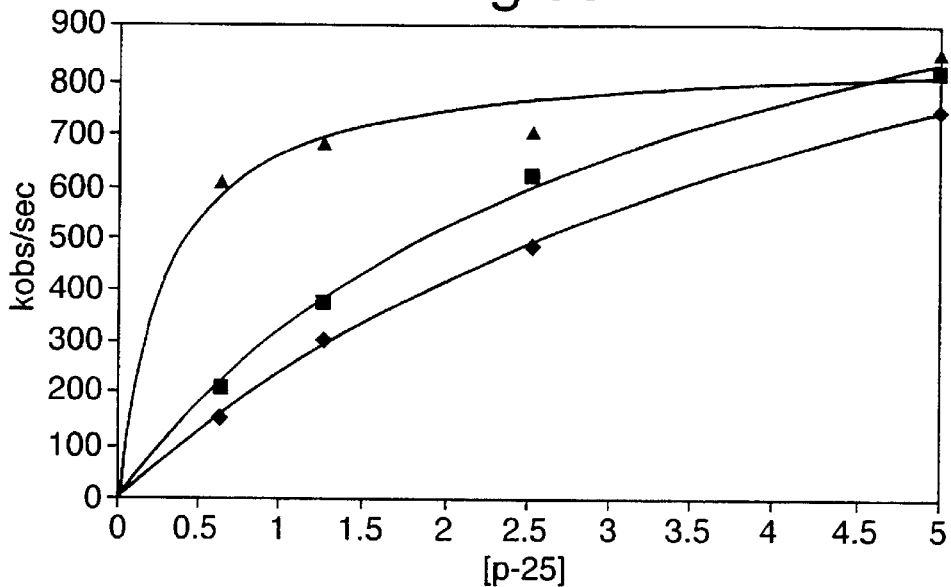
FIG. 36 illustrates diagrammatically liposome-contained proteolytic cleavage of peptide.

The rate of binding of the signal peptide P25 when cardiolipin (CL) into the membrane is incorporated into the membrane was investigated (See illustration in FIG. 36).

The dependence of binding rate constants for p-25 on peptide was analysed according to a model which incorporated a binding step followed by rearrangement of the peptide on the surface of the liposomes to give full fluorescence enhancement. The model can be described generally as $$a+b \xleftarrow{k} c \xrightarrow{k} d$$

and specifically as follows:

P-25+nanosphere $\xleftarrow{k}$ initial complex $\xrightarrow{k}$ final complex This model is described by the equation:

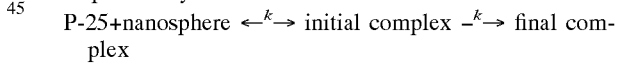

where K is the binding equilibrium constant, k is the rate constant for rearrangement on the surface and [P-25] is the concentration of the peptide.

The values of K and k for three liposome populations, comprising the normal phosphatidylcholine (PC) and those supplemented with various levels of CL, were as follows:

| Type of liposome | | $K(M^{-1})$ | $k(s^{-1})$ |
|---|---|---|---|
| PC | (♦) | $1.8 \pm 0.2 \times 10^5$ | $1.56 \pm 0.09 \times 10^3$ |
| CL/PC (1/50) | (■) | $3.1 \pm 0.3 \times 10^5$ | $1.37 \pm 0.08 \times 10^3$ |
| CL/PC (1/30) | (▲) | $3.5 \pm 1 \times 10^6$ | $8.52 \pm 0.4 \times 10^2$ |

Figure 37:
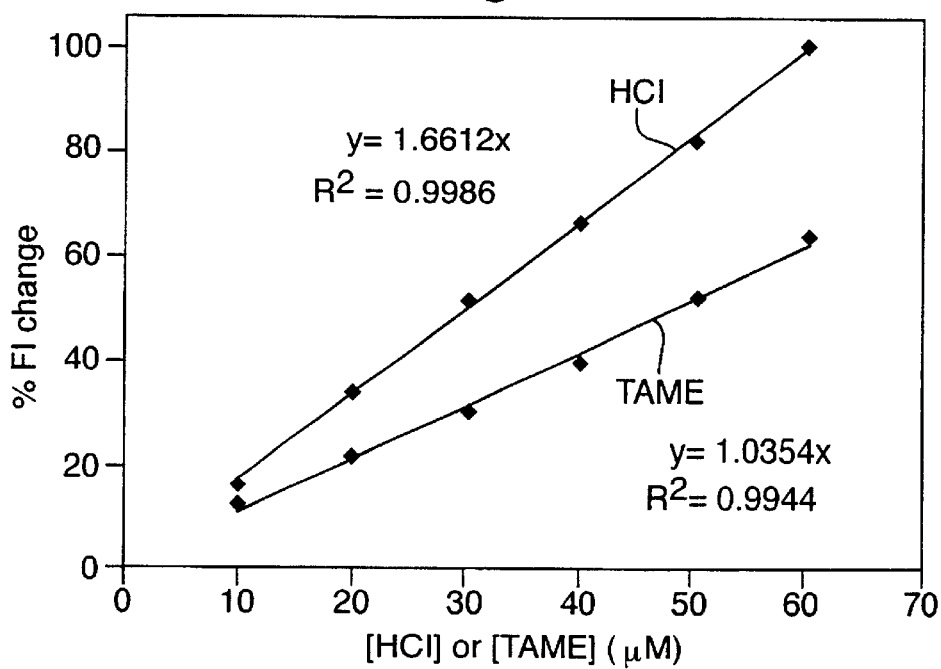
FIG. 37 shows the rate constants of binding of P-25 to phosphatidylcholine (PC) lipsomes in the presence and absence of cardiolipin(CL): where σ represents the curve for 1/30 CL/PC, ν represents the curve for 1/50 CL/PC and υ represent 100% PC.

The results (FIG. 37) matched the model and illustrate an enhanced binding constant between the positively charged peptide and the liposome on addition of negative charge.

Interestingly, the rate constant for rearrangement in the surface is lowered, possibly by tighter binding between specific charges on the peptide and the surface leading to some steric restraint to movement.

CL bears two phosphate groups, accounting for the increased binding of the positively charged peptide. This rate enhancement was accompanied by an unexpected decrease in amplitude.

This latter phenomenon was determined more extensively by determining the effects of negatively charged lipid on the properties of the fluorophore, FPE, when incorporated into the membrane. It was found that the transfer of FPE across the bilayer was increased.

Thus it appears that negatively charged lipids such as cardiolipin enhanced the rate of binding and, in particularly, the insertion rates and also tend to increase transfer of FPE across the bilayer.

EXAMPLE 19

PH Effects on Proteolytic Cleavage

One method of containing the detection of the proteolytic cleavage of the peptide such as p25 is to measure pH. The hydrolysis of the incoming peptide can be detected through the fluorescence of FPE.

It was found that at pH 7, where the carboxyl group is deprotonated and the amino group protonated, there is no net proton uptake from or ejection into solution. However, at pH 9, proton ejection was found as the amino group will be only partly protonated. The magnitude of the detected change was increased by further modifications of the peptide.

Figure 38:
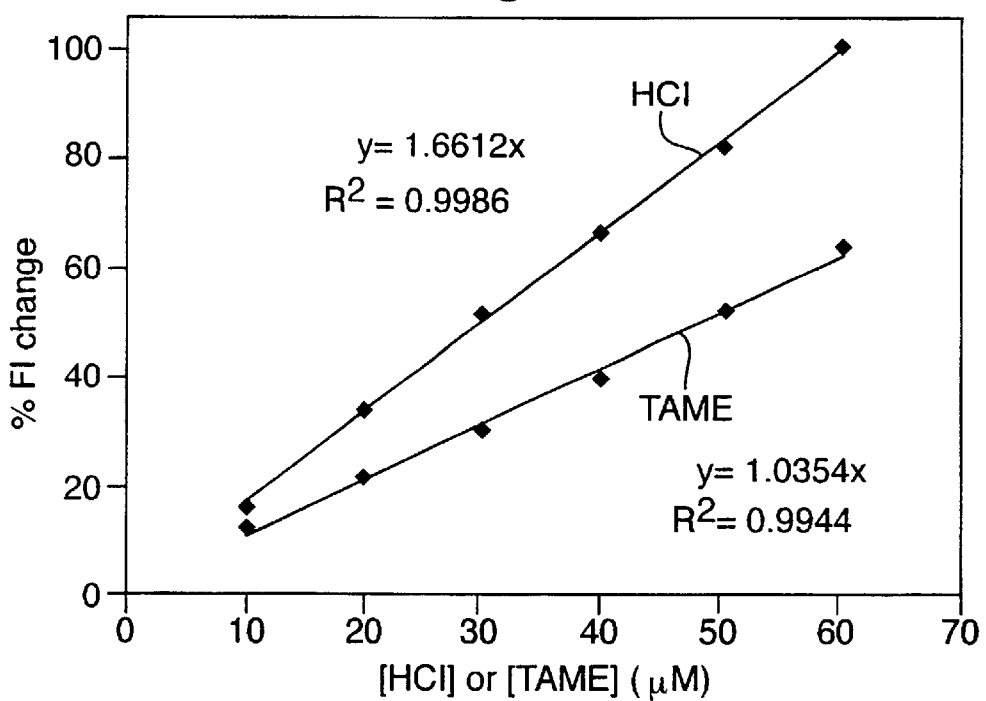
FIG. 38 illustrates fluorescence change (5) against the concentration of the protons in solution.

For example, substitution of an ester (TAME) for the peptide resulted in much better fluorescent signal change. Hydrolysis of TAME by trypsin released an average of 0.6 protons per molecule, against an HCl standard (FIG. 38). The ratio of the slopes of the TAME:HCl plots is 0.6258. The value is less than unity because of some proton uptake by the titratable groups of arginine.

This experiment indicated that FPE fluorescence monitored ester hydrolysis.

Typically, in the case of trypsin or chymotrypsin approximately 200–300 molecules of the proteinase can be contained in a liposome of approximately 100 nm diameter. While small relatively hydrophobic substrate molecules (e.g. for chymotrypsin benzoyl-L-Tyr-p-nitroanilide or acetyl-L-Phe-p-nitoanilide from Bachem) can permeate the membrane directly larger substrate (e.g. succinyl-L-Ala-L-Ala-L-Pro-L-Phe-p-nitoanilide (AAPF (SEQ ID NO:9))) do not permeate the membrane unless coupled to such signal peptides.

Typically, in the case of trypsin or chymotrypsin approximately 200–300 molecules of the proteinase can be contained in a liposome of approximately 100 nm diameter. While small relatively hydrophobic substrate molecules (e.g. for chymotrypsin benzoyl-L-Tyr-p-nitroanilide or acetyl-L-Phe-p-nitoanilide from Bachem) can permeate the membrane directly larger substrate (e.g. succinyl-L-Ala-L-Ala-L-Pro-L-Phe-p-nitoanilide (AAPF (SEQ ID NO:9))) do not permeate the membrane unless coupled to such signal peptides.

EXAMPLE 20

Electron Microscopy Studies

Signal was introduced into the Nanospheres by incubation of alkaline phosphatase containing Nanospheres (0.2 ml) in 10 mM Tris pH 7.1 (2 ml), followed by the addition of the peptide GALA-TNP (200 ml, 0.1 mg/ml) to form the pores and finally ELF-97 (40 ml, 5 mM) substrate. The preparations were fixed using a 2% (w/v) osmium tetroxide, 0.1M sodium cacodylate and 2 mM calcium chloride solution adjusted to pH 7.4. Aliquots (1.5 ml) Nanospheres were added to 2% osmium tetroxide solutions (4.5 ml) and agitated gently for two hours.

An aliquot (1 ml) of the Nanosphere/osmium solution was then added to a 0.5% (w/v) gelatin, 0.1M sodium cacodylate, 2 mM calcium chloride solution (5 ml) to prevent close packing. Small amounts (300–500 ml) of the resulting solutions were filtered using 100 nm pore filters under gentle suction. The filters were then dehydrated using a series of ethanol washes (70%–100% v/v) and finally placed in propylene oxide. The filters were then infiltrated with Spurr's resin and dried at 60° C. for 16 hours. Ultrathin sections (100 nm) of the sample were then prepared perpendicular to the plane of the filter using a Reichert Ultracut E ultramicrotome. Sections were placed on copper grids (200 mesh, 3.05 mm), and stained with uranyl acetate (2%) and lead citrate (2%). Electron micrographs were taken using a JEOL 100 CX II transmission electron microscope.

Figure 39:
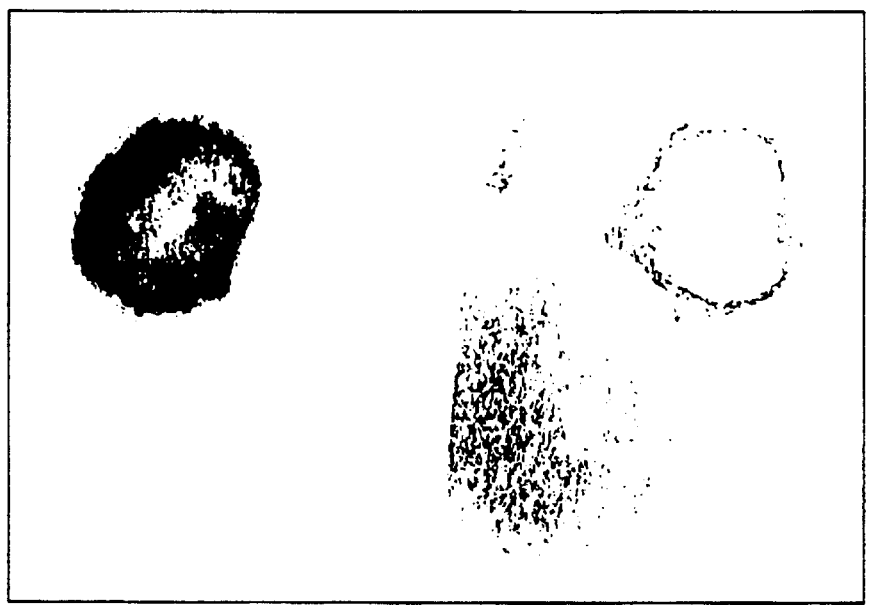
FIG. 39 illustrates transmission microscopy of liposome-contained reaction.

Electron microscopy studies illustrated in FIG. 39 demonstrated that the product was retained in the liposome-contained alkaline phosphatase particles following the peptide triggered reaction.

GALA peptide triggered reaction of ELF 97 by liposome-contained alkaline phosphatase showing considerable deposits of the fluorescent product, particularly close to the membrane region (FIG. 39 left) compared to a non-triggered control liposome (FIG. 39 right).

EXAMPLE 21

Nanosphere Detection

Figure 40:
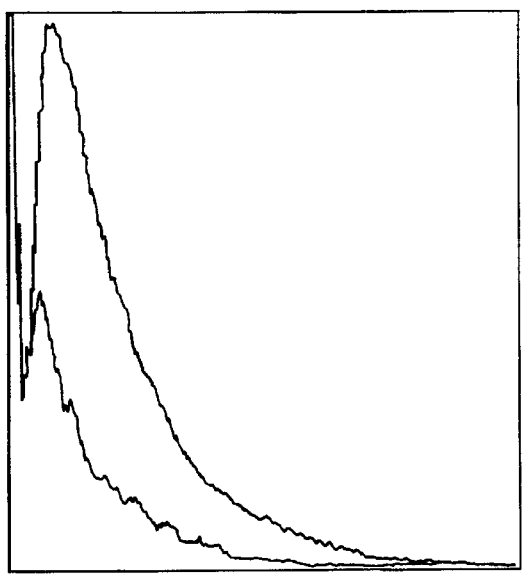
FIG. 40 illustrates signals from fluorescent and non-fluorescent nanospheres.

Liposome-contained alkaline phosphatase nanospheres were triggered by the GALA peptide to produce the ELF-97 product and were compared to non-triggered nanospheres. FIG. 40 shows typical intensity distribution data for the fluorescent, reacted (upper trace, scaled at 4096) and non-fluorescent, non-reacted (lower trace, scaled at 1024). The distribution plots the number of counts against the intensities of the particles (increasing to the right). The non-reacted nanospheres showed 8 fold less signal, whereas the reacted nanospheres were clearly detected with the peak appearing further to the right. This facilitated detection of reacted nanospheres.

Such studies demonstrated that it was possible to measure 30,000 or less nanospheres, which is at least $\frac{1}{1000}$ less than required in a normal assay.

These results also demonstrate that in any population, reacted nanospheres can be discriminated from non-reacted nanospheres. Partially reacted nanospheres were not significantly detected.

This means that the method of the invention is suited for a digital (or counting) method of detection of the triggered nanosphere contained reactions.

Figure 41:
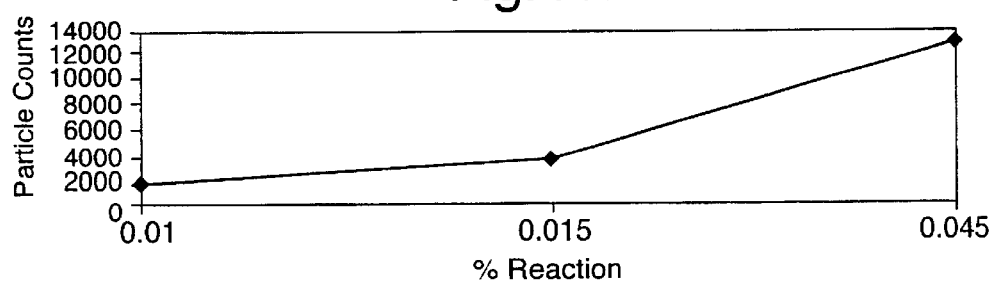
FIG. 41 shows particle counts of nanospheres.

The higher sensitivity and resolution of a digital method was demonstrated by detection of nanosphere populations that contained different levels of reacted and non-reacted nanospheres. Populations with different levels of reacted nanospheres were prepared and analysed. The results are shown in FIG. 41 and tabulated in Table 1 below. Low levels of reacted nanospheres and small changes in the number reacted were detected,showing that reacted nanosphere counts as low as 0.01 to 0.045% of the population were detectable.

| % reaction | Particle counts |
|---|---|
| 0.01 | 2135.5 |
| 0.015 | 4341 |
| 0.045 | 13186 |

On the basis that <$10^3$ peptide molecules triggered each nanosphere reaction, the physical detection sensitivity demonstrated is equivalent to approximately $10^{-17}$ moles of analyte.

EXAMPLE 22

PH-switched TNP-KALA Triggered Formation of ELF Product in Nanospheres of Liposome-contained Alkaline Phosphatase It was found (Example 13 above) that the substrate reaction was triggered by TNP-GALA at pH of 5.4 but not at a pH of 6.4. The GALA peptide is active at acidic pH where antibody antigen interactions are not favoured. Consequently another peptide, WEAKLAKALAKALA-KHLAKALAKALKACE (SEQ ID NO:10) labelled with TNP on Lys 15 (TNP-KALA), was used to show modulation of substrate channel with analyte TNT.

To a 2 ml buffer solution was added 3 μml of Nanospheres containing marker and 10 μml of 0.1 mg/ml KALA-TNP peptide prepared in water. The increase in fluorescence intensity was followed continuously after the addition of substrate (ELF97) using excitation and emission wavelengths of 365 and 515 nm respectively.

Figure 42:
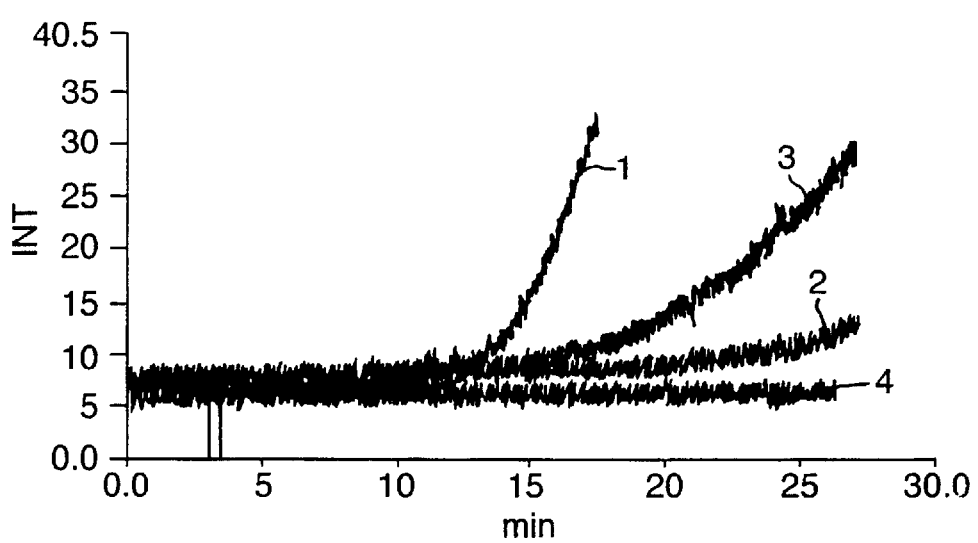
FIG. 42 shows detection of analyte (TNT) by formation of ELF-product in nanospheres containing alkaline phosphatase.

In order to monitor antibody binding, 30 μml of antibody solution was typically used with up to 1 μmg of peptide in a total assay volume of 2 ml. In analyte responsive experiments, TNT was added at different levels from a 0.01 mg/ml solution to antibody followed by peptide and 10 min incubation. FIG. 42 shows the data for 0.1 ug of TNT. Conditions for the assay were 3 μl Nanospheres and 2 ml ELF in 2 ml 10 mM Tris buffer pH7.4. The trace 1 is with 20 μl KALA-TNP peptide (0.1 mg/ml), while the trace 4 is with Nanospheres alone. The trace 2 is with 30 μl of anti-TNT antibody and 20 μl of KALA-TNP peptide preincubated for 10 minutes. In the analyte responsive curves trace, 30 μl anti-TNT plus 10 μl TNT (0.1 or 0.01 mg/ml solutions) and 20 μl KALA-TNP peptide (0.1 mg/ml) were sequentially added and incubated for 10 min.

On addition of monoclonal antibody against TNT in the given volumes (FIG. 42) to the TNP-KALA triggered liposome system, the activity of the TNP-KALA peptide was blocked quantitatively.

Thus it has been shown that the production of contained the ELF fluorescent product in the liposome-contained alkaline phosphatase nanospheres could be triggered by the TNP-KALA peptide, whose activity was switched in response to analyte.

EXAMPLE 23

The use of Melittin Peptide as a Pore Forming Reagent

Liposomes (100 μL) as containing alkaline phosphatase were suspended in 1 ml of 10 mM Tris-HCL buffer containing 140 mM NaCl pH7. Then 3 μg of TNP conjugated peptide (GIGAVLKVLTTGKPALISWIKRKRQQ (SEQ ID NO:11) labelled with TNP on lysine 13) was added to effect lysis. After 10 mins the mixture was spun in ultracentrifuge at 100,000 g for 1 hr to separate released enzyme from that associated with nanoparticles. The amount of enzyme activity was determined in the supernatant and compared to that in the triton (10 μl of 0.1%) solubilised sample. It was found that the enzyme predominantly (99.1%) remain associated with the liposomes as only 0.9% of the activity was found in the supernantent of peptide treated sample compared to the supernantent of triton treated sample. The peptide melittin TNP-13 was thus selected as suitable to evaluate analyte detection as the pores it forms does not allow significant enzyme release.

EXAMPLE 24

Detection of Analyte ml of 10 mM Tris-HCL pH 7.4 buffer and the peptide of Example 23 (1 μg) with 30 μl of anti TNT which was preincubated with TNT (1 μg) in the case of test sample for 15 mins. No TNT was present in the background sample. Liposomes 10 μl and substrate (ELF-97 molecular probes) 4 μl of 5 mM solution was added next and the fluorescence of samples recorded continually. As the diffusion of substrate is relatively slow process the samples were left overnight before measuring their detection by particle counting. The samples at 1, 100 and 1000 fold dilutions were also measured using the flow cytometer.

It is known that the ELF substrate is known (Molecular probes handbook) to form solid fluorescent product which would thus be retained within the particles and that the enzyme also remain within the particles under these circumstance (Example 23). The fluorescence increase was significantly greater with test samples than control without TNT.

However, most fluorophores quench at high concentration. Furthermore, the excitation for ELF must be within a narrow band in the near UV and the majority of high power commercially available lasers used in research operate optimally in the 488–1064 nm range. A liposome has a thin wall (5–10 nm) of low refractive index and scatters little light. The substrate is dissolved and scattering is also limited. However, the test sample liposomes are filled with a relatively high refractive index material and scatter a significant quantity of light. The material is not optically active at 488–524 nm where argon ion lasers may be used.

This example used measurement of 90 degree light scatter using the green channel on a modified Epics flow cytometer with a dicrohic mirror centered on 488 nm, bandwidth of approximately +/−40 nm, fitted with a coherent innova 90 argon ion laser operating on all-lines. The 'peak' scatter signal was monitored on a 1024 channel A/D, unless otherwise state a voltage of 600v was applied with a post amplification of 20.

Measurements were carried out at a flow rate of approximately 30 μl/min for a period of 100 seconds.

The background and test samples showed a distinct characteristic scatter distributions when analysed by the flow cytometer. The signal from a sample of water is of a different shape to that of background sample which is of different shape to that of test sample. This is expected as dense precipitate is deposited in the particles giving higher scatter intensity. It is advantageous to measure particles by counting methods as lower concentrations could be detected as shown by experiments at 1/100 and 1/1000 dilutions relative to the usual fluorimeter the test sample. The 1/100 and 1/1000 samples were too dilute to be reliably measured by conventional fluorescence however in all these cases the distribution remains characteristic of the test sample when measured by flow cytometer. On this basis individual particle counting has much higher sensitivity level than conventional detection.

Figure 43:
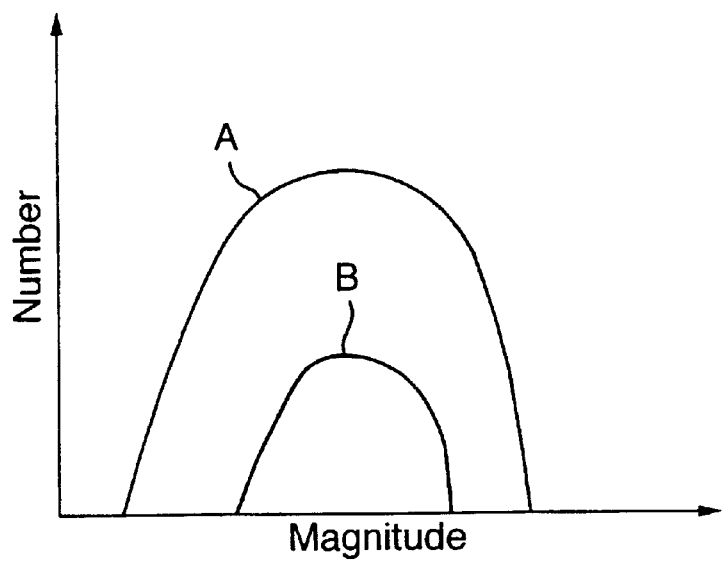
FIGS. 43 and 43A illustrate theoretical background traces which may be generated in an assay of the invention using a flow cytometer.
Figure 43A:
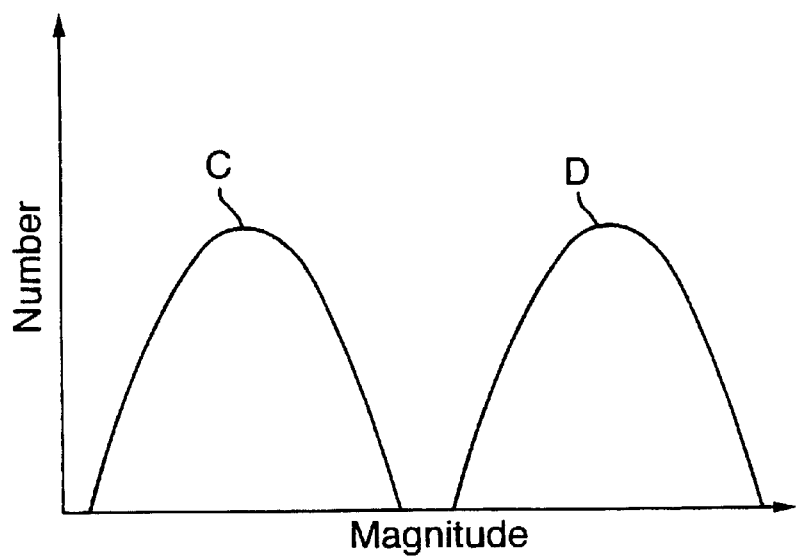

FIGS. 43 and 43A show possible theoretical traces for a background signal in this type of assay. In FIG. 43, the test sample total count (A) is larger than the background sample total count (B) but of the same form. That is the background sample contains a smaller number of particles which are similar to the test sample.

In FIG. 43A, the test sample and background sample are shown to contain the same number of particles but the test sample is of larger and/or more dense particles. The background is a small quantity of signal in all, or a population, of the liposomes whereas the test sample contains fully activated liposomes. It will be obvious to one skilled in the art that the latter case allows better discrimination of signal to background.

The following experiment suggests that the operation of the TNT assay is predominantly as the latter theoretical case where different distributions, as opposed to merely counts, are present.

Figure 44A:
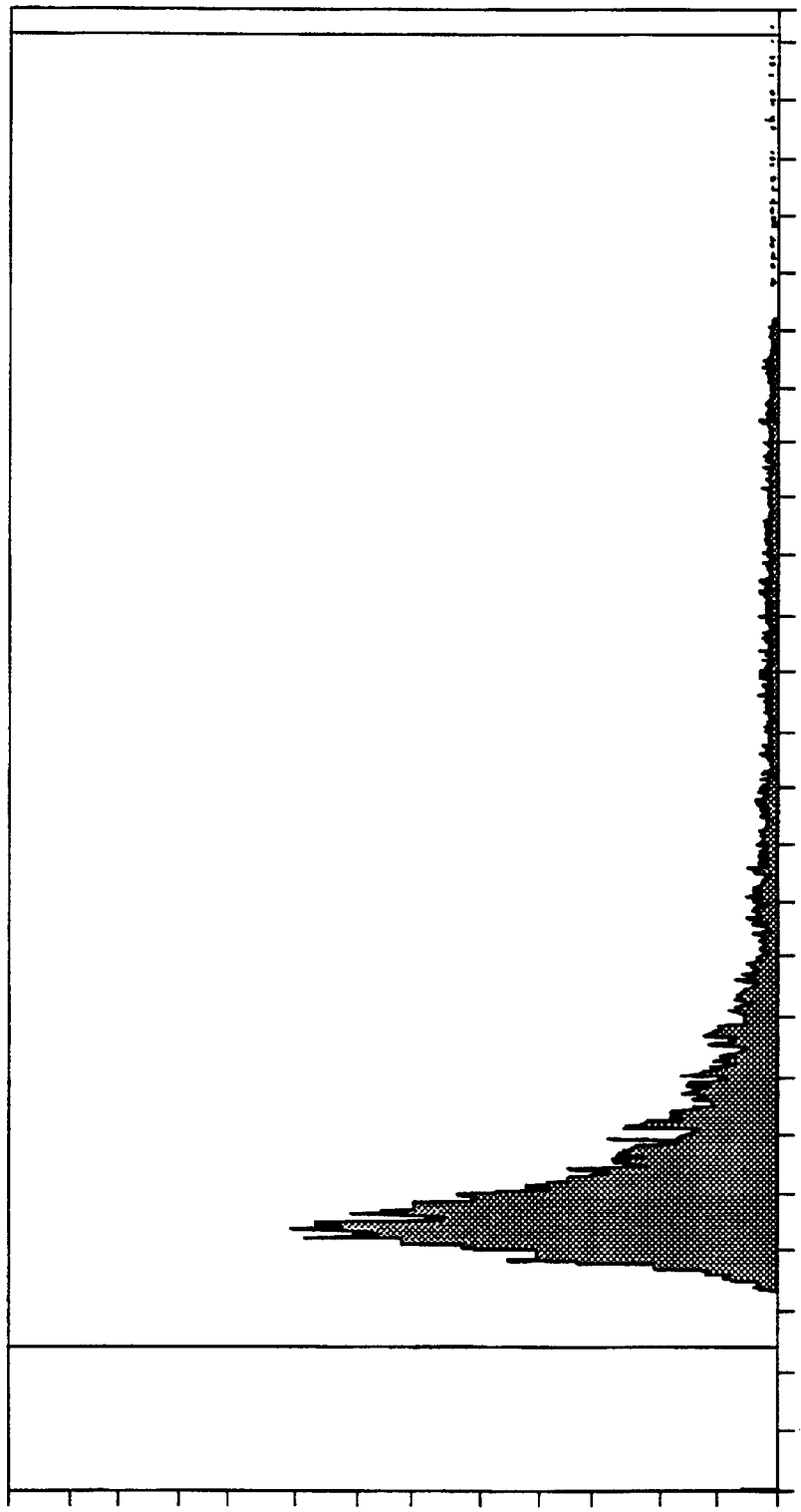
FIG. 44 A-S illustrate the results obtained using a flow cytometer in an assay of the invention.
Figure 44B:
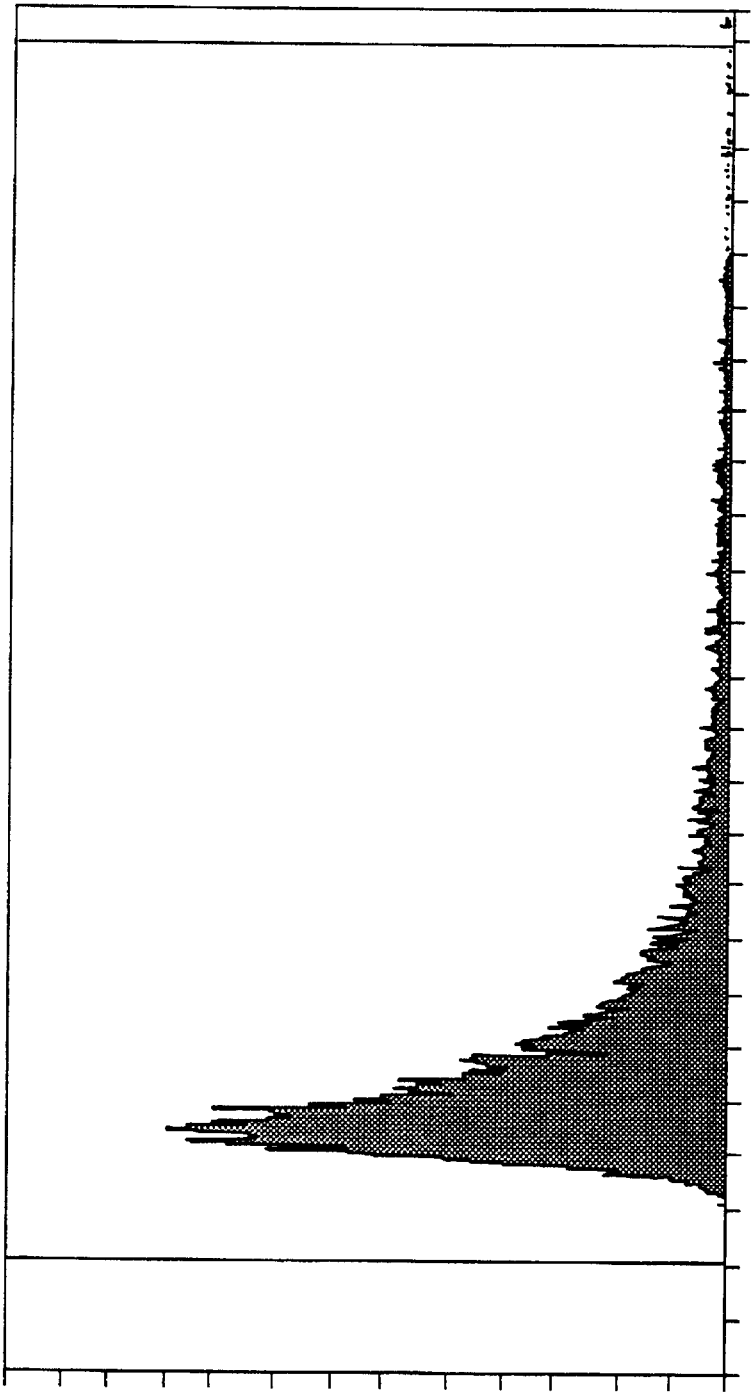

FIG. 44A shows a count of approximately 70 counts per second (cps) for water whilst FIG. 44B, shows the background signal was higher at approximately 100 cps, the shapes are broadly the same although the background signal may be seen to be shifted slightly to the right.

Figure 44C:
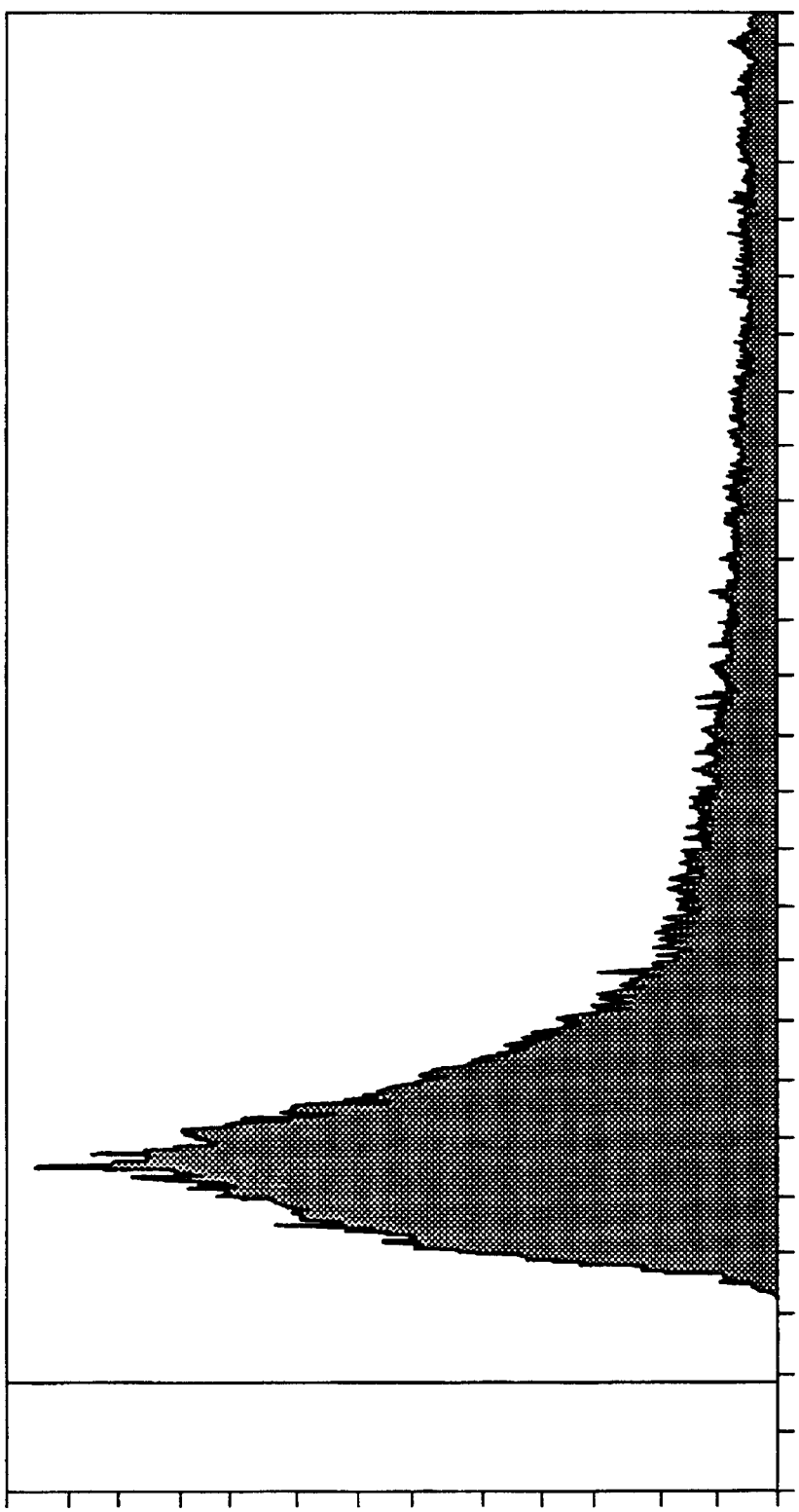
Figure 44E:
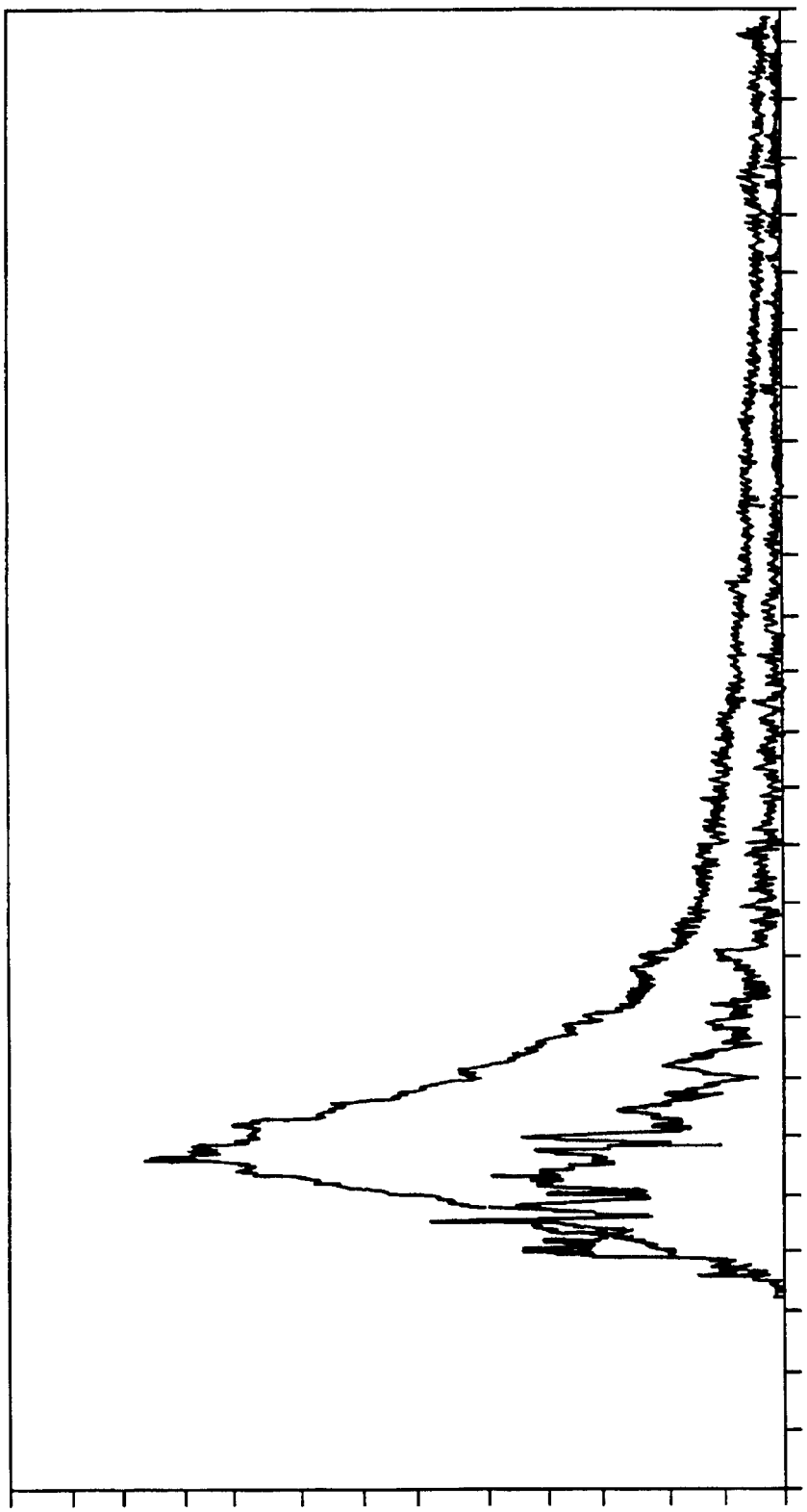

FIG. 44C shows the test signal of 443 cps, in addition to the trace shape is markedly different, this is most clearly shown by FIG. 44D, the superposition of 44C and 44B. The final trace of this set, 44E, is that of the test sample and background after the water signal has been removed.

The traces suggest that the background signal is not due to a number of fully active liposomes but that all or many of them have a low contained signal.

The shift in peak position, suggests larger and/or more dense particles, thus it may be concluded that on peptide binding that the test liposomes are susbstantially fully filled, or filled until enzyme deactivation. Thus the liposome assay has been shown to operate as digital on/off with peptide activation whilst the background generates a low signal in all, or a population, of the liposomes.

This indicates single particle detection methods may be used with significantly higher signal to noise. In this work the fluid flow was a jet stream generating significant scatter, the use of a square walled flow cell and of photon counting detectors will further enhance the signal to noise.

Operation of the Epics system, designed for 1–100 micron particle detection, on the very small particle sizes generated differences in the possible background measurement dependent on the discriminator setting in the previous example the background signal was swamped by the number of noise pulses from the water.

The results could be improved by using higher sensitivity discriminators.

EXAMPLE 25

Further Detection of Analyte

Example 24 was repeated using modified discriminator settings which showed that the distribution shapes of water, background liposomes and active liposomes are significantly different and thus allow more accurate analysis. Again the evidence indicates that binary activated liposomes exist as compared to many low level signal liposomes, in the background sample.

Figure 44F:
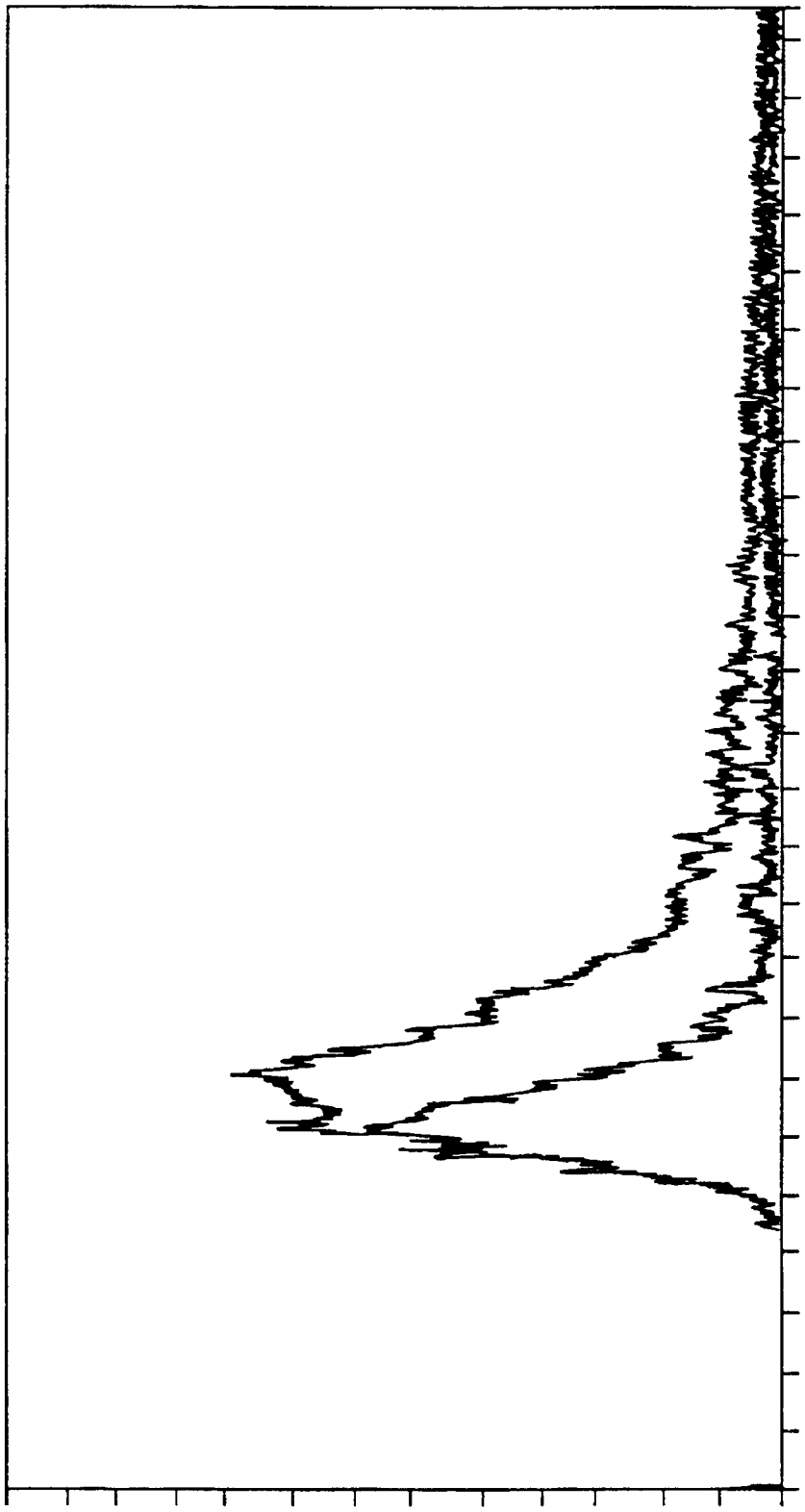
Figure 44G:
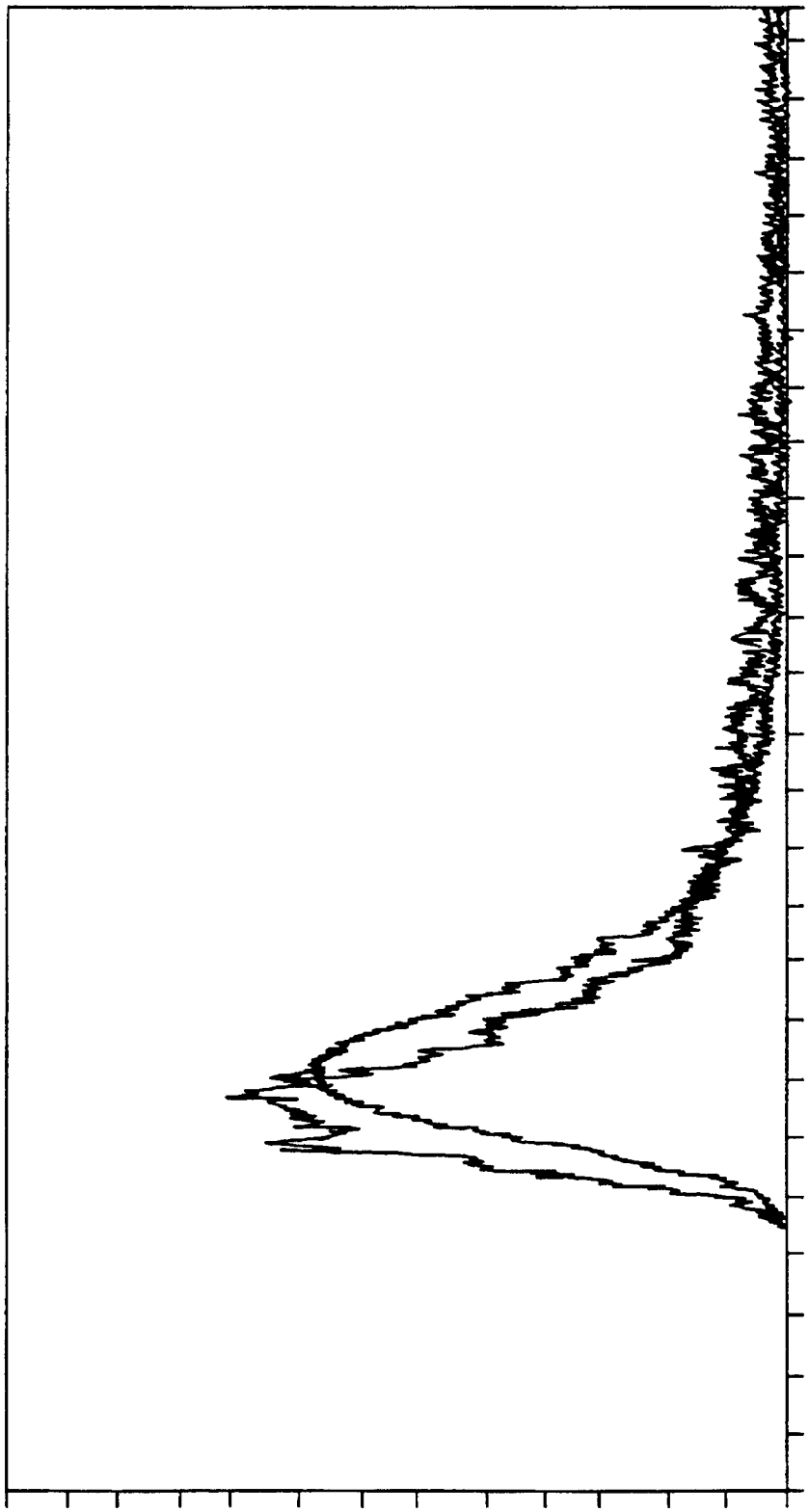
Figure 44H:
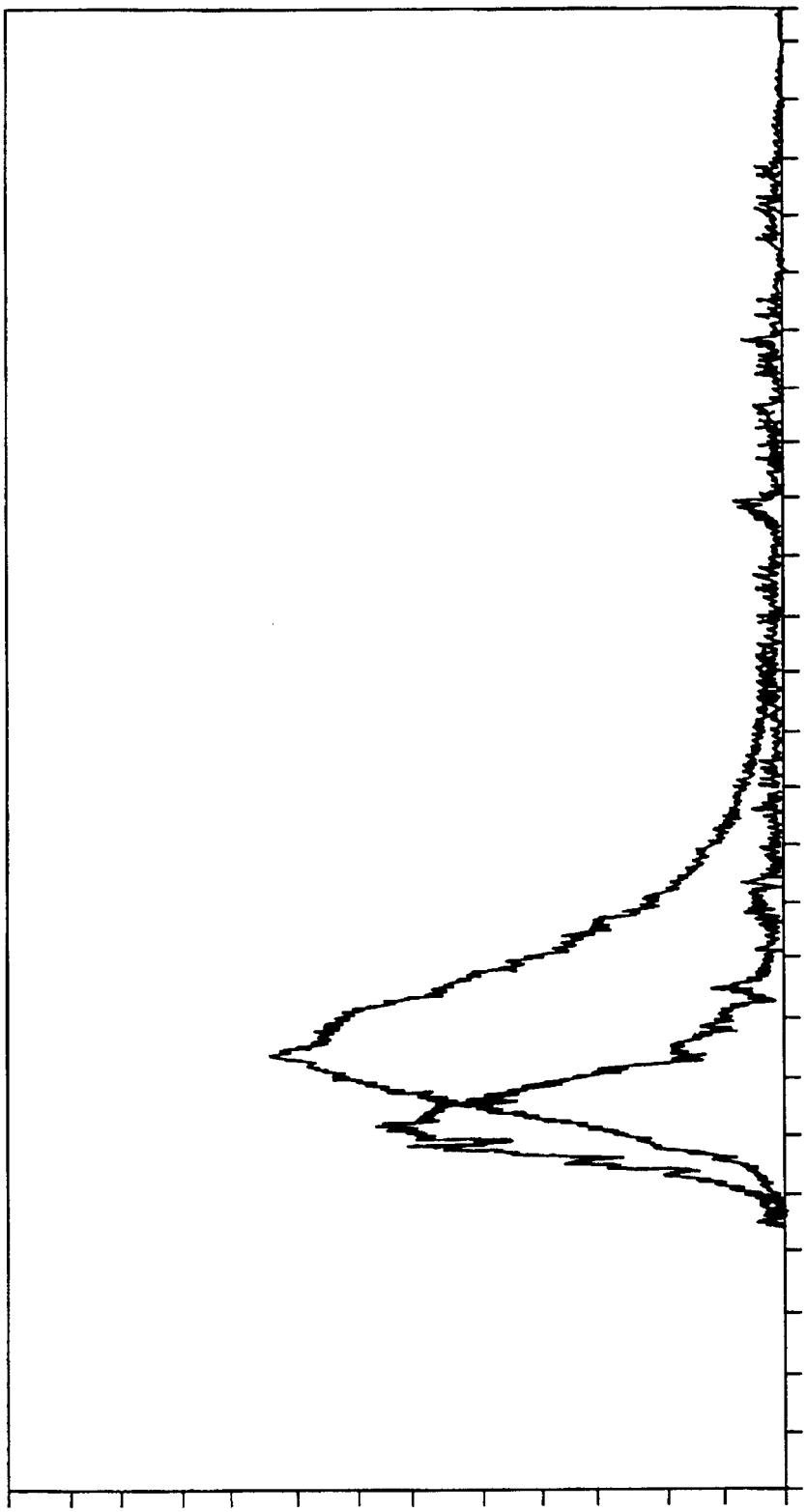

FIG. 44F shows water compared to background with counts of 15 cps and 72 cps respectively with an obvious distribution shape for the latter. FIG. 44G shows the active sample with 411 cps compared to background, with a distribution of more dense particles. FIG. 44H is included for completeness as it shows the active sample versus the water sample and indicates the very large peak shift.

Figure 44I:
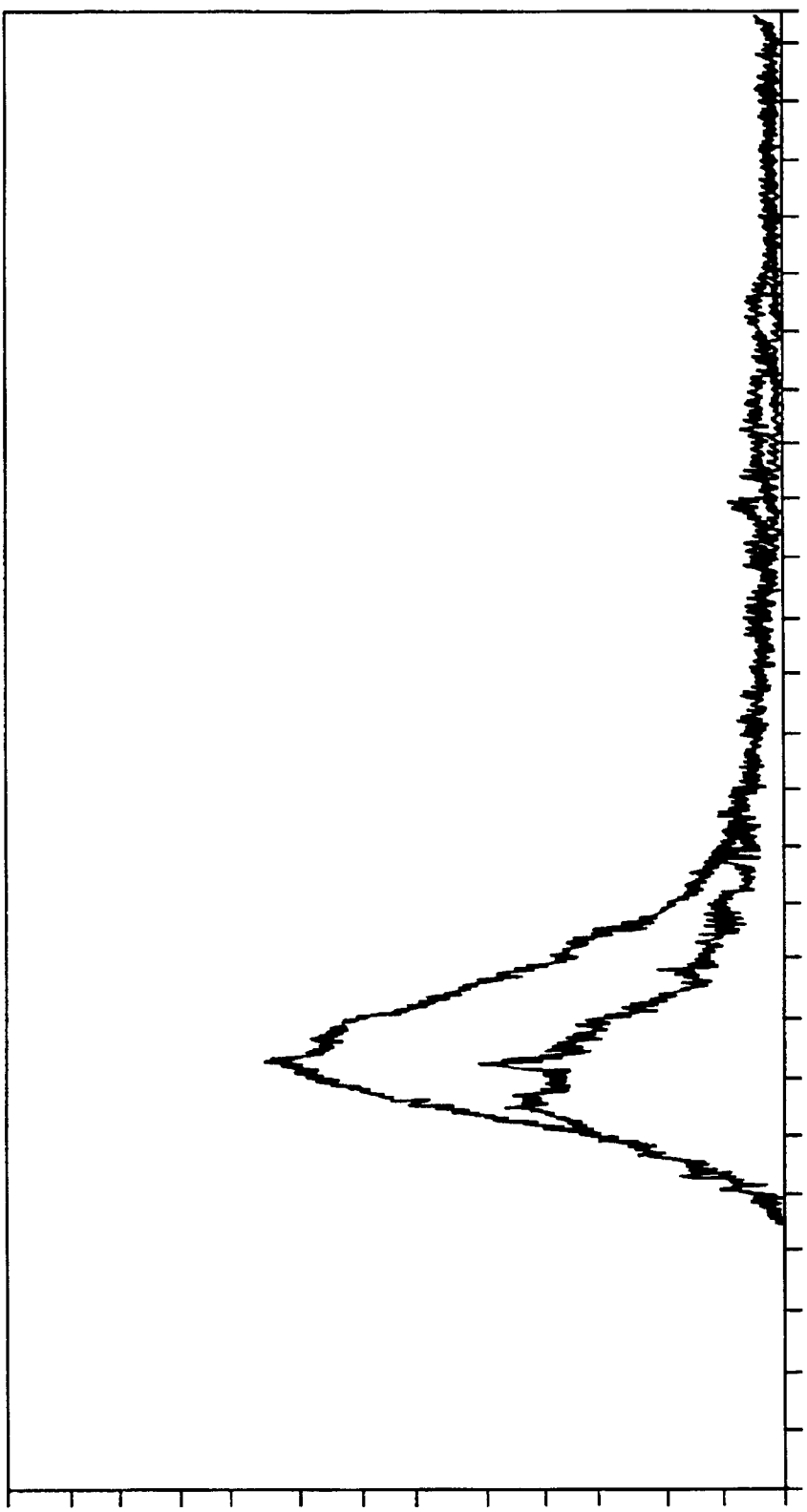
Figure 44J:
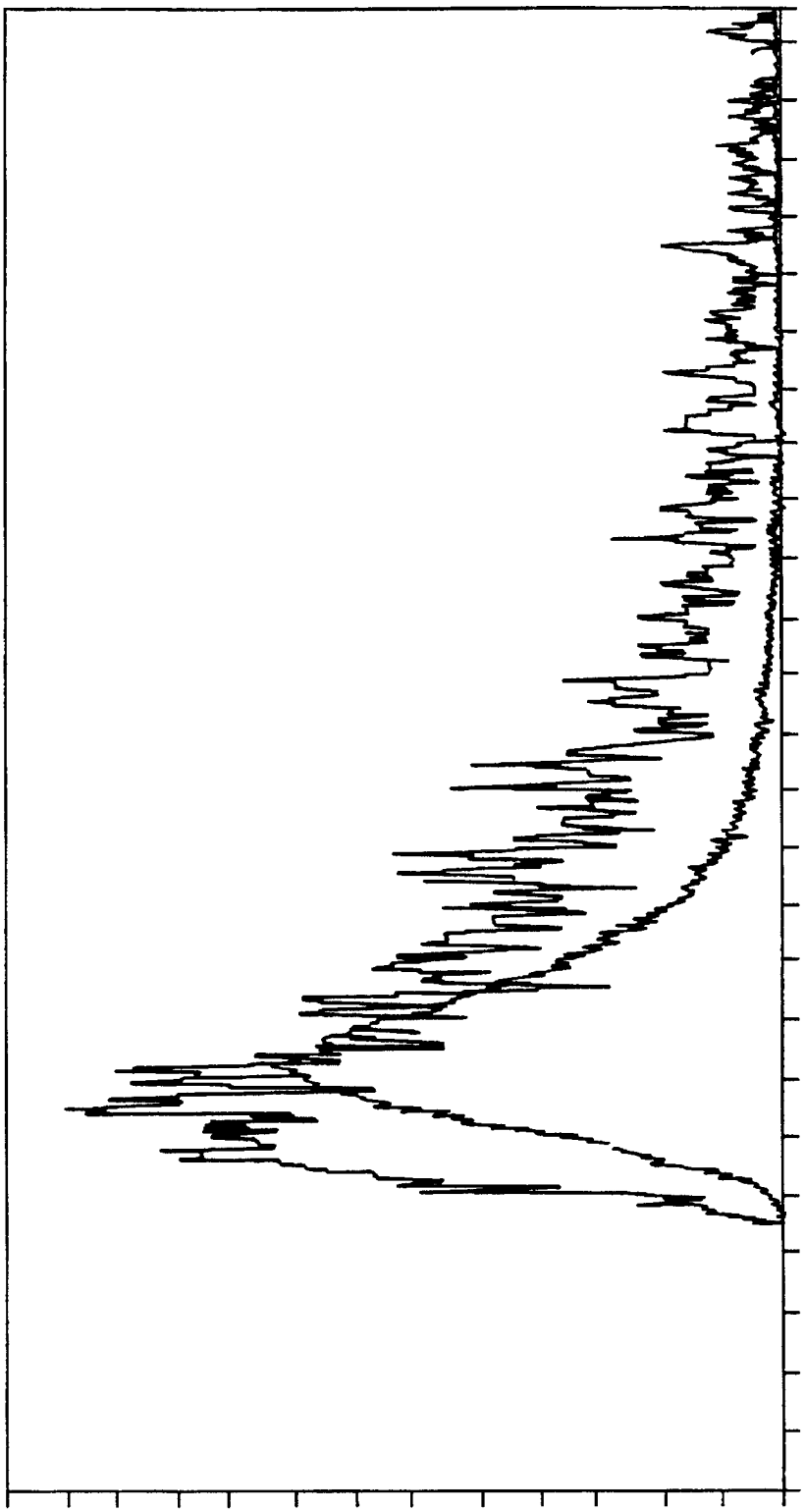

FIG. 44I shows the assay carried at a dilution of 100 fold showing a count of 57 cps, FIG. 44J the assay carried out at a dilution of 1000 fold indicates 35 cps. In the latter two examples it is important to note the distribution is a similar shape, albeit with addition of the water signal, to that produced by the test, as opposed to background, sample.

EXAMPLE 26

Further Analyte Detection

Figure 44K:
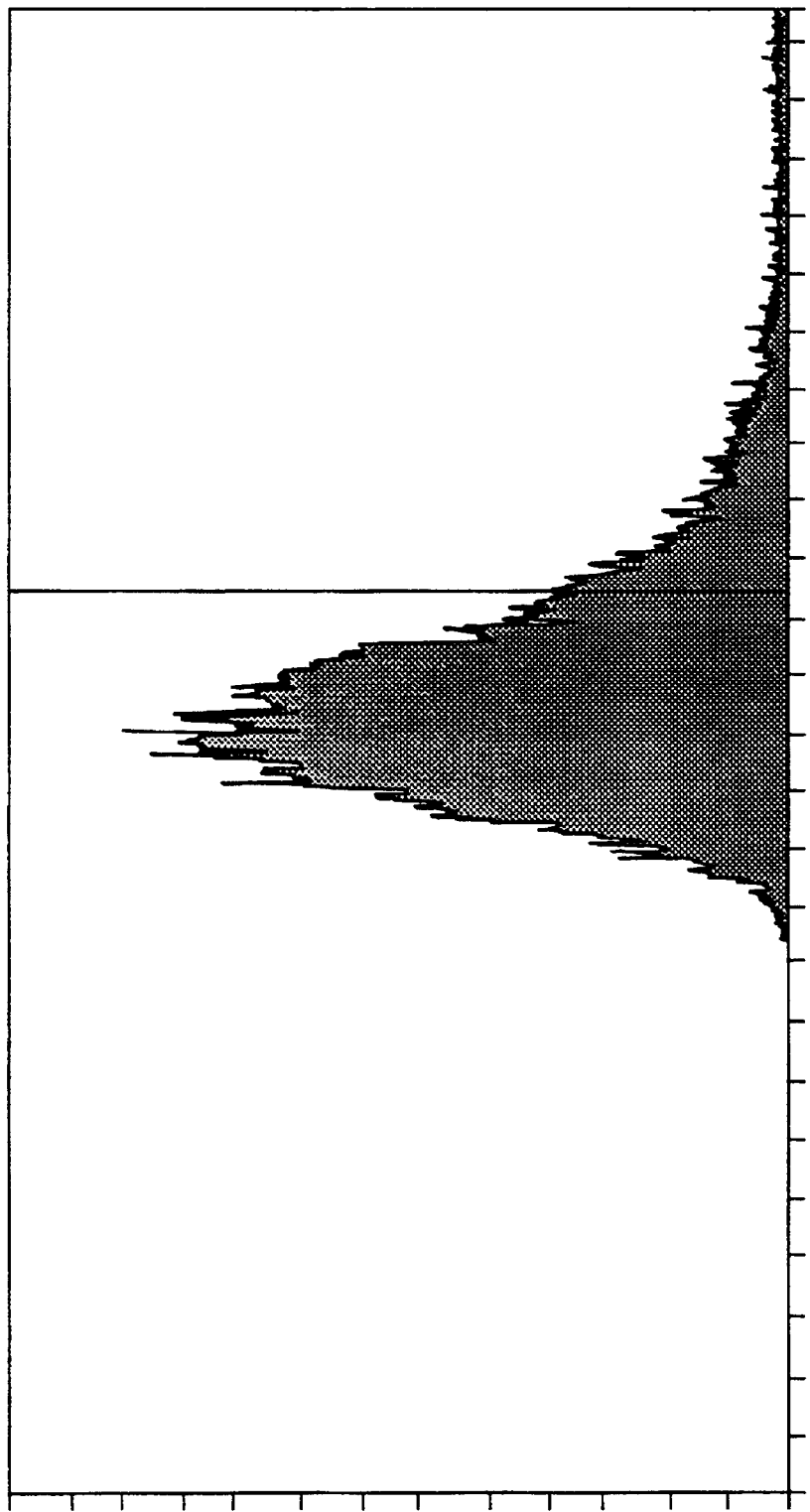

Example 25 was repeated using a higher PMT gain of 700v and lower amplifier setting of time ten. FIG. 44K is of background with a signal of 16 cps compared with 78 cps for the active assay, Figure L. Figure M shows the distribution difference clearly, the inset hand drawn figure indicating the trace cross-over.

Figure 44L:
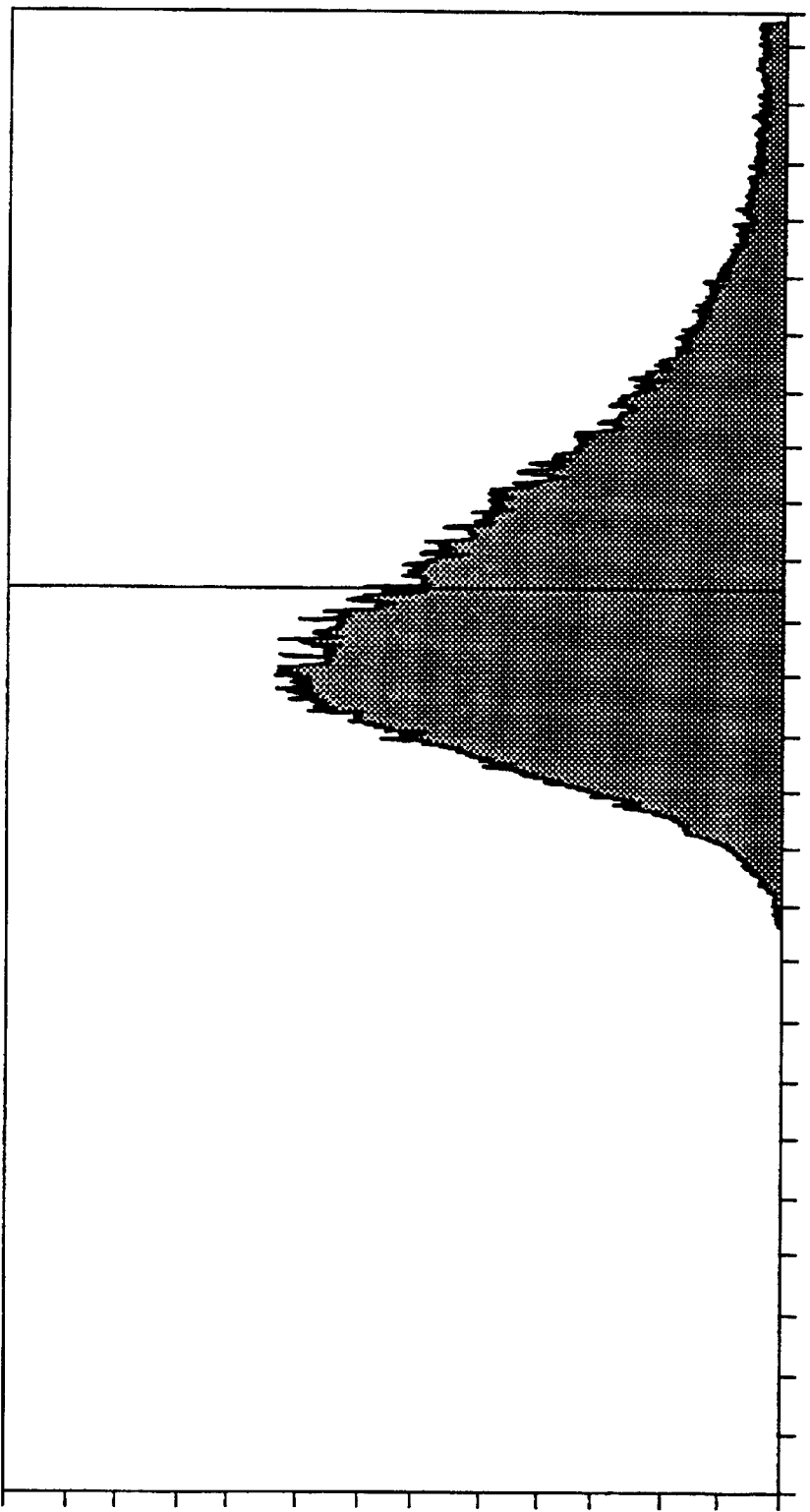
Figure 44N:
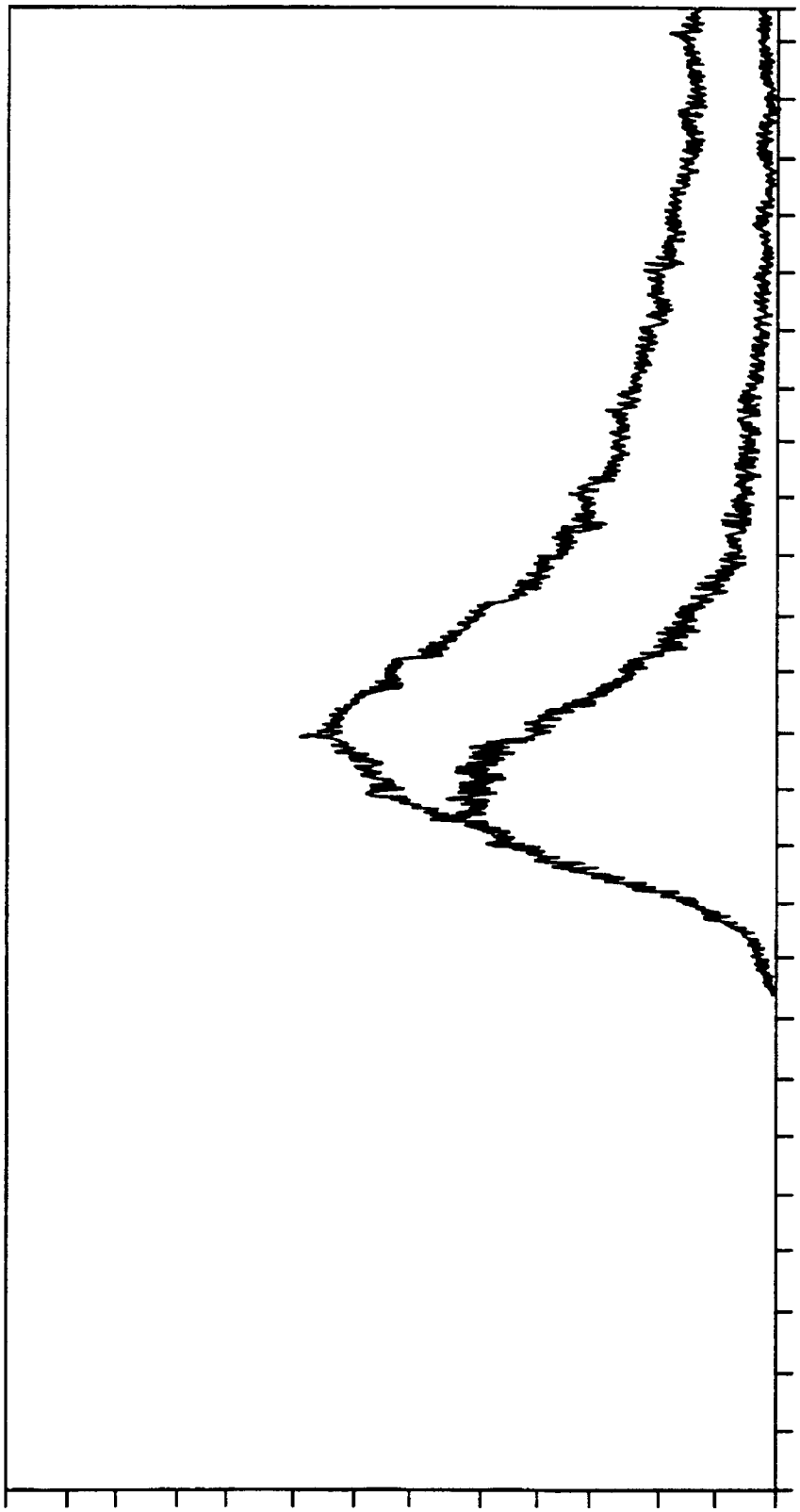
Figure 44O:
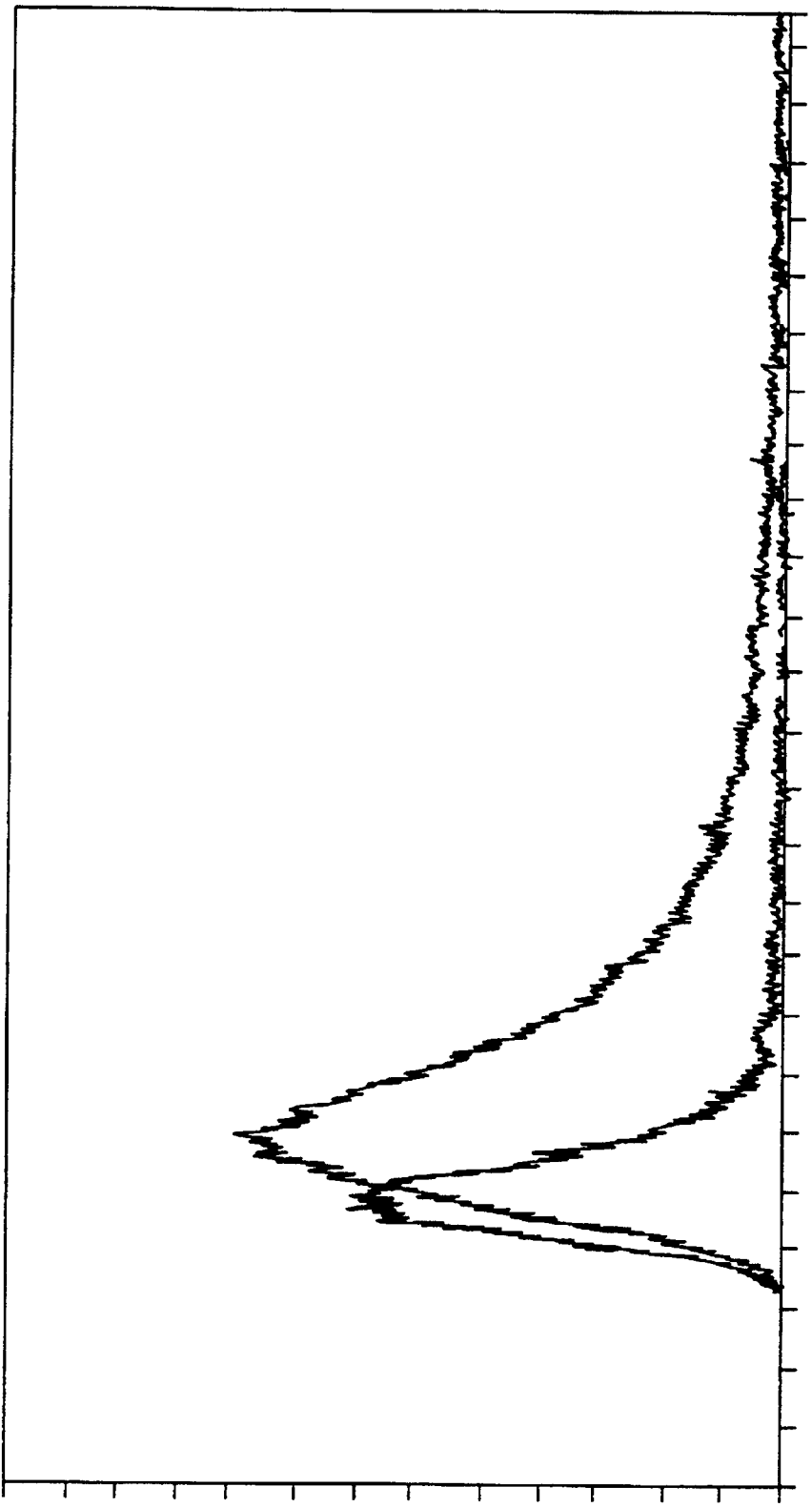
Figure 44P:
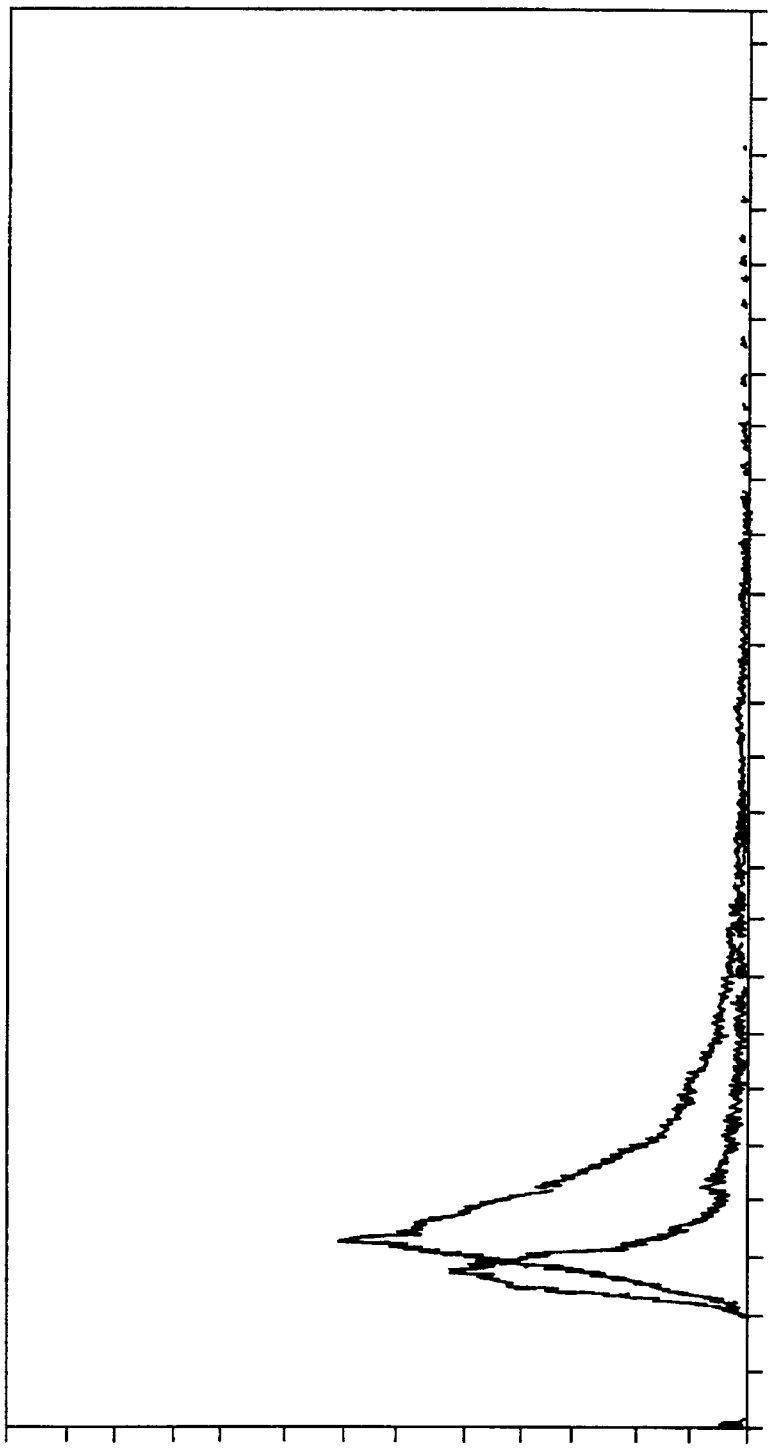
Figure 44Q:
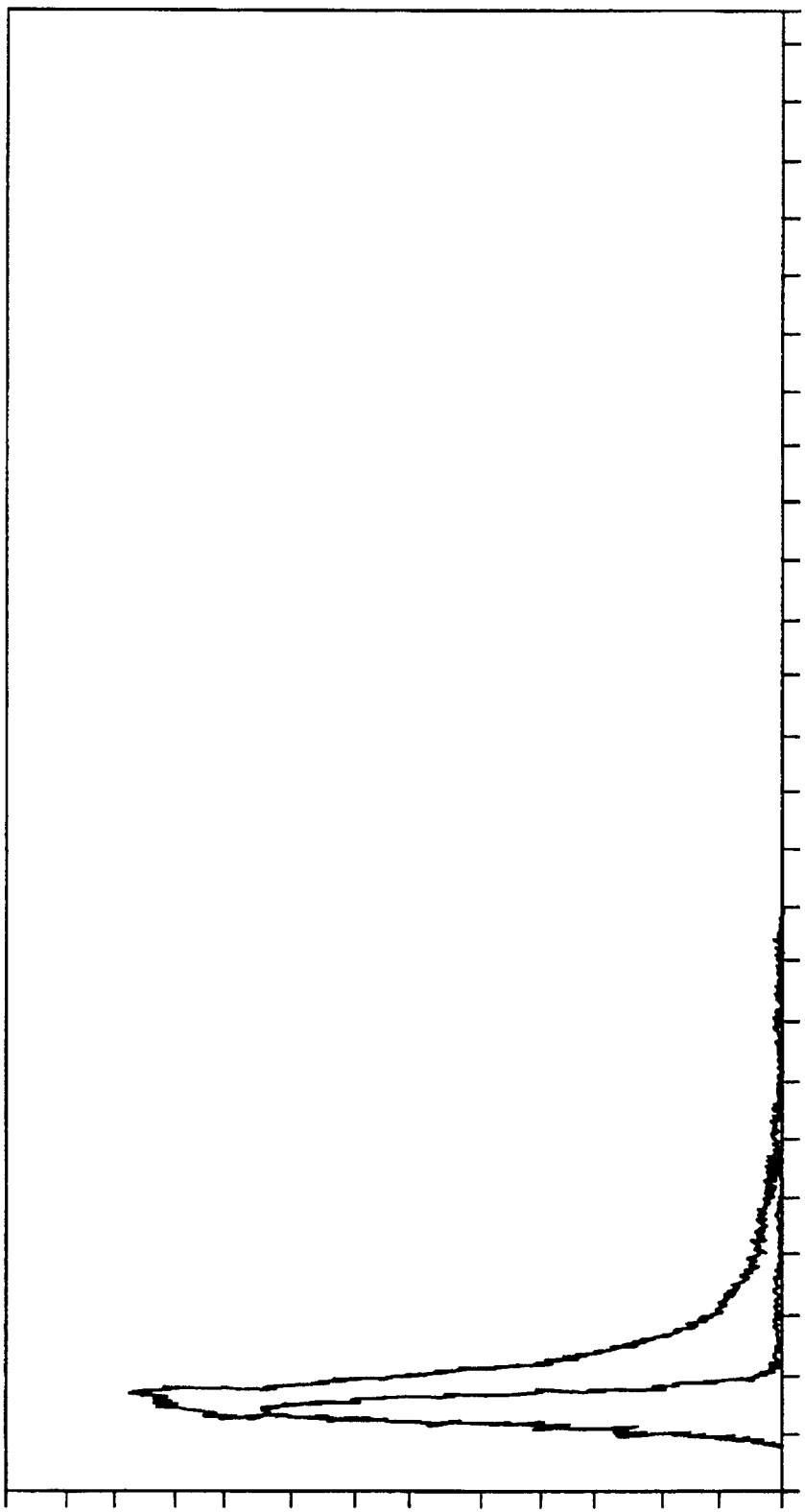
Figure 44R:
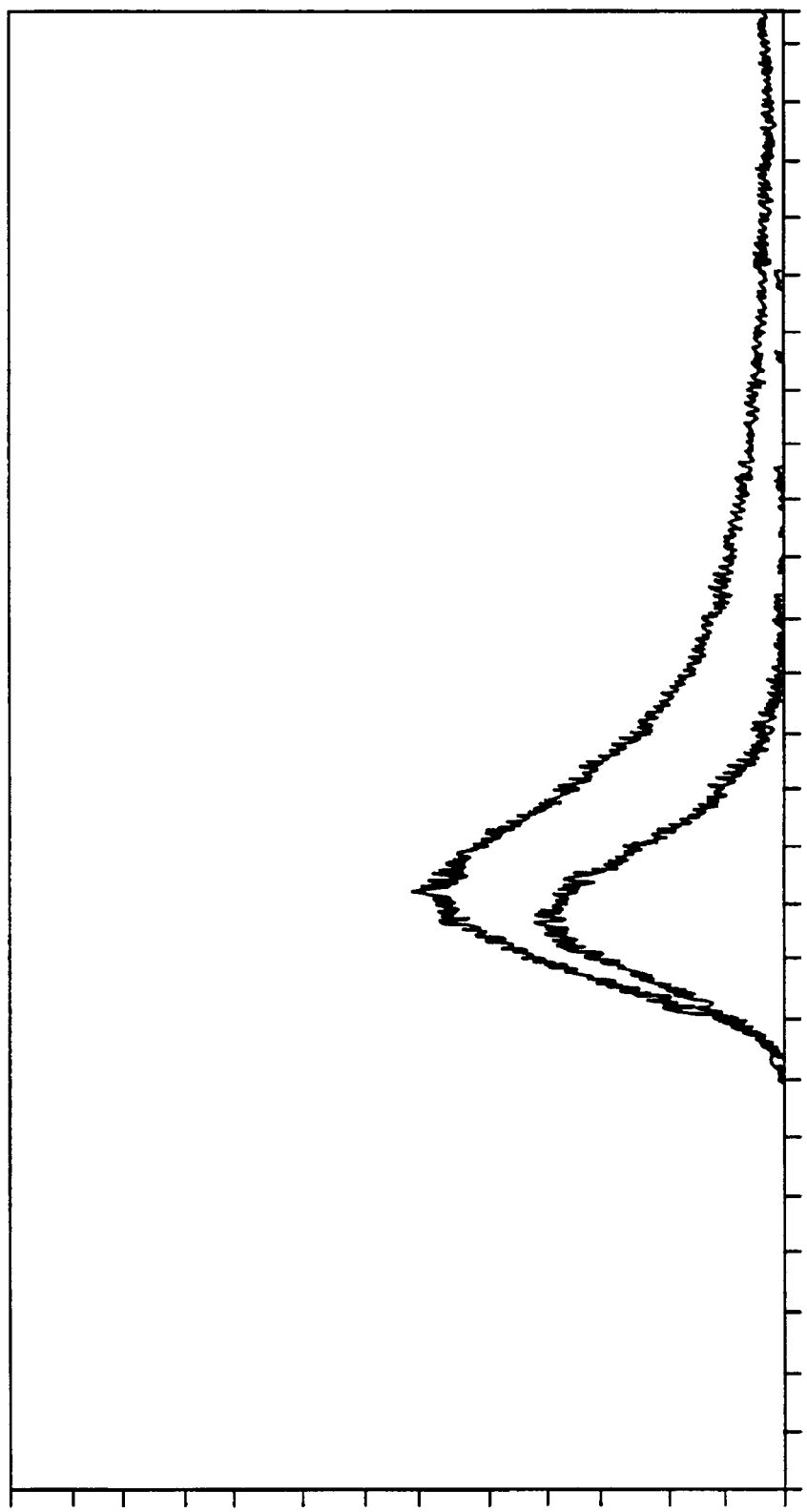
Figure 44S:
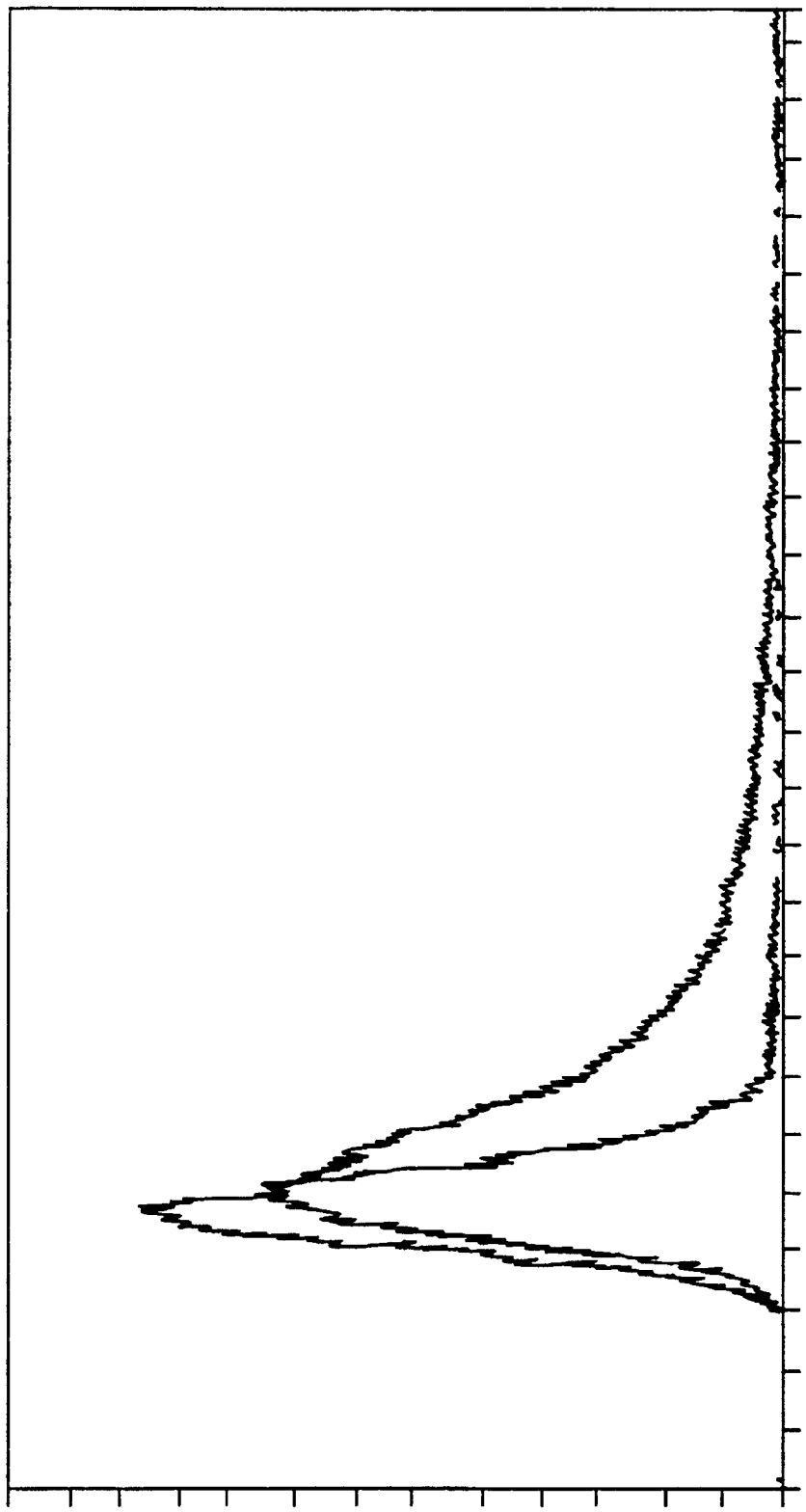

The traces FIGS. 44K and 44L where integrated for all data above the $625^{th}$ channel, removing a significant quantity of the background signal. The signal strengths are 5:1 when considering all data and 12.1 when selecting data above the $625^{th}$ point for active to background samples further indicating different distribution shapes.

To show the results cannot be considered an artefact of the instrument settings the instrument was checked at a wide number of settings and voltages where active sample was compared with the flow stream (no water was injected as a sample).

At 800 mW, trace 44N was produced using an amplifier gain of x50, trace 44O was produced using an amplifier setting of x20, 44P was produced using a gain of 10 and 44Q using a gain of 5. As would be expected separation decreased with reduced gain. At 700 mW trace 44R was produced at a gain of 20 and trace 44S at a gain of 5.

What is claimed is:

1. A method for detecting an analyte in a sample, said method comprising (a) contacting a sample suspected of containing said analyte with a signal container in an assay medium comprising at least one moiety, said signal container comprising a barrier, a signal generating reagent and an element, said barrier defining an interior space of said signal container with at least one surface separating said signal generating reagent and any analyte present in the sample, said signal generating reagent producing a signal indicative of the presence of the analyte on activation by interacting with at least one moiety, said element interacting specifically with said analyte the interaction resulting in the appearance of a transport mechanism through said barrier thereby allowing ingress or egress of said at least one moiety through said barrier, said at least one moiety causing activation of the signal generating reagent within the signal container and producing a signal within the signal container; and (b) detecting said signal as an indication of whether the analyte is present in the sample.

2. The method according to claim 1 wherein said element is present on the surface of said signal container prior to said interacting.

3. The method according to claim 1 wherein said interacting of said element and said analyte releases a permeabilizing reagent which permeabilizes said surface of said signal container.

4. The method according to claim 1 wherein said signal container comprises a membrane structure.

5. The method according to claim 1 wherein said signal container comprises a liposome or nanosphere.

6. The method according to claim 5 wherein said signal container comprises a biotinylated liposome.

7. The method according to claim 1 wherein the signal container is between 1 nm and 100 μm in diameter.

8. The method according to claim 1 wherein the transport mechanism comprises opening of a channel or a permeability perturbation in the surface.

9. The method according to claim 1 wherein said at least one moiety is an ion.

10. The method according to claim 1 wherein said element comprises an antibody or a binding fragment thereof.

11. The method according to claim 1 wherein the signal comprises a fluorescent signal.

12. The method according to claim 11 wherein the fluorescent signal is modified by interaction of cobalt ions and a dye.

13. The method according to claim 1 wherein the signal is produced as a result of an enzyme reaction.

14. The method according to claim 13 wherein said enzyme reaction is catalzed by a cofactor.

15. The method according to claim 1 wherein the signal is detected using surface plasmon resonance.

16. The method according to claim 1 wherein the signal is detected using a single particle detection method.

17. The method according to claim 16 wherein said single particle detection method is flow cytometry.

18. The method according to claim 1 wherein said activation comprises a sequence of more than one event.

19. The method according to claim 18 wherein the sequence comprises activation of a peptide which is a component of a transport mechanism, followed by analyte interaction.

20. The method according to claim 19 wherein the said peptide is activated by adjusting pH or by photoactivation.

21. The method according to claim 1 wherein the signal container is concentrated or separated from the assay medium before said detecting.

22. The method according to claim 1 wherein the signal container has a shape having three mutually perpendicular dimensions and none of said dimensions is more than 4 times greater than either of the other two.

23. The method according to any one of claims 1–14 or 22 wherein the sample contains a quenching agent which quenches signals generated outside the signal container.

24. A process for detecting an analyte in a sample, said process comprising (a) contacting a sample suspected of containing said analyte with a signal container in an assay medium comprising at least one moiety, said signal container comprising a barrier, a signal generating reagent and an element, said barrier defining an interior space of said signal container with at least one surface separating said signal generating reagent and any analyte present in the sample, said signal generating reagent producing a signal indicative of the presence of the analyte on activation by interacting with at least one moiety, said element interacting specifically with said analyte, and resulting in the appearance of a transport mechanism through said barrier thereby allowing ingress or egress of said at least one moiety through said barrier, without egress of signal from the signal container, said at least one moiety causing activation of the signal generating reagent within the signal container and producing a signal within the signal container; and (b) detecting said signal as an indication of whether the analyte is present in the sample.

25. A signal container comprising a barrier, a signal generating reagent and an element, said barrier defining an interior space of said signal container with at least one surface separating said signal generating reagent from an external surface of said barrier which, when in use in a method for detecting the presence of an analyte in a sample, contacts said analyte, said signal generating reagent producing a signal indicative of the presence of the analyte on activation by interacting with at least one moiety, said element interacting specifically with said analyte, when said signal container is in use in said method, resulting in the appearance of a transport mechanism through said barrier, thereby allowing ingress or egress of said at least one moiety so as to cause activation of the signal generating reagent within the signal container and produce a signal within the signal container.

26. A kit for detecting an analyte, said kit comprising the signal container of claim 25 and optionally a diluent.

* * * * *